United States Patent [19]
Gehring et al.

[11] Patent Number: 5,028,717
[45] Date of Patent: Jul. 2, 1991

[54] HERBICIDAL AND FUNGICIDAL AGENTS BASED ON SUBSTITUTED PYRAZOLIN-5-ONE DERIVATIVES

[75] Inventors: Reinhold Gehring, Wuppertal; Markus Lindig, Hilden; Heinz-Jürgen Wroblowsky, Langenfeld; Hans-Joachim Santel, Leverkusen; Robert R. Schmidt, Bergisch-Gladbach; Wilhelm Brandes, Leichlingen; Robert H. Strang, Duesseldorf, all of Fed. Rep. of Germany

[73] Assignee: Bayer Aktiengesellschaft, Leverkusen, Fed. Rep. of Germany

[21] Appl. No.: 433,483

[22] Filed: Nov. 8, 1989

Related U.S. Application Data

[62] Division of Ser. No. 130,380, Dec. 8, 1987, Pat. No. 4,909,827.

[30] Foreign Application Priority Data

Dec. 17, 1986 [DE] Fed. Rep. of Germany ....... 3643148
Aug. 25, 1987 [DE] Fed. Rep. of Germany ....... 3728278

[51] Int. Cl.$^5$ ............................................ C07D 231/22
[52] U.S. Cl. .................................................. 548/367
[58] Field of Search ...................... 548/365, 367; 71/92

[56] References Cited

FOREIGN PATENT DOCUMENTS 2081595 12/1971 France .
887509 1/1962 United Kingdom .

OTHER PUBLICATIONS

*Beilsteins Handbuch der Organischen Chemie*, 4$\frac{3}{4}$, V. 25, Teil 5 (1982) pp. 3731–3733, 3809.

*Primary Examiner*—Robert W. Ramsuer
*Attorney, Agent, or Firm*—Sprung Horn Kramer & Woods

[57] ABSTRACT

The invention relates to the use of partly known substituted pyrazolin-5-one derivatives of the formula (I)

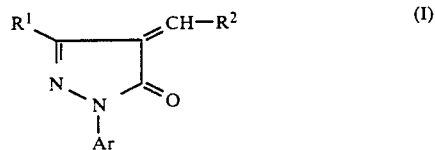

as herbicides and fungicides, new substituted pyrazolin-5-one derivatives and processes for their preparation.

6 Claims, No Drawings

HERBICIDAL AND FUNGICIDAL AGENTS BASED ON SUBSTITUTED PYRAZOLIN-5-ONE DERIVATIVES

This is a division of application Ser. No. 130,380, filed Dec. 8, 1987 now U.S. Pat. No. 4,909,827.

The invention relates to the use of partly known substituted pyrazolin-5-one derivatives as herbicides and fungicides, new substituted pyrazolin-5-one derivatives and processes for their preparation.

It is already known that substituted pyrazolin-5-ones such as, for example, 4-(cyanomethyloximino)-3-methyl-1-phenyl-pyrazolin-5-one possess fungicidal properties (cf. EP-OS (European Published Specification) No. 0,166,171).

It is additionally already known that substituted pyrazolin-5-ones such as, for example, [4-(2,4-dichlorobenzoyl)-1,3-dimethylpyrazol-5-yl]-4-methyl-phenylsulphonate possess herbicidal properties (cf. DE-OS (German Published Specification) No. 2,513,750).

The action of these compounds is, however, not always completely satisfactory in all areas of application, in particular at low application rates and concentrations.

Furthermore, 1-(4-chlorophenyl)-pyrazolin-5-one derivatives such as, for example, 1-(4-chlorophenyl)-3-methyl-4-piperidinomethylene-pyrazolin-5-one, 1-(4-chlorophenyl)-3-methyl-4-morpholino-methylene-pyrazolin-5-one, 1-(4-chlorophenyl)-4-[4-(fluorophenylamino)-methylene]-3-methyl-pyrazolin-5-one, 1-(4-chlorophenyl)-3-methyl-4-aminomethylene-pyrazolin-5-one and 1-(2-ethylphenyl)-3-methyl-4-aminomethylene-pyrazolin-5-one, are known. These compounds have strongly fire-inhibiting and fungicidal actions, among others, but herbicidal action against dicotyledon weeds is also mentioned (cf. Kreuzberger et al., Arch. Pharm. (Weinheim) 319, 865–871 (1986) and 318, 89–91 (1985)).

In addition, 4-aminomethylene-pyrazolin-5-one derivatives are known, such as, for example, 1-(4-bromophenyl)-3-methyl-4-methylaminomethylene-pyrazolin-5-one, which are described as complexing agents (cf. Alam et al., Zh. Org. Khim. 1977, 13(4), 863–868 (Russ.)) or 3-methyl-4-chlorophenylaminomethylenepyrazolin-5-ones, with which structural investigations have been performed (cf. Jean E. Rockley et al., Aust. J. Chem. 1981, 34(5), 1117–1124 (Engl.)).

Additionally, 1-(4-chlorophenyl)-3-methyl-4-anilinomethylene-pyrazolin-5-one is known as a starting compound for the preparation of nickel complexes of azines (cf. European Patent No. 0,020,299).

Furthermore, 1-phenyl-3-(4-methoxyphenyl)-4-N,N-dimethylaminomethylidene-pyrazolin-5-one is known as a starting compound for the preparation of pharmaceutical products (cf. British Patent No. 887,509).

It has been found that the partly known substituted pyrazolin-5-one derivatives of the formula (I)

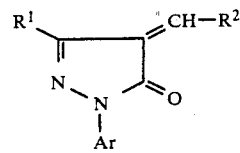

in which

R$^1$ represents hydrogen, alkyl, cycloalkyl, halogenoalkyl, in each case optionally substituted alkenyl or alkinyl, halogenoalkenyl, alkoxy, alkoxyalkyl, alkylthioalkyl, alkylsulphonylalkyl, alkylsulphinylalkyl, alkoxycarbonylalkyl, dialkoxy(thio)phosphorylalkyl, in each case optionally substituted aryl, aralkyl, aryloxyalkyl or arylthioalkyl or an optionally substituted heterocycle, or heterocyclylalkyl or the groupings —NH—CO—R$^{10}$ or —CO—O—R$^{11}$, wherein R$^{10}$ and R$^{11}$, in each case independently of one another, represent alkyl or aryl, R$^2$ represents the groupings —NHR$^3$, —NR$^4$R$^5$ or —N-HOR$^6$, wherein R$^3$ represents hydrogen, alkyl, halogenoalkyl, alkenyl, halogenoalkenyl, alkoxyalkyl, optionally substituted aralkyl or optionally substituted aryl, R$^4$ represents alkyl, R$^5$ represents alkyl or R$^4$ and R$^5$, together with the nitrogen atom to which they are bonded, represent a heterocyclic ring which can contain further hetero atoms, R$^6$ represents hydrogen, alkyl, halogenoalkyl, alkenyl halogenoalkenyl or optionally substituted aralkyl and Ar represents optionally substituted aryl, an optionally substituted and/or optionally anellated heterocycle or the group

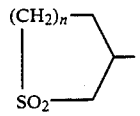

where n represents the numbers 1 or 2, and their salts, excluding the compounds 1-(4-chlorophenyl)-3-methyl-4-piperidino-methylene-pyrazolin-5-one, 1-(4-chlorophenyl)-3-methyl-4-morpholino-methylene-pyrazolin-5-one, 1-(4-chlorophenyl)-4-[4-(fluorophenylamino)-methylene]-3-methyl-pyrazolin-5-one and 1-(4-chlorophenyl)-3-methyl-4-aminomethylene-pyrazolin-5-one (cf. Kreutzberger, A. and Kolter, K., Arch. der Phar., 319, 10, 865–871, (1986)), exhibit strong herbicidal and fungicidal properties.

The compounds of the formula (I) can exist as geometric isomers (E/Z isomers) or isomeric mixtures of variable composition. The use of both the pure isomers and also the isomeric mixtures is claimed according to the invention.

Additionally, some of the compounds of the formula (I) can exist in tautomeric equilibrium:

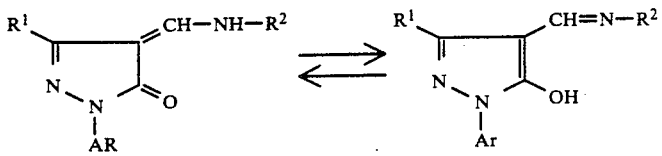

In the following the use of compounds of the formula (I) is always referred to, for the sake of simplicity, although both the pure compounds and also their mixtures with variable amounts of the tautomeric compounds are meant.

Surprisingly, the partly known substituted pyrazolin-5-one derivatives of the formula (I) exhibit better fungicidal properties at suitable application concentrations than the 4-(cyanomethyloximino)-3-methyl-1-phenyl-pyrazolin-5-one known from the state of the art, which is a constitutionally similar active compound of identical mode of action. Additionally, the partly known substituted pyrazolin-5-one derivatives of the formula (I) also exhibit better herbicidal properties at suitable application concentrations than the [4-(2,4-dichlorobenzoyl)-1,3-dimethylpyrazol-5-yl]-4-methylphenylsulphonate known from the state of the art, which is a constitutionally similar active compound of identical mode of action.

The substituted pyrazolin-5-one derivatives which can be used according to the invention are generally defined by the formula (I).

It is preferred to use compounds of the formula (I) in which $R^1$ represents hydrogen, straight-chain or branched alkyl with 1 to 8 carbon atoms, cycloalkyl with 3 to 7 carbon atoms, halogenoalkyl with 1 to 4 carbon atoms and 1 to 9 identical or different halogen atoms, such as, in particular, fluorine and chlorine atoms, in each case optionally substituted alkenyl or alkinyl with in each case 2 to 6 carbon atoms, where substituents which may be mentioned are unsubstituted phenyl or mono-, di- or trisubstituted phenyl, the substituents being identical or different, and where suitable phenyl substituents are the aryl substituents listed under Ar; $R^1$ furthermore represents halogenoalkenyl with 2 to 6 carbon atoms and 1 to 10 identical or different halogen atoms such as, in particular, fluorine and chlorine, alkoxy with 1 to 8 carbon atoms, alkoxyalkyl with in each case 1 to 8 carbon atoms in the individual alkyl parts, alkylthioalkyl, alkylsulphonylalkyl or alkylsulphinylalkyl with in each case 1 to 8 carbon atoms in the individual alkyl parts, alkoxycarbonylalkyl with 1 to 4 carbon atoms in the alkoxy part and 1 to 4 carbon atoms in the alkyl part, a 5- or 6-membered, optionally fluorine-, chlorine-, methyl- and/or ethylsubstituted heterocycle, in particular furanyl, thienyl; furanylmethyl, thienylmethyl or $R^1$ furthermore represents aryl, arylalkyl, aryloxyalkyl or arylthioalkyl in each case optionally mono-, di-, tri-, tetra- or pentasubstituted in the aryl part by identical or different substituents and in each case with 6 to 10 carbon atoms in the aryl part and, where appropriate, 1 to 4 carbon atoms in the alkyl part, and where suitable aryl substituents are the aryl substituents listed under Ar, $R^1$ furthermore represents the groupings —NH—CO—$R^{10}$ or —CO—O—$R^{11}$, wherein $R^{10}$ and $R^{11}$, in each case independently of one another, represent $C_1$–$C_4$-alkyl or phenyl, $R^2$ represents the groupings —NHR$^3$, —NR$^4$R$^5$ or —NHOR$^6$, wherein $R^3$ represents hydrogen, straight-chain or branched alkyl with 1 to 8 carbon atoms, halogenoalkyl with 1 to 6 carbon atoms and 1 to 12 identical or different halogen atoms, such as in particular fluorine and chlorine atoms, straight-chain or branched alkenyl with 2 to 12 carbon atoms, halogenoalkenyl with 2 to 6 carbon atoms and 1 to 10 identical or different halogen atoms, such as in particular fluorine and chlorine atoms, alkoxyalkyl with in each case 1 to 8 carbon atoms in the alkoxy or alkyl part, optionally mono- or polysubstituted aralkyl with 1 to 4 carbon atoms in the straight-chain or branched alkyl part and 6 to 10 carbon atoms in the aryl part, the substituents being identical or different, optionally mono-, di-, tri-, tetra- or pentasubstituted aryl with 6 to 10 carbon atoms, the substituents being identical or different, and where suitable aryl substituents are in each case: halogen, straight-chain or branched alkyl with 1 to 4 carbon atoms and dialkylamino with in each case 1 to 4 carbon atoms in the alkyl part, $C_1$–$C_4$-alkoxy and halogeno-$C_1$–$C_4$-alkyl, $R^4$ represents alkyl with 1 to 6 carbon atoms, $R^5$ represents alkyl with 1 to 6 carbon atoms or $R^4$ and $R^5$, together with the nitrogen atom to which they are bonded, represent a heterocyclic 5- or 6-membered ring, which can contain oxygen, sulphur and/or nitrogen as further hetero atoms, $R^6$ represents hydrogen, straight-chain or branched alkyl with 1 to 8 carbon atoms, halogenoalkyl with 1 to 6 carbon atoms and 1 to 12 identical or different halogen atoms, such as in particular fluorine or chlorine atoms, straight-chain or branched alkenyl with 2 to 12 carbon atoms, halogenoalkenyl with 2 to 6 carbon atoms and 1 to 10 identical or different halogen atoms, such as in particular fluorine and chlorine atoms, optionally mono- or polysubstituted aralkyl with 1 to 4 carbon atoms in the alkyl part and 6 to 10 carbon atoms in the aryl part, the substituents being identical or different, and where suitable aryl substituents are halogen, $C_1$–$C_4$-alkyl, halogeno-$C_1$–$C_4$-alkyl and nitro, and Ar represents optionally mono- or polysubstituted aryl with 6 to 10 carbon atoms, in particular phenyl or naphthyl, the substituents being identical or different, and where suitable aryl substituents are: halogen; nitro; cyano; carboxyl; alkoxycarbonyl with 1 to 4 carbon atoms, $C_1$–$C_4$-alkyl, $C_1$–$C_4$-alkoxy; or $C_1$–$C_4$-alkylthio; $C_3$–$C_6$-alkinyloxy; halogeno-($C_1$–$C_4$-)-alkyl, halogeno-($C_1$–$C_4$-)-alkoxy or halogeno($C_1$–$C_4$)alkylthio with in each case 1 to 9 identical or different halogen atoms; phenyl; $C_1$–$C_4$-alkylsulphonyl and halogeno-($C_1$–$C_4$)-alkylsulphonyl with in each case 1 to 9 identical or different halogen atoms; and di-($C_1$–$C_4$)-alkylamino an optionally substituted and/or optionally anellated 6-membered, aromatic heterocycle, which contains at least one nitrogen atom and where suitable substituents are the aryl substituents listed in Ar above, or represents the group

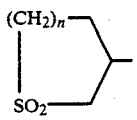

where
n represents the numbers 1 or 2,
and their salts, excluding the compounds listed under the formula (I).

Particularly preferred compounds of the formula (I) according to the invention are those in which $R^1$ represents hydrogen, straight-chain or branched alkyl with 1 to 4 carbon atoms, cycloalkyl with 3 to 6 carbon atoms, halogenoalkyl with 1 to 3 carbon atoms and 1 to 7 identical or different halogen atoms, such as in particular fluorine and chlorine atoms, in each case optionally substituted alkenyl or alkinyl with in each case 2 to 4 carbon atoms, where unsubstituted phenyl or mono-, di- or trisubstituted phenyl with identical or different substituents may be mentioned as substituents, and where suitable phenyl substituents are the aryl substituents listed under Ar; $R^1$ furthermore represents halogenoalkenyl with 3 or 4 carbon atoms and 1 to 5 identical or different halogen atoms such as in particular fluorine and chlorine, alkoxy with 1 to 4 carbon atoms, alkoxyalkyl with in each case 1 to 4 carbon atoms in the individual alkyl parts, alkylthioalkyl, alkylsulphonylalkyl or alkylsulphinylalkyl with in each case 1 to 4 carbon atoms in the individual alkyl parts, alkoxycarbonylalkyl with 1 or 2 carbon atoms in the alkoxy part and 1 or 2 carbon atoms in the alkyl part, a 5- or 6-membered, optionally fluorine-, chlorine-, methyl- and/or ethyl-substituted heterocycle, in particular furanyl, thienyl; furanylmethyl, thienylmethyl or $R^1$ furthermore represents in each case optionally mono-, di-, tri-, tetra- or pentasubstituted phenyl, naphthyl, benzyl, phenylethyl, phenoxymethyl, phenoxyethyl, phenylthiomethyl or phenylthioethyl, the substituents being identical or different and where suitable phenyl substituents are in each case the phenyl substituents listed under Ar; $R^1$ furthermore represents the groupings —NH—CO—$R^{10}$ or —CO—O—$R^{11}$, wherein
$R^{10}$ and $R^{11}$ in each case independently of one another, represent $C_1$-$C_4$-alkyl or phenyl, $R^2$ represents the groupings —NH$R^3$, —NR$^4$R$^5$ or —N-HOR$^6$, wherein
$R^3$ represents hydrogen, straight-chain or branched alkyl with 1 to 4 carbon atoms, halogeno-alkyl with 1 to 4 carbon atoms and 1 to 9 identical or different halogen atoms, such as in particular fluorine and chlorine atoms, straight-chain or branched alkenyl with 2 to 6 carbon atoms, halogenoalkenyl with 2 to 4 carbon atoms and 1 to 7 identical or different halogen atoms, such as in particular fluorine and chlorine atoms, alkoxyalkyl with in each case 1 to 4 carbon atoms in the alkoxy or alkyl part, optionally mono-, di-, tri-, tetra- or pentasubstituted phenylalkyl with 1 to 3 carbon atoms in the straight-chain or branched alkyl part, the substituents being identical or different, optionally mono-, di-, tri-, tetra- or pentasubstituted phenyl, the substituents being identical or different, and where suitable phenyl substituents are in each case: halogen, straight-chain or branched alkyl with 1 or 2 carbon atoms and dialkylamino with in each case 1 or 2 carbon atoms in the alkyl part, $C_1$-$C_2$-alkoxy, halogeno-$C_1$-$C_2$-alkyl, $R^4$ represents alkyl with 1 to 4 carbon atoms,
$R^5$ represents alkyl with 1 to 4 carbon atoms or
$R^4$ and $R^5$, together with the nitrogen atom to which they are bonded, represent a heterocyclic 5- or 6-membered ring, which can contain oxygen, sulphur and/or nitrogen as further hetero atoms, $R^6$ represents hydrogen, straight-chain or branched alkyl with 1 to 6 carbon atoms, halogenoalkyl with 1 to 3 carbon atoms and 1 to 7 identical or different halogen atoms, such as in particular fluorine and chlorine atoms, straight-chain or branched alkenyl with 2 to 6 carbon atoms, halogenoalkenyl with 2 or 3 carbon atoms and 1 to 5 identical or different halogen atoms, such as in particular fluorine and chlorine atoms, optionally mono-, di-, tri-, tetra- or pentasubstituted phenylalkyl with 1 to 3 carbon atoms in the alkyl part, the substituents being identical or different, and where suitable phenyl substituents are halogen, $C_1$-$C_2$-alkyl, halogeno-$C_1$-$C_2$-alkyl and nitro, and Ar represents optionally mono-, di-, tri-, tetra- or pentasubstituted phenyl, the substituents being identical or different, and where suitable phenyl substituents are: halogen; nitro; cyano; carboxyl; alkoxycarbonyl with 1 to 3 carbon atoms; $C_1$-$C_3$-alkyl, $C_1$-$C_3$-alkoxy; $C_1$-$C_3$-alkylthio, $C_3$-$C_4$-alkinyloxy, halogeno-($C_1$-$C_3$)-alkyl, halogeno-($C_1$-$C_4$)-alkoxy or halogeno-($C_1$-$C_4$)-alkylthio with in each case 1 to 7 identical or different halogen atoms; phenyl; $C_1$-$C_3$-alkylsulphonyl and halogeno-($C_1$-$C_3$)alkylsulphonyl with in each case 1 to 7 identical or different halogen atoms; and di-($C_1$-$C_3$)-alkylamino, an optionally substituted and/or optionally anellated 6-membered, aromatic hetero-cycle, which contains at least one nitrogen atom and where suitable substituents are the phenyl substituents listed above in Ar, or represents the group

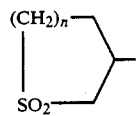

where
n represents the numbers 1 or 2,
and their salts, excluding the compounds already mentioned under formula (I).

Very particularly preferred compounds of the formula (I) according to the invention are those in which $R^1$ represents hydrogen, methyl, ethyl, n-propyl, i-propyl, n-butyl, i-butyl, tert.-butyl, cyclopropyl, cyclohexyl, trifluoromethyl, vinyl, allyl, butenyl, propargyl, 2-phenylvinyl, chloroallyl, methoxy, ethoxy, methoxymethyl, ethoxymethyl, methylthiomethyl, ethylthiomethyl, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, furanyl, furanylmethyl, thienyl, thienylmethyl, pyridyl, phenylthio, ethoxycarbonylmethyl, methoxycarbonylmethyl, R¹ furthermore represents in each case optionally mono-, di- or trisubstituted phenyl, naphthyl, benzyl, phenylethyl, phenoxymethyl or phenylthiomethyl, the substituents being identical or different, and where suitable phenyl substituents are in each case the phenyl substituents listed under Ar; R¹ furthermore represents the groupings —NH—CO—R¹⁰ or —CO—O—R¹¹, wherein R¹⁰ and R¹¹, in each case independently of one another, represent methyl, ethyl or phenyl, R² represents the groupings —NHR³, —NR⁴R⁵ or —NHOR⁶, wherein R³ represents hydrogen, methyl, ethyl, n-propyl, i-propyl, i-butyl, 2,2-dimethylpropyl, n-hexyl, trifluoromethyl, 2-chloroethyl, 3-chloropropyl, propenyl, methoxymethyl, methoxyethyl, methoxypropyl, ethoxymethyl, ethoxyethyl, 3-chloroallyl, α-methylbenzyl, optionally mono-, di-, tri-, tetra- or pentasubstituted phenyl, the substituents being identical or different, and where suitable phenyl substituents are: fluorine, chlorine, methyl, methoxy, ethoxy, trifluoromethyl, trifluoroethyl, dimethylamino, R⁴ represents methyl or ethyl, R⁵ represents methyl or ethyl, or R⁴ and R⁵, together with the nitrogen atom to which they are bonded, represent piperidinyl, piperazinyl, morpholinyl or thiomorpholinyl, R⁶ represents hydrogen, methyl, ethyl, i-propyl, trifluoromethyl, 2-chloroethyl, 3-chloropropyl, propenyl, 3-chloroallyl, optionally mono-, di-, tri-, tetra- or pentasubstituted benzyl, the substituents being identical or different, and where suitable phenyl substituents are fluorine, chlorine, methyl, ethyl, trifluoromethyl and nitro and Ar represents optionally mono-, di-, tri-, tetra- or pentasubstituted phenyl, the substituents being identical or different, and where suitable phenyl substituents are: fluorine, chlorine, nitro, cyano, carboxyl, methoxycarbonyl, ethoxycarbonyl, methyl, ethyl, methoxy, ethoxy, propargyloxy, trifluoromethyl, 2-chloroethyl, 3-chloropropyl, methylthio, ethylthio, trifluoromethoxy, trifluoromethylthio, phenyl, methylsulphonyl, trifluoromethylsulphonyl; dimethylamino, diethylamino, and furthermore in each case optionally mono-, di- or trisubstituted pyridyl, benzothiazolyl or benzoxazolyl, the substituents being identical or different, and where suitable substituents which may be mentioned are nitro, chlorine, cyano, trifluoromethyl, methyl, ethyl, methoxy, ethoxy and trifluoromethoxy, or represents the group

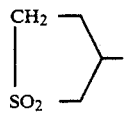

and their salts, excluding the compounds excluded from the formula (I).

Some of the compounds of the formula (I) which can be used according to the invention have not been described previously, for example the substituted pyrazolin-5-one derivatives of the formula (Ia)

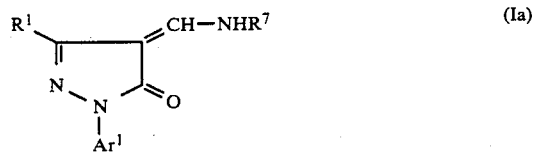

in which

R¹ represents hydrogen, alkyl, cycloalkyl, halogenoalkyl, in each case optionally substituted alkenyl or alkinyl, where suitable substituents are unsubstituted phenyl or mono-, di- or trisubstituted phenyl, the substituents being identical or different, and where suitable phenyl substituents are the aryl substituents listed under Ar; R¹ furthermore represents halogenoalkenyl, alkoxy, alkoxyalkyl, alkylthioalkyl, alkylsulphonylalkyl, alkylsulphinylalkyl, alkoxycarbonylalkyl or dialkoxy(thio)phosphoryl-alkyl, in each case optionally substituted aryl, aralkyl, aryloxyalkyl or arylthioalkyl or represents an optionally substituted heterocycle or heterocyclylalkyl or the groupings —NH—CO—R¹⁰ or —CO—O—R¹¹, wherein R¹⁰ and R¹¹, in each case independently of one another, represent alkyl or aryl, R⁷ represents alkyl, halogenoalkyl, alkenyl, halogenoalkenyl, alkoxyalkyl, optionally substituted aralkyl or optionally substituted aryl and Ar¹ represents substituted aryl, an optionally substituted and/or optionally anellated heterocycle or the group

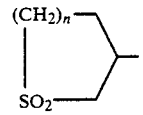

where n represents the numbers 1 or 2, and their salts, excluding the compounds 1-(4-bromophenyl)-3-methyl-4-methylamino-methylidene-pyrazolin-5-one [cf. Alam, L.V.; Kvitko, J. Ya.; El'tsov, A.V.; Zh. Org. Khim. 1977, 13 (4), 863–8] and 1-(4-chlorophenyl)-4-[(4-fluorophenylamino)-methylene]-3-methyl-pyrazolin-5-one [cf. Kreutzberger, A. and Kolter, K., Arch. Pharm., 319, 10, 865–871, 1986)] are new.

In addition, the new substituted pyrazolin-5-one derivatives of the formula (Ib)

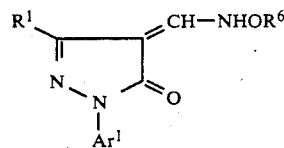

in which

R¹ represents hydrogen, alkyl, cycloalkyl, halogenoalkyl, in each case optionally substituted alkenyl or alkinyl, halogenoalkenyl, alkoxy, alkoxyalkyl, alkylthioalkyl, alkylsulphonylalkyl, alkylsulphinylalkyl, alkoxycarbonylalkyl, dialkoxy(thio)phosphorylalkyl, in each case optionally substituted aryl, aralkyl, aryloxyalkyl or arylthioalkyl or an optionally substituted heterocycle, or heterocyclylalkyl or the groupings —NH—CO—R¹⁰ or —CO—O—R¹¹, wherein R$^{10}$ and R$^{11}$, in each case independently of one another, represent alkyl or aryl, R$^6$ represents hydrogen, alkyl, halogenoalkyl, alkenyl, halogenoalkenyl or optionally substituted aralkyl, and Ar$^1$ represents substituted aryl, an optionally substituted and/or optionally anellated heterocycle or the group

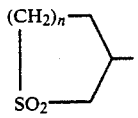

where n represents the numbers 1 or 2, and their salts, have been found.

The substituted pyrazolin-5-one derivatives of the formula (Ic)

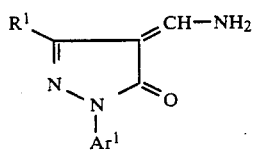

in which

R$^1$ represents hydrogen, alkyl, cycloalkyl, halogenoalkyl, in each case optionally substituted alkenyl or alkinyl, halogenoalkenyl, alkoxy, alkoxyalkyl, alkylthioalkyl, alkylsulphonylalkyl, alkylsulphinylalkyl, alkoxycarbonylalkyl, dialkoxy(thio)phosphorylalkyl, in each case optionally substituted aryl, aralkyl, aryloxyalkyl or arylthioalkyl or an optionally substituted heterocycle, or heterocyclylalkyl or the groupings —NH—CO—R$^{10}$ or —CO—O—R$^{11}$, wherein R$^{10}$ and R$^{11}$, in each case independently of one another, represent alkyl or aryl, Ar$^1$ represents substituted aryl, an optionally substituted and/or optionally anellated heterocycle or the group

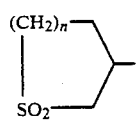

where n represents the numbers 1 or 2, and their salts, excluding the compounds 4-aminomethylene-1-(2-ethyl-phenyl)-3-methyl-pyrazolin-5-one [cf. Kreutzberger, A. and Kolter, K.; Arch. Pharm. 318, 89–91 (1985)] and 4-aminomethylene-1-(4-chlorophenyl)-3-methyl-pyrazolin-5-one [cf. Kreutzberger, A. and Kolter, K.; Arch. Pharm., 319, 865–871 (1986)], are also new.

The substituted pyrazolin-5-one derivatives of the formula (Id)

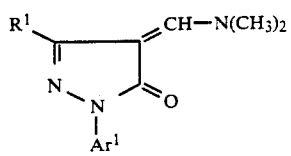

in which

R$^1$ represents hydrogen, alkyl, cycloalkyl, halogenoalkyl, in each case optionally substituted alkenyl or alkinyl, halogenoalkenyl, alkoxy, alkoxyalkyl, alkylthioalkyl, alkylsulphonylalkyl, alkylsulphinylalkyl, alkoxycarbonylalkyl, dialkoxy(thio)phosphorylalkyl, in each case optionally substituted aryl, aralkyl, aryloxyalkyl or arylthioalkyl or an optionally substituted heterocycle, or heterocyclylalkyl or the groupings —NH—CO—R$^{10}$ or —CO—O—R$^{11}$, wherein R$^{10}$ and R$^{11}$, in each case independently of one another, represent alkyl or aryl, and Ar$^1$ represents substituted aryl, an optionally substituted and/or optionally anellated heterocycle or the group

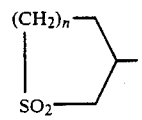

where n represents the numbers 1 or 2, and their salts have also not previously been described, excluding the compounds 1-(4-nitrophenyl)-3-methyl-4-N,N-dimethylamino-methylidene-pyrazolin-5-one, 1-(4-chlorophenyl)-3-(2-nitrophenyl)-4-N,N-dimethylamino-methylidene-pyrazolin-5-one and 1-(3-trifluoromethylphenyl)-3-phenyl-4-N,N-dimethylaminomethylidene-pyrazolin-5-one.

The substituted pyrazolin-5-one derivatives of the formula (If)

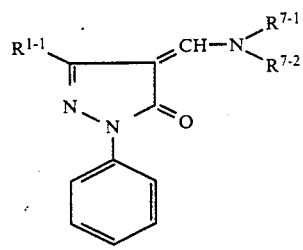

in which

R$^{11}$ represents alkoxy, dialkoxy(thio)phosphoryl-alkyl, optionally substituted alkenyl, substituted aryl, optionally substituted aralkyl, in each case optionally substituted furanylalkyl or thienylalkyl, an optionally substituted heterocycle or the group —NH—CO—R$^{10}$, where R$^{10}$ represents alkyl or phenyl, R$^{7\text{-}1}$ represents hydrogen, alkyl, halogenoalkyl, alkenyl, halogenoalkenyl, alkoxyalkyl, optionally substituted aralkyl or optionally substituted aryl and R$^{7\text{-}2}$ represents hydrogen or methyl, have also not previously been described, with the compound 1-phenyl-3-(4-methoxyphenyl)-4-N,N-dimethylaminomethylidene-pyrazolin-5-one (British Patent No. 887,509) being excluded.

It has furthermore been found that the new substituted pyrazolin-5-one derivatives of the formula (Ia)

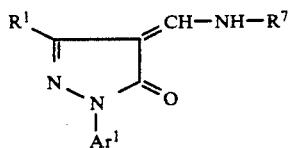

in which
$R^1$, $Ar^1$ and $R^7$ have the meanings given above,
excluding the compounds already mentioned previously under the formula (Ia),
are obtained by reacting amines of the formula (II)

 (II)

in which
$R^7$ has the meanings given above,
(α) with the new 4-(dimethylamino-methylidene)-pyrazolin-5-one derivatives of the formula (Id)

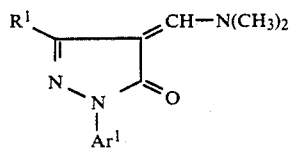

in which
$R^1$ and $Ar^1$ have the meanings given above,
which likewise belong to the invention, if appropriate in the presence of diluents or
(β) with 4-formyl-pyrazolin-5-one derivatives of the formula (IV)

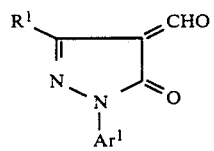

in which
$R^1$ and $Ar^1$ have the meanings given above,
if appropriate in the presence of diluents.

Further, it has been found that the new substituted pyrazolin-5-one derivatives of the formula (Ib)

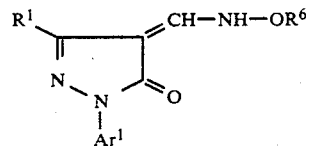

in which
$R^1$, $R^6$ and $Ar^1$ have the meanings given above,
are obtained by reacting the 4-(dimethylaminomethylidene)-pyrazolin-5-one derivatives according to the invention, of the formula (Id)

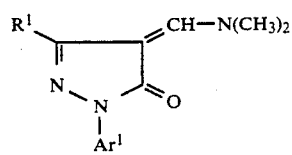

in which
$R^1$ and $Ar^1$ have the meanings given above,
with hydroxylamines or the corresponding hydrochlorides of the formula (V)

$H_2N-OR^6$ (V)

in which
$R^6$ has the meanings given above,
if appropriate in the presence of diluents.

Furthermore, it has been found that the new substituted pyrazolin-5-one derivatives of the formula (Ic)

in which
$R^1$ and $Ar^1$ have the meanings given above,
excluding the compounds excluded from the formula (Ib)
are obtained by reacting
(α) the new 4-(dimethylaminomethylidene)-pyrazolin-5-one derivatives belonging to the invention, of the formula (Id)

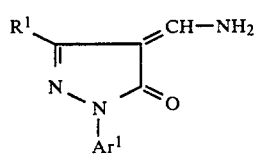

in which
$R^1$ and $Ar^1$ have the meanings given above,
with ammonia, if appropriate in the presence of diluents, or
(β) pyrazolin-5-ones of the formula (VI)

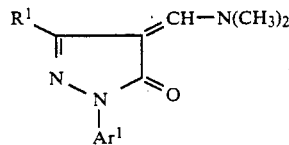

in which
$R^1$ and $Ar^1$ have the meanings given above,
with 1,3,5-triazine of the formula (VII)

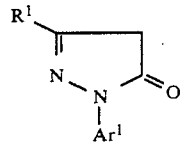

if appropriate in the presence of diluents.

Furthermore, it has been found that the new substituted pyrazolin-5-one derivatives of the formula (Id)

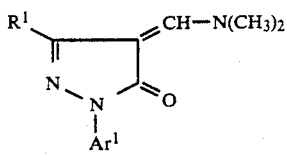  (Id)

in which
R¹ and Ar¹ have the meanings given above,
excluding the compounds 1-(4-nitro-phenyl)-3-methyl-4-N,N-dimethylamino-methylidene-pyrazolin-5-one and 1-(4-sulphophenyl)-3-methyl-4-N,N-dimethylamino-methylidene-pyrazolin-5-one, are obtained by reacting pyrazolin-5-one derivatives of the formula (VI)

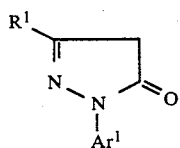  (VI)

in which
R¹ and Ar¹ have the meanings given above,
(α) with dimethylformamide in the presence of diluents at temperatures of 10° C. to 150° C. or
(β) with N,N-dimethylformamide dimethylacetal of the formula (VIII)

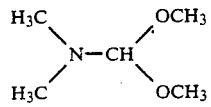  (VIII)

if appropriate in the presence of diluents, at temperatures of 10° C. to 150° C.

Furthermore, it has been found that the new substituted pyrazolin-5-one derivatives of the formula (If)

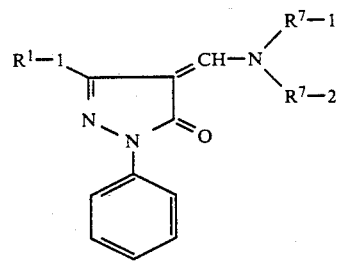  (If)

in which
R¹⁻¹, R⁷⁻¹ and R⁷⁻² have the meanings given above, are obtained by reacting amines of the formula (IIa)

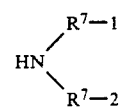  (IIa)

in which
R⁷⁻¹ and R⁷⁻² have the meanings given above,
(α) with pyrazolin-5-one derivatives of the formula (IIIa)

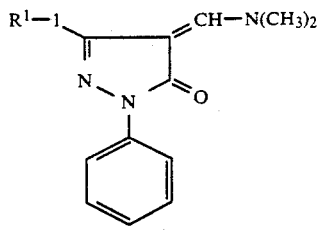  (IIIa)

in which
R¹⁻¹ has the meaning given above,
if appropriate in the presence of diluents or
(β) with 4-formyl-pyrazolin-5-one derivatives of the formula (IVb)

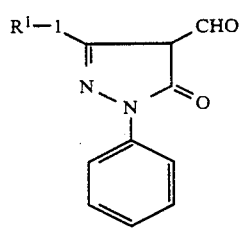  (IVb)

in which
R¹⁻¹ has the meaning given above,
if appropriate in the presence of diluents.

Furthermore, it has been found that the substituted pyrazolin-5-one derivatives of the formula (I) or (Ia), (Ib), (Ic) and (Id), in which R¹ represents the group —NH—CO—R¹⁰ with R¹⁰=alkyl or aryl, are obtained by reacting arylhydrazines of the formula (X)

  Ar¹—NH—NH₂  (X)

in which
Ar¹ has the meaning given above,
with compounds of the formula (XVI)

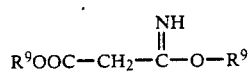  (XVI)

in which
R⁹ represents methyl or ethyl,
in a first step, if appropriate in the presence of a diluent, to give the substituted arylhydrazines of the formula (XVII)

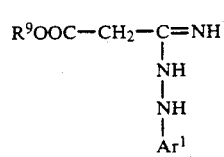  (XVII)

in which
Ar¹ and R⁹ have the meanings given above,
and reacting the compounds (XVII) in a second step [cf. J. Am. Chem. Soc. 66, 1851 (1944)] if appropriate in the presence of a diluent and in the presence of a strong base, to give the 3-aminopyrazolin-5-one derivatives of the formula (XVIII)

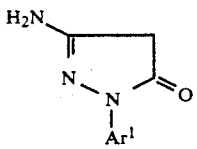

in which

Ar¹ has the meaning given above, and then acylating the compounds (XVIII) with compounds of the formula (XIX)

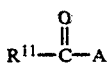

in which

R¹¹ has the meaning given above and

A represents halogen, in particular chlorine or bromine, or a radical R¹¹—CO—O—, if appropriate in the presence of an acid-binding agent and if appropriate in the presence of a diluent to give the compounds of the formula (VIa)

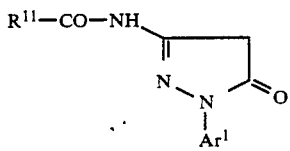

in which

Ar¹ and R¹¹ have the meanings given above, which are then reacted according to process variation (Ic/β) with 1,3,5-triazine of the formula (VII) or according to (Id/α and β) with dimethylformamide or N,N-dimethylformamide dimethylacetal of the formula (VIII) according to the reaction conditions described therein.

The substituted pyrazolin-5-one derivatives thus obtained, of the formula (Ie)

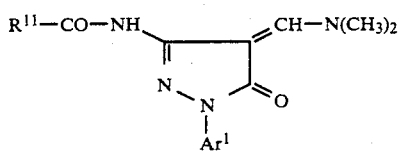

in which

R¹¹ and Ar¹ have the meaning given above, can be hydrolysed, if appropriate in the presence of a diluent and in the presence of a base suitable for the reaction conditions, which are described in the preparation of the starting substances of the formula (IV), to give compounds of the formula (IVb)

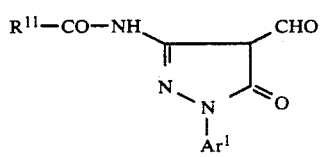

in which

R¹¹ and Ar¹ have the meanings given above, which can then be reacted further according to process variation (Ia/β) to give pyrazolin-5-ones according to the invention, of the formula (I) (cf. preparation examples).

Analogously to the processes described above, the group —NH—CO—R¹⁰ can also be introduced into the compounds of the formula (If).

As described for the compounds of the formula (I), the new substances of the formulae (Ia), (Ib), (Ic), (Id) and (If) can exist as geometric isomers (E/Z isomers) or isomeric mixtures of variable composition. Both the pure isomers and the isomeric mixtures are claimed according to the invention, as are the tautomeric compounds, as described under the formula (I).

The known compounds of the formula (I) can be prepared analogously to the abovementioned processes for the preparation of the new compounds of the formulae (Ia), (Ib), (Ic), (Id) and (If).

Thus, the compounds of the formula (I)

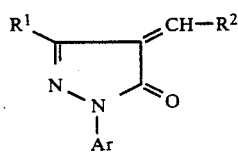

in which

R¹, R² and Ar have the abovementioned meanings, excluding the compounds excluded from the formula (I), can be obtained by reacting, for example, compounds of the formula (III)

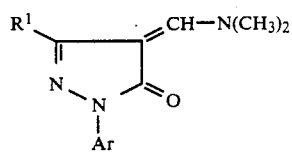

in which

R¹ and Ar have the meanings given above, or compounds of the formula (IVa)

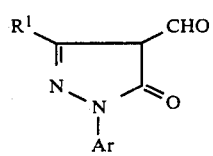

in which

R¹ and Ar have the meanings given above, in each case with amines of the formula (II)

H₂N—R⁷     (II)

in which

R⁷ has the meaning given above.

In the following, the compounds in each case already excluded in the main definition are likewise excluded in the preferred, particularly preferred and very particularly preferred ranges of the compounds of the formulae (Ia), (Ic) and (Id).

Preferred new substituted pyrazolin-5-one derivatives of the formula (Ia) are those in which R¹ represents hydrogen, straight-chain or branched alkyl with 1 to 8 carbon atoms; cycloalkyl with 3 to 7 carbon atoms, halogenoalkyl with 1 to 4 carbon atoms and 1 to 9 identical or different halogen atoms, such as in particular fluorine and chlorine atoms, in each case optionally substituted alkenyl or alkinyl with in each case 2 to 6 carbon atoms, where suitable substituents are unsubstituted phenyl or mono-, di- or trisubstituted phenyl, the substituents being identical or different, and where suitable phenyl substituents are the aryl substituents listed under $Ar^1$; $R^1$ furthermore represents halogenoalkenyl with 2 to 6 carbon atoms and 1 to 10 identical or different halogen atoms, such as in particular fluorine and chlorine, alkoxy with 1 to 8 carbon atoms, alkoxyalkyl with in each case 1 to 8 carbon atoms in the individual alkyl parts, alkylthioalkyl, alkylsulphonylalkyl or alkylsulphinylalkyl with in each case 1 to 8 carbon atoms in the individual alkyl parts, alkoxycarbonylalkyl with 1 to 4 carbon atoms in the alkoxy part and 1 to 4 carbon atoms in the alkyl part, a 5- or 6-membered, optionally fluorine-, chlorine-, methyl- and/or ethyl-substituted heterocycle, in particular furanyl or thienyl; furanylmethyl, thienylmethyl or $R^1$ furthermore represents aryl, arylalkyl, aryloxyalkyl or arylthioalkyl in each case optionally mono-, di-, tri-, tetra- or pentasubstituted in the aryl part by identical or different substituents and with in each case 6 to 10 carbon atoms in the aryl part and, where appropriate, 1 to 4 carbon atoms in the alkyl part, where suitable aryl substituents are the aryl substituents listed in $Ar^1$, $R^1$ furthermore represents the groupings —NH—CO—$R^{10}$ or —CO—O—$R^{11}$, wherein $R^{10}$ and $R^{11}$, in each case independently of one another, represent $C_1$–$C_4$-alkyl or phenyl;

$R^7$ represents straight-chain or branched alkyl with 1 to 8 carbon atoms, halogenoalkyl with 1 to 6 carbon atoms and 1 to 12 identical or different halogen atoms, such as in particular fluorine and chlorine atoms, straight-chain or branched alkenyl with 2 to 12 carbon atoms, halogenoalkenyl with 2 to 6 carbon atoms and 1 to 10 identical or different halogen atoms, such as in particular fluorine and chlorine atoms, alkoxyalkyl with in each case 1 to 8 carbon atoms in the alkoxy and alkyl part, optionally mono- or polysubstituted aralkyl with 1 to 4 carbon atoms in straight-chain or branched alkyl part and 6 to 10 carbon atoms in the aryl part, the substituents being identical or different, optionally mono-, di-, tri-, tetra- or pentasubstituted aryl with 6 to 10 carbon atoms, the substituents being identical or different, and where suitable aryl substituents are in each case: halogen, straight-chain or branched alkyl with 1 to 4 carbon atoms and dialkylamino with in each case 1 to 4 carbon atoms in the alkyl part, $C_1$–$C_4$-alkoxy or halogeno-$C_1$–$C_4$-alkyl, $Ar^1$ represents mono- or polysubstituted aryl with 6 to 10 carbon atoms, in particular phenyl or naphthyl, the substituents being identical or different, and where suitable aryl substituents are: halogen; nitro; cyano; carboxyl; alkoxycarbonyl with 1 to 4 carbon atoms, $C_1$–$C_4$-alkyl, $C_1$–$C_4$-alkoxy or $C_1$–$C_4$-alkylthio; $C_3$–$C_6$-alkinoxy; halogeno-($C_1$–$C_4$)-alkyl, halogeno-($C_1$–$C_4$)-alkoxy or halogeno-($C_1$–$C_4$)-alkylthio with in each case 1 to 9 identical or different halogen atoms; phenyl; $C_1$–$C_4$-alkylsulphonyl and halogeno-($C_1$–$C_4$)-alkylsulphonyl with in each case 1 to 9 identical or different halogen atoms; and di-($C_1$–$C_4$)-alkylamino; $Ar^1$ further represents an optionally substituted and/or optionally anellated 6-membered, aromatic heterocycle, which contains at least one nitrogen atom and where suitable substituents are the aryl substituents listed in $Ar^1$ above, or represents the group

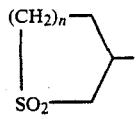

where n represents the numbers 1 or 2.

Particularly preferred new compounds of the formula (Ia) are those in which $R^1$ represents hydrogen, straight-chain or branched alkyl with 1 to 4 carbon atoms, cycloalkyl with 3 to 6 carbon atoms, halogenoalkyl with 1 to 3 carbon atoms and 1 to 7 identical or different halogen atoms, such as in particular fluorine and chlorine atoms, in each case optionally substituted alkenyl or alkinyl with in each case 2 to 4 carbon atoms, where suitable substituents are unsubstituted phenyl or mono-, di- or trisubstituted phenyl, the substituents being identical or different, and where suitable phenyl substituents are the aryl substituents listed under $Ar^1$; $R^1$ furthermore represents halogenoalkenyl with 3 or 4 carbon atoms and 1 to 5 identical or different halogen atoms, such as in particular fluorine and chlorine, alkoxy with 1 to 4 carbon atoms, alkoxyalkyl with in each case 1 to 4 carbon atoms in the individual alkyl parts, alkylthioalkyl, alkylsulphonylalkyl or alkylsulphinylalkyl with in each case 1 to 4 carbon atoms in the individual alkyl parts, alkoxycarbonylalkyl with 1 or 2 carbon atoms in the alkoxy part and 1 or 2 carbon atoms in the alkyl part, a 5- or 6-membered, optionally fluorine-, chlorine-, methyl- and/or ethyl-substituted heterocycle, in particular furanyl or thienyl; furanylmethyl, thienylmethyl or $R^1$ furthermore represents in each case optionally mono-, di-, tri-, tetra- or pentasubstituted phenyl, naphthyl, benzyl, phenylethyl, phenoxymethyl, phenoxyethyl, phenylthiomethyl or phenylthioethyl, the substituents being identical or different, and where suitable phenyl substituents are in each case the phenyl substituents listed under $Ar^1$; $R^1$ furthermore represents the groupings —NH—CO—$R^{10}$ or —CO—O$R^{11}$, wherein $R^{10}$ and $R^{11}$, in each case independently of one another, represent $C_1$–$C_4$-alkyl or phenyl, $R^7$ represents straight-chain or branched alkyl with 1 to 4 carbon atoms; halogenoalkyl with 1 to 4 carbon atoms and 1 to 9 identical or different halogen atoms, such as in particular fluorine and chlorine atoms; straight-chain or branched alkenyl with 2 to 6 carbon atoms; halogenoalkyl with 2 to 4 carbon atoms and 1 to 7 identical or different halogen atoms, such as in particular fluorine and chlorine atoms; alkoxyalkyl with in each case 1 to 4 carbon atoms in the alkoxy or alkyl part; optionally mono-, di-, tri-, tetra- or pentasubstituted phenylalkyl with 1 to 3 carbon atoms in the straight-chain or branched alkyl part, the substituents being identical or different, or optionally mono-, di-, tri-, tetra- or pentasubstituted phenyl, the substituents being identical or different, and where suitable phenyl substituents are in each case: halogen, straight-chain or branched alkyl with 1 or 2 carbon atoms and dialkylamino with in each case 1 or 2 carbon atoms in the alkyl part, $C_1$-$C_2$-alkoxy or halogeno-$C_1$-$C_2$-alkyl;

$Ar^1$ represents mono-, di-, tri-, tetra- or pentasubstituted phenyl, the substituents being identical or different, and where suitable phenyl substituents are: halogen; nitro; cyano; carboxyl, alkoxycarbonyl with 1 to 3 carbon atoms; $C_1$-$C_3$-alkyl, $C_1$-$C_3$-alkoxy; $C_1$-$C_3$-alkylthio; $C_3$-$C_4$-alkinoxy; halogeno-($C_1$-$C_3$)-alkyl or halogeno-($C_1$-$C_4$)-alkoxy or halogeno-($C_1$-$C_4$)-alkylthio with in each case 1 to 7 identical or different halogen atoms; phenyl; $C_1$-$C_3$-alkylsulphonyl and halogeno-($C_1$-$C_3$)-alkylsulphonyl with in each case 1 to 7 identical or different halogen atoms; and di-($C_1$-$C_3$)-alkylamino; $Ar^1$ further represents an optionally substituted and/or optionally anellated 6-membered, aromatic heterocycle, which contains at least one nitrogen atom and where suitable substituents are the phenyl substituents listed in $Ar^1$ above, or represents the group

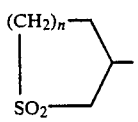

where
n represents the numbers 1 or 2.

Very particularly preferred new compounds of the formula (Ia) are those in which $R^1$ represents hydrogen, methyl, ethyl, n-propyl, i-propyl, n-butyl, i-butyl, tert.-butyl, cyclopropyl, cyclohexyl, trifluoromethyl, vinyl, allyl, butenyl, propargyl, 2-phenylvinyl, chloroallyl, methoxy, ethoxy, methoxymethyl, ethoxymethyl, methylthiomethyl, ethylthiomethyl, methylsulphonylmethyl, metnylsulphonylethyl, ethylsulphonylmethyl, ethylsulphonylethyl, methylsulphinylmethyl, methylsulphinylethyl, ethylsulphinylmethyl, ethylsulphinylethyl, furanyl, pyridyl, thienyl, furanylmethyl, thienylmethyl, ethoxycarbonylmethyl, methoxycarbonylmethyl, $R^1$ furthermore represents in each case optionally mono-, di- or trisubstituted phenyl, naphthyl, benzyl, phenylethyl, phenoxymethyl, phenythiomethyl, the substituents being identical or different, and where suitable phenyl substituents are in each case the phenyl substituents listed under $Ar^1$; $R^1$ furthermore represents the groupings —NH—CO—$R^{10}$ or —CO—O—$R^{11}$, wherein
$R^{10}$ and $R^{11}$, in each case independently of one another, represent methyl, ethyl or phenyl, $R^7$ represents methyl, ethyl, n-propyl, i-propyl, i-butyl, 2,2-dimethylpropyl, n-hexyl, trifluoromethyl, 2-chloroethyl, 3-chloropropyl, propenyl, methoxymethyl, methoxyethyl, methoxypropyl, ethoxymethyl, ethoxyethyl, 3-chloroallyl, α-methylbenzyl, mono-, di-, tri-, tetra- or penta-substituted phenyl, the substituents being identical or different, and where suitable phenyl substituents are: fluorine, chlorine, methyl, methoxy, ethoxy, trifluoromethyl, trifluoroethyl and dimethylamino, $Ar^1$ represents mono-, di-, tri-, tetra- or pentasubstituted phenyl, the substituents being identical or different, and where suitable phenyl substituents are: fluorine, chlorine, nitro, cyano, carboxyl, methoxycarbonyl, ethoxycarbonyl, methyl, ethyl, methoxy, ethoxy, propargyloxy, trifluoromethyl, 2-chloroethyl, 3-chloropropyl, methylthio, ethylthio, trifluoromethoxy, trifluoromethylthio, phenyl, methylsulphonyl, trifluoromethylsulphonyl; dimethylamino, diethylamino; $Ar^1$ furthermore represents in each case mono-, di- or trisubstituted pyridyl, benzothiazolyl and benzoxazolyl, the substituents being identical or different, where substituents which may be mentioned are nitro, chlorine, cyano, methyl, ethyl, methoxy, ethoxy, trifluoromethoxy and trifluoromethyl, or represents the group

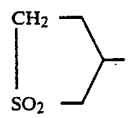

The following pyrazolin-5-one derivatives of the general formula (Ia) may be mentioned individually in addition to the compounds mentioned in the preparation examples:

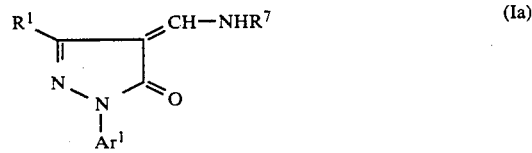

TABLE 1

| $R^1$ | $R^7$ | $Ar^1$ |
|---|---|---|
| ⌬-OCF₃ | CH₃ | F-⌬ |
| ⌬-OCF₃ | C₂H₅ | F-⌬ |
| ⌬-OCF₃ (meta CF₃O) | CH₃ | F-⌬ |
| ⌬-OCF₃ | CH₃ | F-⌬-F |
| ⌬-OCF₃ (meta CF₃O) | CH₃ | F-⌬-F |

TABLE 1-continued

| R¹ | R⁷ | Ar¹ |
|---|---|---|
| 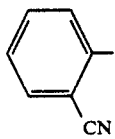 (2-CN-phenyl) | CH₃ | 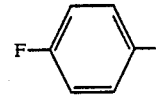 (4-F-phenyl) |
| 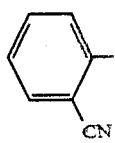 (2-CN-phenyl) | CH₃ | 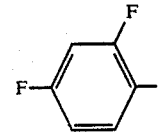 (2,4-diF-phenyl) |
| 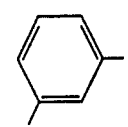 (3-CN-phenyl) | CH₃ | 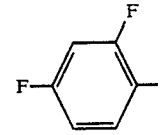 (2,4-diF-phenyl) |
| 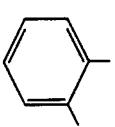 (2-SCF₃-phenyl) | CH₃ | 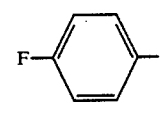 (4-F-phenyl) |
| 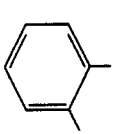 (2-SCF₃-phenyl) | CH₃ | 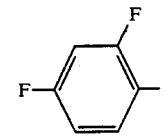 (2,4-diF-phenyl) |
| 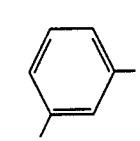 (3-CF₃S-phenyl) | CH₃ | 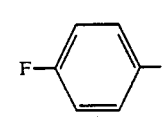 (4-F-phenyl) |
| 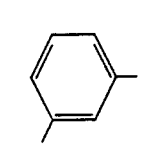 (3-CF₃S-phenyl) | CH₃ | 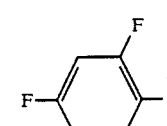 (2,4-diF-phenyl) |
| 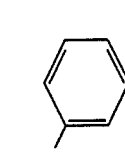 (3-CF₃O₂S-phenyl) | CH₃ | 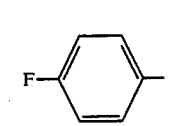 (4-F-phenyl) |
| 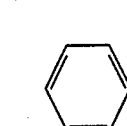 (3-CF₃O₂S-phenyl) | CH₃ | 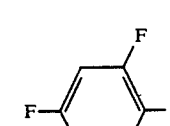 (2,4-diF-phenyl) |
| 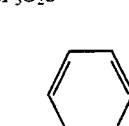 (3-CH₃O₂S-phenyl) | CH₃ | 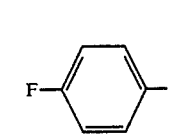 (4-F-phenyl) |

TABLE 1-continued

| R¹ | R⁷ | Ar¹ |
|---|---|---|
| 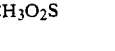 (3-CH₃O₂S-phenyl) | CH₃ | (2,4-diF-phenyl) |
| 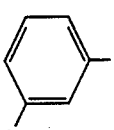 (3-CH₃O₂C-phenyl) | CH₃ | (4-F-phenyl) |
| 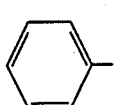 (3-CH₃O₂C-phenyl) | CH₃ | (2,4-diF-phenyl) |
| 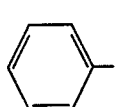 (3-(CH₃)₂N-phenyl) | CH₃ | (4-F-phenyl) |
| 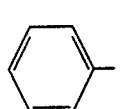 (3-(CH₃)₂N-phenyl) | CH₃ | (2,4-diF-phenyl) |
| 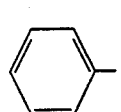 (phenyl) | CH₃ | HC≡C—CH₂O— 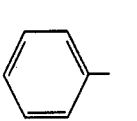 (2-Cl-4-F-phenyl) |
|  (3-CF₃-phenyl) | CH₃ | HC≡C—CH₂O— (2-Cl-4-F-phenyl) |
|  (3-Cl-phenyl) | CH₃ | HC≡C—CH₂O— (2-Cl-4-F-phenyl) |
| 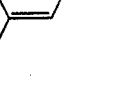 (2-pyridyl) | CH₃ | 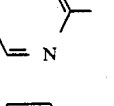 (4-F-phenyl) |
| 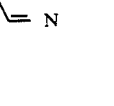 (2-pyridyl) | CH₃ |  (2,4-diF-phenyl) |

TABLE 1-continued

| R¹ | R⁷ | Ar¹ |
|---|---|---|
| 3-pyridyl | CH₃ | 4-F-phenyl |
| 3-pyridyl | CH₃ | 3,4-F₂-phenyl |
| 3-pyridyl | CH₃ | 4-F-phenyl |
| 4-pyridyl | CH₃ | 3,4-F₂-phenyl |
| 2-furyl | CH₃ | 4-F-phenyl |
| 2-furyl | CH₃ | 3,4-F₂-phenyl |
| 2-thienyl | CH₃ | 4-F-phenyl |
| 2-thienyl | CH₃ | 3,4-F₂-phenyl |
| 2-F-phenyl | CH₃ | 3,4-F₂-phenyl |
| 3-CF₃-phenyl | CH₃ | 4-CF₃-phenyl |
| 3-Cl-phenyl | CH₃ | 4-CF₃-phenyl |
| 3-Cl-phenyl | CH₃ | 4-CF₃-phenyl |
| phenyl-CH=CH− | CH₃ | 4-F-phenyl |
| phenyl-CH=CH− | CH₃ | 3,4-F₂-phenyl |
| 3-CF₃-phenyl-CH=CH− | CH₃ | 4-F-phenyl |
| 3-CF₃-phenyl-CH=CH− | CH₃ | 3,4-F₂-phenyl |
| 1-naphthyl | CH₃ | 4-F-phenyl |
| 1-naphthyl | CH₃ | 3,4-F₂-phenyl |

Preferred new substituted pyrazolin-5-one derivatives of the formula (Ib) are those in which
R¹ represents hydrogen, straight-chain or branched alkyl with 1 to 8 carbon atoms, cycloalkyl with 3 to 7 carbon atoms, halogenoalkyl with 1 to 4 carbon atoms and 1 to 9 identical or different halogen atoms, such as in particular fluorine and chlorine atoms, in each case optionally substituted alkenyl or alkinyl with in each case 2 to 6 carbon atoms, where suitable substituents are unsubstituted phenyl or mono-, di- or trisubstituted phenyl, the substituents being identical or different, and where suitable phenyl substituents are the aryl substituents listed under Ar¹; halogenoalkenyl with 2 to 6 carbon atoms and 1 to 10 identical or different halogen atoms, such as in particular fluorine and chlorine, alkoxy with 1 to 8 carbon atoms, alkoxyalkyl with in each case 1 to 8 carbon atoms in the individual alkyl parts, alkylthioalkyl, alkylsulphonylalkyl or alkylsulphinylalkyl with in each case 1 to 8 carbon atoms in the individual alkyl parts, alkoxycarbonylalkyl with 1 to 4 carbon atoms in the alkoxy part and 1 to 4 carbon atoms in the alkyl part, a 5- or 6-membered, optionally fluorine-, chlorine-, methyl- and/or ethyl-substituted heterocycle, in particular furanyl or thienyl; furanylmethyl or thienylmethyl or $R^1$ furthermore represents in each case optionally mono-, di-, tri-, tetra- or pentasubstituted aryl, arylalkyl, aryloxyalkyl or arylthioalkyl substituted in the aryl part by identical or different substituents, with in each case 6 to 10 carbon atoms in the aryl part and optionally 1 to 4 carbon atoms in the alkyl part, where suitable aryl substituents are the aryl substituents listed under $Ar^1$; $R^1$ furthermore represents the groupings $-NH-CO-R^{10}$ or $-CO-O-R^{11}$, wherein $R^{10}$ and $R^{11}$, in each case independently of one another, represent $C_1-C_4$-alkyl or phenyl, $R^6$ represents hydrogen, straight-chain or branched alkyl with 1 to 8 carbon atoms, halogenoalkyl with 1 to 6 carbon atoms and 1 to 12 identical or different halogen atoms, such as in particular fluorine and chlorine atoms, straight-chain or branched alkenyl with 2 to 12 carbon atoms, halogenoalkenyl with 2 to 6 carbon atoms and 1 to 10 identical or different halogen atoms, such as in particular fluorine and chlorine atoms, optionally mono- or polysubstituted aralkyl with 1 to 4 carbon atoms in the alkyl part and 6 to 10 carbon atoms in the aryl part, the substituents being identical or different, and where suitable aryl substituents are halogen, $C_1-C_4$-alkyl, halogeno-$C_1-C_4$-alkyl and nitro, and $Ar^1$ represents mono- or polysubstituted aryl with 6 to 10 carbon atoms, in particular phenyl or naphthyl, the substituents being identical or different, and where suitable aryl substituents are: halogen; nitro; cyano; carboxyl; alkoxycarbonyl with 1 to 4 carbon atoms, $C_1-C_4$-alkyl, $C_1-C_4$-alkoxy or $C_1-C_4$-alkylthio; $C_3-C_6$-alkinoxy; halogeno-$(C_1-C_4)$-alkyl, halogeno-$(C_1-C_4)$-alkoxy or halogeno-$(C_1-C_4)$-alkylthio with in each case 1 to 9 identical or different halogen atoms; phenyl; $C_1-C_4$-alkylsulphonyl and halogeno-$(C_1-C_4)$-alkylsulphonyl with in each case 1 to 9 identical or different halogen atoms; and di-$(C_1-C_4)$-alkylamino; $Ar^1$ further represents an optionally substituted and/or optionally anellated 6-membered, aromatic heterocycle, which contains at least one nitrogen atom and where suitable substituents are the aryl substituents listed in $Ar^1$ above, or represents the group

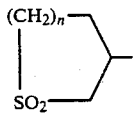

where n represents the numbers 1 or 2.

Particularly preferred new compounds of the formula (Ib) are those in which $R^1$ represents hydrogen, straight-chain or branched alkyl with 1 to 4 carbon atoms, cycloalkyl with 3 to 6 carbon atoms, halogenoalkyl with 1 to 3 carbon atoms and 1 to 7 identical or different halogen atoms, such as in particular fluorine and chlorine atoms, in each case optionally substituted alkenyl or alkinyl with in each case 2 to 4 carbon atoms, where suitable substituents are unsubstituted phenyl or mono-, di- or trisubstituted phenyl, the substituents being identical or different, and where suitable phenyl substituents are the aryl substituents listed under $Ar^1$; $R^1$ furthermore represents halogenoalkenyl with 3 or 4 carbon atoms and 1 to 5 identical or different halogen atoms, such as in particular fluorine and chlorine, alkoxy with 1 to 4 carbon atoms, alkoxyalkyl with in each case 1 to 4 carbon atoms in the individual alkyl parts, alkylthioalkyl, alkylsulphonylalkyl or alkylsulphinylalkyl with in each case 1 to 4 carbon atoms in the individual alkyl parts, alkoxycarbonylalkyl with 1 or 2 carbon atoms in the alkoxy part and 1 or 2 carbon atoms in the alkyl part, a 5- or 6-membered, optionally fluorine-, chlorine-, methyl- and/or ethyl-substituted heterocycle, in particular furanyl or thienyl; furanylmethyl, thienylmethyl or $R^1$ furthermore represents in each case optionally mono-, di-, tri-, tetra- or pentasubstituted phenyl, naphthyl, benzyl, phenylethyl, phenoxymethyl, phenoxyethyl, phenylthiomethyl or phenylthioethyl, the substituents being identical or different, and where suitable phenyl substituents are in each case the phenyl substituents listed under $Ar^1$; $R^1$ furthermore represents the groupings $-NH-CO-R^{10}$ or $-CO-OR^{11}$, wherein $R^{10}$ and $R^{11}$, in each case independently of one another, represent $C_1-C_4$-alkyl or phenyl, $R^6$ represents hydrogen, straight-chain or branched alkyl with 1 to 6 carbon atoms, halogenoalkyl with 1 to 3 carbon atoms and 1 to 7 identical or different halogen atoms, such as in particular fluorine and chlorine atoms, straight-chain or branched alkenyl with 2 to 6 carbon atoms, halogenoalkenyl with 2 or 3 carbon atoms and 1 to 5 identical or different halogen atoms, such as in particular fluorine and chlorine atoms, optionally mono-, di-, tri-, tetra- or pentasubstituted phenylalkyl with 1 to 3 carbon atoms in the alkyl part, the substituents being identical or different, and where suitable phenyl substituents are halogen, $C_1-C_2$-alkyl, halogeno-$C_1-C_2$-alkyl and nitro, and $Ar^1$ represents mono-, di-, tri-, tetra- or pentasubstituted phenyl, the substituents being identical or different, and where suitable phenyl substituents are: halogen; nitro; cyano; carboxyl; alkoxycarbonyl with 1 to 3 carbon atoms; $C_1-C_3$-alkyl, $C_1-C_3$-alkoxy or $C_1-C_3$-alkylthio; $C_3-C_4$-alkinoxy; halogeno-$(C_1-C_3)$-alkyl or halogeno-$(C_1-C_4)$-alkoxy or halogeno-$(C_1-C_4)$-alkylthio with in each case 1 to 7 identical or different halogen atoms; phenyl; $C_1-C_3$-alkylsulphonyl and halogeno-$(C_1-C_3)$-alkylsulphonyl with in each case 1 to 7 identical or different halogen atoms; and di-$(C_1-C_3)$-alkylamino; $Ar^1$ further represents an optionally substituted and/or optionally anellated 6-membered, aromatic heterocycle, which contains at least one nitrogen atom and where suitable substituents are the phenyl substituents listed in $Ar^1$ above, or represents the group

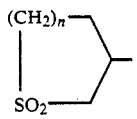

where n represents the numbers 1 or 2.

Very particularly preferred new compounds of the (Ib) are those in which $R^1$ represents hydrogen, methyl, ethyl, n-propyl, i-propyl, n-butyl, i-butyl, tert.-butyl, cyclopropyl, cyclohexyl, trifluoromethyl, vinyl, allyl, butenyl, propargyl, 2-phenylvinyl, chloroallyl, methoxy, ethoxy, methoxymethyl, ethoxymethyl, methylthiomethyl, ethylthiomethyl, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, furanyl, pyridyl, thienyl, furanylmethyl, thienylmethyl, ethoxycarbonylmethyl, methoxycarbonylmethyl, $R^1$ furthermore represents in each case optionally mono-, di- or trisubstituted phenyl, naphthyl, benzyl, phenylethyl, phenoxymethyl, phenylthiomethyl, the substituents being identical or different, and where suitable phenyl substituents are in each case the phenyl substituents listed under $Ar^1$; $R^1$ furthermore represents the groupings —NH—CO—$R^{10}$ or —CO—O—$R^{11}$, wherein $R^{10}$ and $R^{11}$, in each case independently of one another, represent methyl, ethyl or phenyl, $R^6$ represents hydrogen, methyl, ethyl, i-propyl, trifluoromethyl, 2-chloroethyl, 3-chloropropyl, propenyl, 3-chloroallyl, optionally mono-, di-, tri-, tetra- or pentasubstituted benzyl, the substituents being identical or different, and where suitable phenyl substituents are fluorine, chlorine, methyl, ethyl, trifluoromethyl and nitro and $Ar^1$ represents mono-, di-, tri-, tetra- or pentasubstituted phenyl, the substituents being identical or different, and where suitable phenyl substituents are: fluorine, chlorine, nitro, cyano, carboxyl, methoxycarbonyl, ethoxycarbonyl, methyl, ethyl, methoxy, ethoxy, propargyloxy, trifluoromethyl, 2-chloroethyl, 3-chloropropyl, methylthio, ethylthio, trifluoromethoxy, trifluoromethylthio, phenyl, methylsulphonyl, trifluoromethylsulphonyl; dimethylamino, diethylamino; $Ar^1$ furthermore represents in each case mono-, di- or trisubstituted pyridyl, benzothiazolyl and benzoxazolyl, the substituents being identical or different, and where suitable substituents are nitro, chlorine, cyano, methyl, ethyl, methoxy, ethoxy, trifluoromethoxy and trifluoromethyl, or represents the group

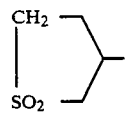

Preferred new substituted pyrazolin-5-one derivatives of the formula (Ic) are those in which $R^1$ represents hydrogen, straight-chain or branched alkyl with 1 to 8 carbon atoms, cycloalkyl with 3 to 7 carbon atoms, halogenoalkyl with 1 to 4 carbon atoms and 1 to 9 identical or different hydrogen atoms, such as in particular fluorine and chlorine atoms, in each case optionally substituted alkenyl or alkinyl with in each case 2 to 6 carbon atoms, where substituents which may be mentioned are unsubstituted phenyl or mono-, di- or trisubstituted phenyl, the substituents being identical or different, and where suitable phenyl substituents are the aryl substituents listed under $Ar^1$; halogenoalkenyl with 2 to 6 carbon atoms and 1 to 10 identical or different halogen atoms, such as in particular fluorine and chlorine, alkoxy with 1 to 8 carbon atoms, alkoxyalkyl with in each case 1 to 8 carbon atoms in the individual alkyl parts, alkylthioalkyl, alkylsulphonylalkyl or alkylsulphinylalkyl with in each case 1 to 8 carbon atoms in the individual alkyl parts, alkoxycarbonylalkyl with 1 to 4 carbon atoms in the alkoxy part and 1 to 4 carbon atoms in the alkyl part, a 5- or 6-membered, optionally fluorine-, chlorine-, methyl- and/or ethylsubstituted heterocycle, in particular furanyl or thienyl; furanylmethyl, thienylmethyl or $R^1$ furthermore represents aryl, arylalkyl, aryloxyalkyl or arylthioalkyl in each case optionally mono-, di-, tri-, tetra- or pentasubstituted in the aryl part by identical or different substituents and with in each case 6 to 10 carbon atoms in the aryl part and, where appropriate, 1 to 4 carbon atoms in the alkyl part, where suitable aryl substituents are the aryl substituents listed under $Ar^1$, $R^1$ furthermore represents the groupings —NH—CO—$R^{10}$ or —CO—O—$R^{11}$, wherein $R^{10}$ and $R^{11}$, in each case independently of one another, represent $C_1$–$C_4$-alkyl or phenyl, $Ar^1$ represents mono- or polysubstituted aryl with 6 to 10 carbon atoms, in particular phenyl or naphthyl, the substituents being identical or different, and where suitable aryl substituents are: halogen; nitro; cyano; carboxyl; alkoxycarbonyl with 1 to 4 carbon atoms, $C_1$–$C_4$-alkyl, $C_1$–$C_4$-alkoxy or $C_1$–$C_4$-alkylthio; $C_3$–$C_6$-alkinoxy; halogeno-($C_1$–$C_4$)-alkyl, halogeno-($C_1$–$C_4$)-alkoxy or halogeno-($C_1$–$C_4$)-alkylthio with in each case 1 to 9 identical or different halogen atoms; phenyl; $C_1$–$C_4$-alkylsulphonyl and halogeno-($C_1$–$C_4$)-alkylsulphonyl with in each case 1 to 9 identical or different halogen atoms and di-($C_1$–$C_4$)-alkylamino;

$Ar^1$ further represents an optionally substituted and/or optionally anellated 6-membered, aromatic heterocycle, which contains at least one nitrogen atom and where suitable substituents are the aryl substituents listed in $Ar^1$ above, or represents the group

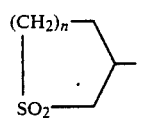

where n represents the numbers 1 or 2.

Particularly preferred new compounds of the formula (Ic) are those in which $R^1$ represents hydrogen, straight-chain or branched alkyl with 1 to 4 carbon atoms, cycloalkyl with 3 to 6 carbon atoms, halogenoalkyl with 1 to 3 carbon atoms and 1 to 7 identical or different halogen atoms, such as in particular fluorine and chlorine atoms, in each case optionally substituted alkenyl or alkinyl with in each case 2 to 4 carbon atoms, where substituents which may be mentioned are unsubstituted phenyl or mono-, di- or trisubstituted phenyl, the substituents being identical or different, and where suitable phenyl substituents are the aryl substituents listed under $Ar^1$; $R^1$ furthermore represents halogenoalkenyl with 3 or 4 carbon atoms and 1 to 5 identical or different halogen atoms, such as in particular fluorine and chlorine, alkoxy with 1 to 4 carbon atoms, alkoxyalkyl with in each case 1 to 4 carbon atoms in the individual alkyl parts, alkylthioalkyl, alkylsulphonylalkyl or alkylsulphinylalkyl with in each case 1 to 4 carbon atoms in the individual alkyl parts, alkoxycarbonylalkyl with 1 or 2 carbon atoms in the alkoxy part and 1 or 2 carbon atoms in the alkyl part, a 5- or 6-membered, optionally fluorine-, chlorine-, methyl- and/or ethyl-substituted heterocycle, in particular furanyl or thienyl; furanylmethyl, thienylmethyl or $R^1$ furthermore represents in each case optionally mono-, di-, tri-, tetra- or pentasubstituted phenyl, naphthyl, benzyl, phenylethyl, phenoxymethyl, phenoxyethyl, phenylthiomethyl or phenylthioethyl, the substituents being identical or different, and where suitable phenyl substituents are in each case the phenyl substituents listed under $Ar^1$; $R^1$ furthermore represents the groupings —NH—CO—$R^{10}$ or —CO—O$R^{11}$, wherein $R^{10}$ and $R^{11}$, in each case independently of one another, represent $C_1$-$C_4$-alkyl or phenyl, $Ar^1$ represents mono-, di-, tri-, tetra- or pentasubstituted phenyl, the substituents being identical or different, and where suitable phenyl substituents are: halogen; nitro; cyano; carboxyl; alkoxycarbonyl with 1 to 3 carbon atoms; $C_1$-$C_3$-alkyl, $C_1$-$C_3$-alkoxy; $C_1$-$C_3$-alkylthio; $C_3$-$C_4$-alkinoxy; halogeno-($C_1$-$C_3$)-alkyl, halogeno-($C_1$-$C_4$)-alkoxy or halogeno-($C_1$-$C_4$)-alkylthio with in each case 1 to 7 identical or different halogen atoms; phenyl; $C_1$-$C_3$-alkylsulphonyl and halogeno-($C_1$-$C_3$)-alkylsulphonyl with in each case 1 to 7 identical or different halogen atoms; and di-($C_1$-$C_3$)-alkylamino;

$Ar^1$ further represents an optionally substituted and/or optionally anellated 6-membered, aromatic heterocycle, which contains at least one nitrogen atom and where suitable substituents are the phenyl substituents listed in $Ar^1$ above, or represents the group

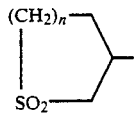

where n represents the numbers 1 or 2.

Very particularly preferred new compounds of the formula (Ic) are those in which $R^1$ represents hydrogen, methyl, ethyl, n-propyl, i-propyl, n-butyl, i-butyl, tert.-butyl, cyclopropyl, cyclohexyl, trifluoromethyl, vinyl, allyl, butenyl, propargyl, 2-phenylvinyl, chloroallyl, methoxy, ethoxy, methoxymethyl, ethoxymethyl, methylthiomethyl, ethylthiomethyl, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, furanyl, pyridyl, thienyl, furanylmethyl, thienylmethyl, ethoxycarbonylmethyl, methoxycarbonylmethyl, $R^1$ furthermore represents in each case optionally mono-, di- or trisubstituted phenyl, naphthyl, benzyl, phenylethyl, phenoxymethyl, phenylthiomethyl, the substituents being identical or different, and where suitable phenyl substituents are in each case the phenyl substituents listed under $Ar^1$; $R^1$ furthermore represents the groupings —NH—CO—$R^{10}$ or —CO—O—$R^{11}$, wherein $R^{10}$ and $R^{11}$, in each case independently of one another, represent methyl, ethyl or phenyl, $Ar^1$ represents mono-, di-, tri-, tetra- or pentasubstituted phenyl, the substituents being identical or different, and where suitable phenyl substituents are: fluorine, chlorine, nitro, cyano, carboxyl, methoxycarbonyl, ethoxycarbonyl, methyl, ethyl, methoxy, ethoxy, propargyloxy, trifluoromethyl, 2-chloroethyl, 3-chloropropyl, methylthio, ethylthio, trifluoromethoxy, trifluoromethylthio, phenyl, methylsulphonyl, trifluoromethylsulphonyl, dimethylamino and diethylamino; $Ar^1$ furthermore represents in each case mono-, di- or trisubstituted pyridyl, benzothiazolyl and benzoxazolyl, the substituents being identical or different, and where substituents which may be mentioned are nitro, chlorine, cyano, methyl, ethyl, methoxy, ethoxy, trifluoromethoxy and trifluoromethyl, or $Ar^1$ represents the group

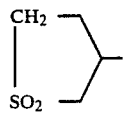

Preferred new substituted pyrazolin-5-one derivatives of the formula (Id) are those in which $R^1$ represents hydrogen, straight-chain or branched alkyl with 1 to 8 carbon atoms, cycloalkyl with 3 to 7 carbon atoms, halogenoalkyl with 1 to 4 carbon atoms and 1 to 9 identical or different halogen atoms, such as in particular fluorine and chlorine atoms, in each case optionally substituted alkenyl or alkinyl with in each case 2 to 4 carbon atoms, where substituents which may be mentioned are unsubstituted phenyl or mono-, di- or trisubstituted phenyl, the substituents being identical or different, and where suitable phenyl substituents are the aryl substituents listed under $Ar^1$; $R^1$ furthermore represents halogenoalkenyl with 2 to 6 carbon atoms and 1 to 10 identical or different halogen atoms, such as in particular fluorine and chlorine, alkoxy with 1 to 8 carbon atoms, alkoxyalkyl with in each case 1 to 8 carbon atoms in the individual alkyl parts, alkylthioalkyl, alkylsulphonylalkyl or alkylsulphinylalkyl with in each case 1 to 8 carbon atoms in the individual alkyl parts, alkoxycarbonylalkyl with 1 to 4 carbon atoms in the alkoxy part and 1 to 4 carbon atoms in the alkyl part, a 5- or 6-membered, optionally fluorine-, chlorine-, methyl- and/or ethyl-substituted heterocycle, in particular furanyl or thienyl; furanylmethyl, thienylmethyl or $R^1$ furthermore represents aryl, arylalkyl, aryloxyalkyl or arylthioalkyl in each case optionally mono-, di-, tri-, tetra- or pentasubstituted in the aryl part by identical or different substituents and with in each case 6 to 10 carbon atoms in the aryl part and, where appropriate, 1 to 4 carbon atoms in the alkyl part, where suitable aryl substituents are the aryl substituents listed under $Ar^1$, $R^1$ furthermore represents the groupings —NH—CO—$R^{10}$ or —CO—O—$R^{11}$, wherein $R^{10}$ and $R^{11}$, in each case independently of one another, represent $C_1$-$C_4$-alkyl or phenyl, $Ar^1$ represents mono- or polysubstituted aryl with 6 to 10 carbon atoms, in particular phenyl or naphthyl, the substituents being identical or different, and where suitable aryl substituents are: halogen; nitro; cyano; carboxyl; alkoxycarbonyl with 1 to 4 carbon atoms, $C_1$-$C_4$-alkyl, $C_1$-$C_4$-alkoxy or $C_1$-$C_4$-alkylthio; $C_3$-$C_6$-alkinoxy; halogeno-($C_1$-$C_4$)-alkyl, halogeno-($C_1$-$C_4$)-alkoxy or halogeno-($C_1$-$C_4$)-alkylthio with in each case 1 to 9 identical or different halogen atoms; phenyl; $C_1$-$C_4$-alkylsulphonyl and halogeno-($C_1$-$C_4$)-alkylsulphonyl with in each case 1 to 9 identical or different halogen atoms and di-($C_1$-$C_4$)-alkylamino; $Ar^1$ further represents an optionally substituted and/or optionally anellated 6-membered, aromatic heterocycle, which contains at least one nitrogen atom and where suitable substituents are the aryl substituents listed in $Ar^1$ above, or represents the group

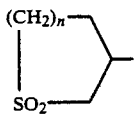

where
n represents the numbers 1 or 2.

Particularly preferred new compounds of the formula (Id) are those in which $R^1$ represents hydrogen, straight-chain or branched alkyl with 1 to 4 carbon atoms, cycloalkyl with 3 to 6 carbon atoms, halogenoalkyl with 1 to 3 carbon atoms and 1 to 7 identical or different halogen atoms, such as in particular fluorine and chlorine atoms, in each case optionally substituted alkenyl or alkinyl with in each case 2 to 4 carbon atoms, where substituents which may be mentioned are in each case unsubstituted phenyl or mono-, di- or trisubstituted phenyl, the substituents being identical or different, and where suitable phenyl substituents are the aryl substituents listed under $Ar^1$;

$R^1$ furthermore represents halogenoalkenyl with 3 or 4 carbon atoms and 1 to 5 identical or different halogen atoms, such as in particular fluorine and chlorine, alkoxy with 1 to 4 carbon atoms, alkoxyalkyl with in each case 1 to 4 carbon atoms in the individual alkyl parts, alkylthioalkyl, alkylsulphonylalkyl or alkylsulphinylalkyl with in each case 1 to 4 carbon atoms in the individual alkyl parts, alkoxycarbonylalkyl with 1 or 2 carbon atoms in the alkoxy part and 1 or 2 carbon atoms in the alkyl part, a 5- or 6-membered, optionally fluorine-, chlorine-, methyl- and/or ethyl-substituted heterocycle, in particular furanyl or thienyl; furanylmethyl, thienylmethyl or $R^1$ furthermore represents in each case optionally mono-, di-, tri-, tetra- or pentasubstituted phenyl, naphthyl, benzyl, phenylethyl, phenoxymethyl, phenoxyethyl, phenylthiomethyl or phenylthioethyl, the substituents being identical or different, and where suitable phenyl substituents are in each case the phenyl substituents listed under $Ar^1$; $R^1$ furthermore represents the groupings —NH—CO—$R^{10}$ or —CO—$OR^{11}$, wherein $R^{10}$ and $R^{11}$, in each case independently of one another, represent $C_1$-$C_4$-alkyl or phenyl, $Ar^1$ represents mono-, di-, tri-, tetra- or pentasubstituted phenyl, the substituents being identical or different, and where suitable phenyl substituents are: halogen; nitro; cyano; carboxyl; alkoxycarbonyl with 1 to 3 carbon atoms; $C_1$-$C_3$-alkyl, $C_1$-$C_3$-alkoxy; $C_1$-$C_3$-alkylthio; $C_3$-$C_4$-alkinoxy; halogeno-($C_1$-$C_3$)-alkyl, halogeno-($C_1$-$C_4$)-alkoxy or halogeno-($C_1$-$C_4$)-alkylthio with in each case 1 to 7 identical or different halogen atoms; phenyl; $C_1$-$C_3$-alkylsulphonyl and halogeno-($C_1$-$C_3$)-alkylsulphonyl with in each case 1 to 7 identical or different halogen atoms; and di-($C_1$-$C_3$)-alkylamino; $Ar^1$ further represents an optionally substituted and/or optionally anellated 6-membered, aromatic heterocycle, which contains at least one nitrogen atom and where suitable substituents are the phenyl substituents listed in $Ar^1$ above, or represents the group

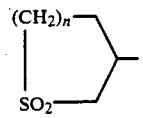

where
n represents the numbers 1 or 2.

Very particularly preferred new compounds of the formula (Id) are those in which $R^1$ represents hydrogen, methyl, ethyl, n-propyl, i-propyl, n-butyl, i-butyl, tert.-butyl, cyclopropyl, cyclohexyl, trifluoromethyl, vinyl, allyl, butenyl, propargyl, 2-phenylvinyl, chloroallyl, methoxy, ethoxy, methoxymethyl, ethoxymethyl, methylthiomethyl, ethylthiomethyl, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, furanyl, pyridyl, thienyl, furanylmethyl, thienylmethyl, ethoxycarbonylmethyl, methoxycarbonylmethyl, $R^1$ furthermore represents in each case optionally mono-, di- or trisubstituted phenyl, naphthyl, benzyl, phenylethyl, phenoxymethyl, phenylthiomethyl, the substituents being identical or different, and where suitable phenyl substituents are in each case the phenyl substituents listed under $Ar^1$; $R^1$ furthermore represents the groupings —NH—CO—$R^{10}$ or —CO—$OR^{11}$, wherein $R^{10}$ and $R^{11}$, in each case independently of one another, represent methyl, ethyl or phenyl, $Ar^1$ represents mono-, di-, tri-, tetra- or pentasubstituted phenyl, the substituents being identical or different, and where suitable phenyl substituents are: fluorine, chlorine, nitro, cyano, carboxyl, methoxycarbonyl, ethoxycarbonyl, methyl, ethyl, methoxy, ethoxy, propargyloxy, trifluoromethyl, 2-chloroethyl, 3-chloropropyl, methylthio, ethylthio, trifluoromethoxy, trifluoromethylthio, phenyl, methylsulphonyl, trifluoromethylsulphonyl, dimethylamino, diethylamino; $Ar^1$ furthermore represents in each case mono-, di- or trisubstituted pyridyl, benzothiazolyl and benzoxazolyl, the substituents being identical or different, and where substituents which may be mentioned are nitro, chlorine, cyano, methyl, ethyl, methoxy, ethoxy, trifluoromethoxy and trifluoromethyl, or represents the group

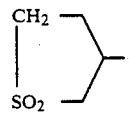

Preferred compounds of the formula (If) are those in which $R^{1-1}$ represents $C_1$–$C_8$-alkoxy, alkenyl with 2 to 6 carbon atoms, optionally substituted by unsubstituted phenyl or by mono-, di- or trisubstituted phenyl, the substituents being identical or different, and where phenyl substituents which may be mentioned are $C_1$–$C_4$-alkyl, $C_1$–$C_4$-alkoxy, halogeno-($C_1$–$C_4$)alkyl and halogeno-($C_1$–$C_4$)alkoxy, $R^{1-1}$ furthermore represents in each case mono-, di-, tri-, tetra- or pentasubstituted aryl with 6 to 10 carbon atoms, the substituents being identical or different, or optionally substituted aralkyl with 6 to 10 carbon atoms in the aryl part and 1 to 4 carbon atoms in the alkyl part, where aryl substituents which may be mentioned in each case are halogen, nitro, cyano, carboxyl, $C_1$–$C_4$-alkoxycarbonyl, $C_1$–$C_4$-alkyl, $C_1$–$C_4$-alkoxy, halogeno-($C_1$–$C_4$)-alkyl, halogeno-($C_1$–$C_4$)-alkoxy, halogeno-($C_1$–$C_4$)-alkylthio, phenyl, $C_1$–$C_4$-alkylsulphonyl, halogeno-($C_1$–$C_4$)-alkylsulphonyl and di-($C_1$–$C_4$)-alkylamino; $R^{1-1}$ further represents a 5- or 6-membered, optionally fluorine-, chlorine-, methyl- and/or ethyl-substituted heterocycle, which can contain one or two identical or different hetero atoms, in particular nitrogen, oxygen and sulphur; optionally fluorine-, chlorine-, methyl- and/or ethyl-substituted furanyl-$C_1$–$C_4$-alkyl or thienyl-$C_1$–$C_4$-alkyl, or $R^{1-1}$ furthermore represent the group —NH—CO—$R^{10}$, where $R^{10}$ represents $C_1$–$C_6$-alkyl or phenyl, $R^{7-1}$ represents hydrogen, $C_1$–$C_8$-alkyl, halogeno-$C_1$–$C_6$-alkyl, $C_2$–$C_6$-alkenyl, halogeno-$C_2$–$C_6$-alkenyl, $C_1$–$C_8$-alkoxy-$C_1$–$C_8$-alkyl, optionally mono-, di-, tri-, tetra- or pentasubstituted aralkyl with 6 to 10 carbon atoms in the aryl part and 1 to 4 carbon atoms in the alkyl part, the substituents being identical or different, or optionally mono-, di-, tri-, tetra- or pentasubstituted aryl with 6 to 10 carbon atoms, the substituents being identical or different, where aryl substituents which may be mentioned in each case are halogen, $C_1$–$C_4$-alkyl, $C_1$–$C_4$-alkoxy, halogeno-$C_1$–$C_4$-alkyl and di-($C_1$–$C_4$)-alkylamino, and $R^{7-2}$ represents hydrogen or methyl, the compound 1-phenyl-3-(4-methoxyphenyl)-4-N,N-dimethylamino-pyrazolin-5-one being excluded.

Particularly preferred compounds of the formula (If) are those in which $R^{1-1}$ represents $C_1$–$C_6$-alkoxy, alkenyl with 2 to 4 carbon atoms, optionally substituted by phenyl or optionally substituted by mono-, di- or tri-substituted phenyl with identical or different substituents, where phenyl substituents which may be mentioned are fluorine, chlorine, $C_1$–$C_3$-alkyl, $C_1$–$C_3$-alkoxy, halogeno-($C_1$–$C_3$)-alkyl and halogeno-($C_1$–$C_4$)-alkoxy; $R^{1-1}$ furthermore represents in each case mono-, di-, tri-, tetra- or pentasubstituted phenyl or naphthyl, the substituents being identical or different, or in each case optionally mono-, di-, tri-, tetra- or pentasubstituted benzyl or phenethyl, the substituents being identical or different, and where suitable phenyl substituents are in each case fluorine, chlorine, bromine, nitro, cyano, carboxyl, methoxycarbonyl, ethoxycarbonyl, methyl, ethyl, methoxy, ethoxy, halogeno-($C_1$–$C_2$)-alkyl, halogeno-($C_1$–$C_2$)-alkoxy, halogeno-($C_1$–$C_2$)-alkylthio with in each case 1 to 5 identical or different halogen atoms such as fluorine or chlorine, methylsulphonyl, ethylsulphonyl, trifluoromethylsulphonyl, dimethylamino and diethylamino; $R^{1-1}$ further represents in each case optionally fluorine-, chlorine-, methyl- and/or ethyl-substituted furanylmethyl, furanylethyl, thienylmethyl or thienylethyl, or $R^{1-1}$ furthermore represents the group —NH—CO—$R^{10}$, where $R^{10}$ represents $C_1$–$C_4$-alkyl or phenyl, $R^{7-1}$ represents hydrogen, $C_1$–$C_6$-alkyl, halogeno-$C_1$–$C_4$-alkyl, $C_2$–$C_4$-alkenyl, halogeno-$C_2$–$C_4$-alkenyl, $C_1$–$C_6$-alkoxy-$C_1$–$C_6$-alkyl, in each case optionally mono-, di-, tri-, tetra- or pentasubstituted benzyl or phenethyl, the substituents being identical or different, or optionally mono-, di-, tri-, tetra- or pentasubstituted phenyl, the substituents being identical or different, and where phenyl substituents which may be mentioned in each case are fluorine, chlorine, bromine, methyl, ethyl, halogeno-$C_1$–$C_2$-alkyl, in particular trifluoromethyl, dimethylamino and diethylamino, and $R^{7-2}$ represents hydrogen or methyl, the compound 1-phenyl-3-(4-methoxyphenyl)-4-N,N-dimethylamino-pyrazolin-5-one being excluded.

Very particularly preferred compounds of the formula (If) are those in which $R^{1-1}$ represents $C_1$–$C_4$-alkoxy, vinyl, allyl, butenyl, 2-phenylvinyl, 2-(2-trifluoromethylphenyl)vinyl, in each case mono-, di- or tri-substituted phenyl, the substituents being identical or different, or optionally mono-, di- or trisubstituted benzyl, the substituents being identical or different, where phenyl substituents which may be mentioned in each case are fluorine, chlorine, nitro, cyano, methoxycarbonyl, ethoxycarbonyl, methyl, ethyl, methoxy, trifluoromethyl, trifluoromethoxy, trifluoromethylthio, difluoromethylthio, trifluoromethylsulphonyl, methylsulphonyl, dimethylamino and diethylamino; $R^{1-1}$ furthermore represents in each case optionally fluorine-, chlorine-, methyl- and/or ethyl-substituted furanylmethyl or thienylmethyl or the group —NH—CO—$R^{10}$, where $R^{10}$ represents methyl, ethyl or phenyl, $R^{7-1}$ represents hydrogen, methyl, ethyl, n- or iso-propyl, halogeno-$C_1$–$C_2$-alkyl, in particular trifluoromethyl, allyl, propargyl, halogeno-$C_2$–$C_3$-alkenyl, $C_1$–$C_2$-alkoxy-$C_1$–$C_2$-alkyl, in each case optionally mono-, di- or trisubstituted benzyl or phenethyl, the substituents being identical or different, or mono-, di- or trisubstituted phenyl, the substituents being identical or different, where phenyl substituents which may be mentioned in each case are fluorine, chlorine, methyl, trifluoromethyl and dimethylamino, and $R^{7-2}$ represents hydrogen or methyl, the compound 1-phenyl-3-(4-methoxyphenyl)-4-N,N-dimethylamino-pyrazolin-5-one being excluded.

The following pyrazolin-5-one derivatives of the formula (If) may be mentioned separately, in addition to the compounds mentioned in the preparation examples:

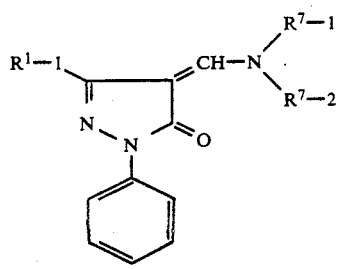
(If)
TABLE 2
| $R^{1-1}$ | $R^{7-1}$ | $R^{7-2}$ |
|---|---|---|
| 3-F-C₆H₄ | CH₃ | CH₃ |
| 3-F-C₆H₄ | H | CH₃ |
| 2-OCF₃-C₆H₄ | CH₃ | CH₃ |
| 2-OCF₃-C₆H₄ | H | CH₃ |
| 3-CF₃O-C₆H₄ | CH₃ | CH₃ |
| 3-CF₃O-C₆H₄ | H | CH₃ |
| 2-CN-C₆H₄ | CH₃ | CH₃ |
| 2-CN-C₆H₄ | H | CH₃ |
TABLE 2-continued
| $R^{1-1}$ | $R^{7-1}$ | $R^{7-2}$ |
|---|---|---|
| 2-SCF₃-C₆H₄ | CH₃ | CH₃ |
| 2-SCF₃-C₆H₄ | H | CH₃ |
| 3-CF₃S-C₆H₄ | CH₃ | CH₃ |
| 3-CF₃S-C₆H₄ | H | CH₃ |
| 3-CF₃O₂S-C₆H₄ | CH₃ | CH₃ |
| 3-CF₃O₂S-C₆H₄ | CH₃ | CH₃ |
| 3-CF₃O₂S-C₆H₄ | H | CH₃ |
| 3-CH₃O₂C-C₆H₄ | CH₃ | CH₃ |
| 3-CH₃O₂C-C₆H₄ | H | CH₃ |
| 3-CF₃-C₆H₄ | CH₃ | CH₃ |

TABLE 2-continued

| $R^{1-1}$ | $R^{7-1}$ | $R^{7-2}$ |
|---|---|---|
| 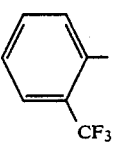 (2-CF₃-C₆H₄) | H | CH₃ |
| 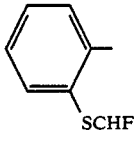 (2-SCHF₂-C₆H₄) | CH₃ | CH₃ |
| 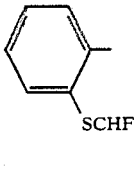 (2-SCHF₂-C₆H₄) | H | CH₃ |
| 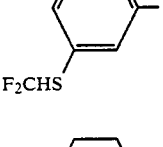 (3-F₂CHS-C₆H₄) | CH₃ | CH₃ |
| 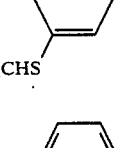 (3-F₂CHS-C₆H₄) | H | CH₃ |
| 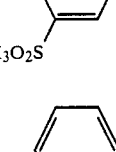 (3-CH₃O₂S-C₆H₄) | CH₃ | CH₃ |
| 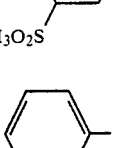 (3-CH₃O₂S-C₆H₄) | H | CH₃ |
| 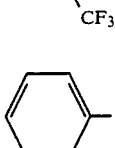 (2-CF₃-C₆H₄) | CH₃ | CH₃ |
| 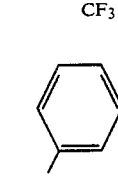 (2-CF₃-C₆H₄) | H | CH₃ |
|  (3-(CH₃)₂N-C₆H₄) | CH₃ | CH₃ |
| 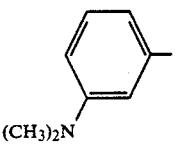 (3-(CH₃)₂N-C₆H₄) | H | CH₃ |
| 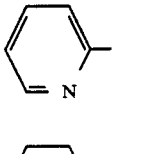 (2-pyridyl) | CH₃ | CH₃ |
| 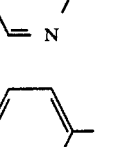 (2-pyridyl) | H | CH₃ |
| 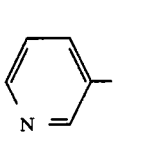 (3-pyridyl) | CH₃ | CH₃ |
| 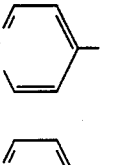 (3-pyridyl) | H | CH₃ |
| 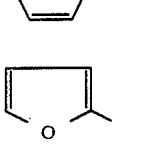 (4-pyridyl) | CH₃ | CH₃ |
| 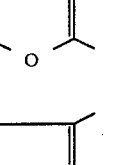 (4-pyridyl) | H | CH₃ |
| 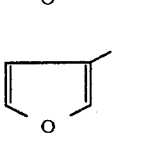 (2-furyl) | CH₃ | CH₃ |
| 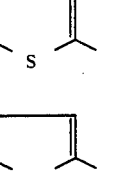 (2-furyl) | H | CH₃ |
| (3-furyl) | CH₃ | CH₃ |
| (3-furyl) | H | CH₃ |
| (2-thienyl) | CH₃ | CH₃ |
| (2-thienyl) | H | CH₃ |

TABLE 2-continued

| R¹⁻¹ | R⁷⁻¹ | R⁷⁻² |
|---|---|---|
| 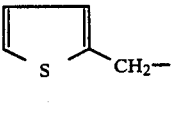 | CH₃ | CH₃ |
| 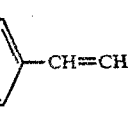 | H | CH₃ |
|  | CH₃ | CH₃ |
| 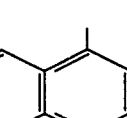 | H | CH₃ |
| 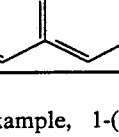 | CH₃ | CH₃ |
| 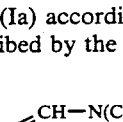 | H | CH₃ |
| 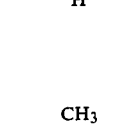 | CH₃ | CH₃ |
| 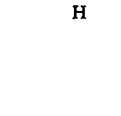 | H | CH₃ |

If, for example, 1-(2,6-dichloro-4-trifluoromethylphenyl)-4-(N,N-dimethylaminomethylidene)-3-methyl-pyrazolin-5-one and methylamine are used as starting substances, then the course of the reaction for the preparation of the substituted pyrazolin-5-one derivatives of the formula (Ia) according to process variation (Ia/α) can be described by the following scheme:

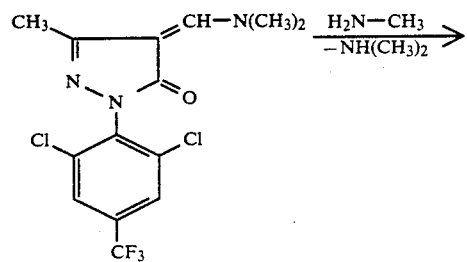

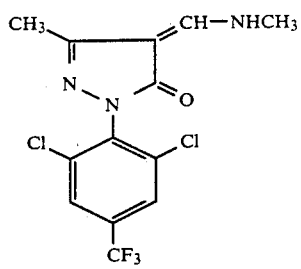

If, for example, 1-(2,6-dichloro-4-trifluoromethylphenyl)-4-formyl-3-methyl-pyrazolin-5-one and 2,4-dichloroaniline are used as starting substances, then the course of the reaction for the preparation of the substituted pyrazolin-5-one derivatives of the formula (Ia) according to process variation (Ia/β) can be described by the following scheme:

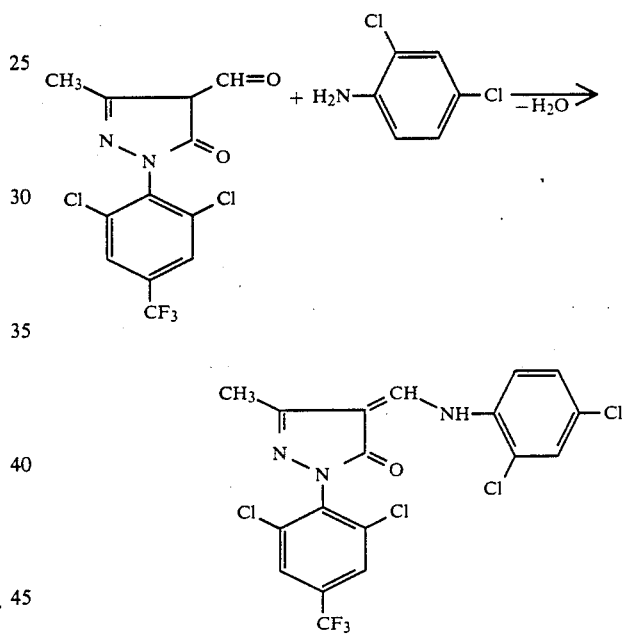

If, for example, 1-(2,6-dichloro-4-trifluoromethylphenyl)-4-(N,N-dimethylaminomethylidene)-pyrazolin-5-one and N-methylhydroxylamine hydrochloride are used as starting substances, then the course of the reaction for the preparation of the substituted pyrazolin-5-one derivatives of the formula (Ib) can be described by the following scheme:

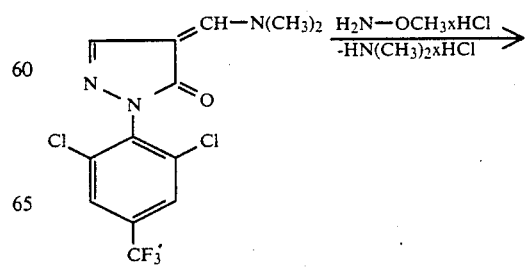

-continued

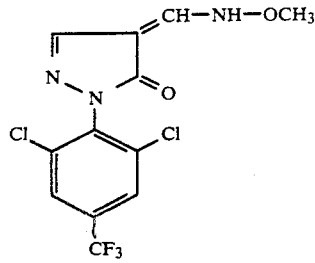

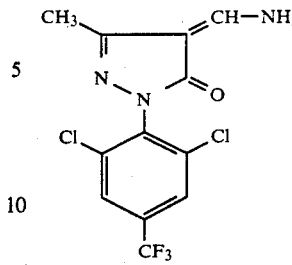

If, for example, 1-(2,6-dichloro-4-trifluoromethyl-phenyl)-4-(N,N-dimethylaminomethylidene)-3-methyl-pyrazolin-5-one and ammonia are used as starting substances, then the course of the reaction for the preparation of the substituted pyrazolin-5-one derivatives of the formula (Ic) according to process variation (Ic/α) can be described by the following scheme:

If, for example, 1-(2,6-dichloro-4-trifluoromethyl-phenyl)-3-methyl-pyrazolin-5-one and dimethylformamide in the presence of a diluent are used as starting substances, then the course of the reaction for the preparation of the substituted pyrazolin-5-one derivatives of the formula (Id) according to process variation (Id/α) can be described by the following scheme:

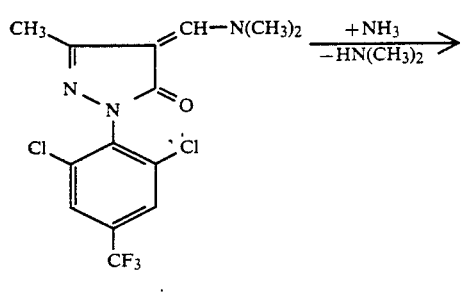

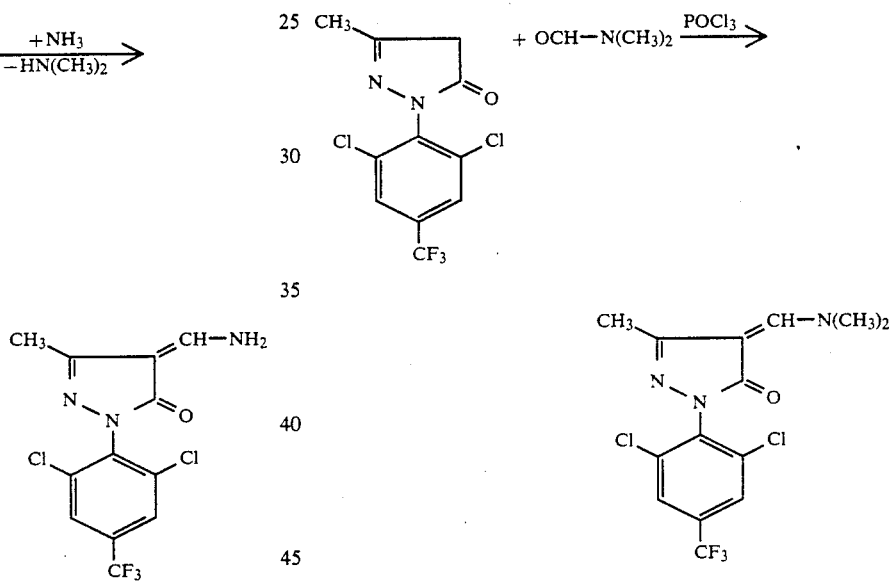

If, for example, 1-(2,6-dichloro-4-trifluoromethyl-phenyl)-3-methyl-pyrazolin-5-one and 1,3,5-triazine are used as starting substances, then the course of the reaction for the preparation of the substituted pyrazolin-5-one derivatives of the formula (Ic) according to process variation (Ic/β) can be described by the following scheme:

If, for example, 1-(2,6-dichloro-4-trifluoromethyl-phenyl)-3-methyl-pyrazolin-5-one and N,N-dimethyl-formamide dimethylacetal are used as starting substances, then the course of the reaction for the preparation of the substituted pyrazolin-5-one derivatives of the formula (Id) according to process variation (Id/β) can be described by the following scheme:

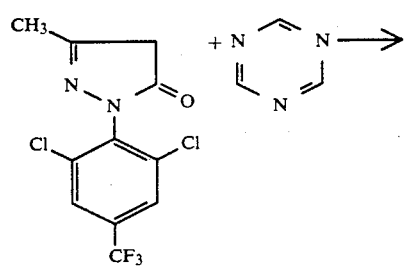

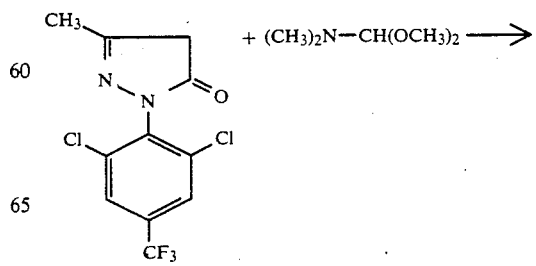

-continued

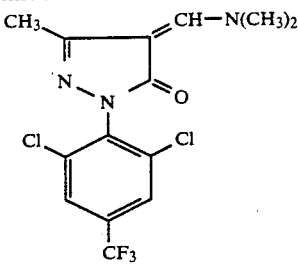

Some of the pyrazolin-5-one derivatives of the formula (III)

R¹—[pyrazolinone with CH—N(CH₃)₂]—Ar    (III)

in which
R¹ and Ar represent those radicals which have already been mentioned for these substituents in connection with the description of the substances of the formula (I),
to be used as starting substances for the preparation of the substituted pyrazolin-5-one derivatives of the formula (I) are known [see Zh.Obs.Khimii, 32, (12) 4050 (1962)].

The pyrazolin-5-one derivatives according to the invention, of the formula (Id)

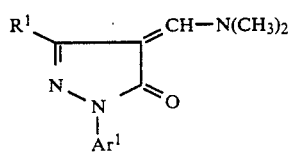

in which
R¹ and Ar¹ have the meanings given above, excluding the compounds 1-(4-nitro-phenyl)-3-methyl-4-(N,N-dimethylamino-methylidene)-pyrazolin-5-one and 1-(4-sulphophenyl)-3-methyl-4-(N,N-dimethylamino-methylidene)-pyrazolin-5-one,
to be used as starting substances for the preparation of the substituted pyrazolin-5-one derivatives of the formulae (Ia), (Ib) and (Ic) are new, part of the present invention and can be prepared as already described.

The compounds of the formula (VIII) necessary for this are compounds which are generally known in organic chemistry.

In addition to the starting products of the formula (III) mentioned in the preparation examples, the end products of the formula (Id) according to the invention may be mentioned separately at the same time:

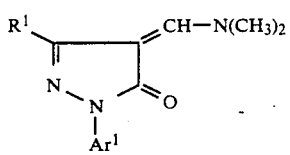

TABLE 3

| R¹ | Ar¹ |
|---|---|
| 2-OCF₃-phenyl | 4-F-phenyl |
| 2-OCF₃-phenyl | 4-CF₃-phenyl |
| 2-OCF₃-phenyl | 4-Cl-phenyl |
| 2-OCF₃-phenyl | 4-NC-phenyl |
| 3-OCF₃-phenyl | 4-F-phenyl |
| 3-CF₃O-phenyl | 4-CF₃-phenyl |
| 3-CF₃O-phenyl | 4-Cl-phenyl |
| 3-CF₃O-phenyl | 4-NC-phenyl |
| 3-CF₃O₂S-phenyl | 4-O₂N-phenyl |
| 3-CH₃O₂C-phenyl | 4-F-phenyl |

TABLE 3-continued

| R¹ | Ar¹ |
|---|---|
| 3-(CH₃O₂C)C₆H₄– | 4-Cl-C₆H₄– |
| 3-(CH₃O₂C)C₆H₄– | 4-CF₃-C₆H₄– |
| 3-(CH₃O₂C)C₆H₄– | 4-NC-C₆H₄– |
| 3-(CH₃O₂C)C₆H₄– | 4-(CH₃O₂S)C₆H₄– |
| 3-(CH₃O₂C)C₆H₄– | 4-O₂N-C₆H₄– |
| 2-(CF₃)C₆H₄– | 4-F-C₆H₄– |
| 2-(SCHF₂)C₆H₄– | 4-F-C₆H₄– |
| 3-(F₂CHS)C₆H₄– | 4-F-C₆H₄– |
| 2-(SO₂CH₃)C₆H₄– | 4-F-C₆H₄– |
| 3-(CH₃O₂S)C₆H₄– | 4-F-C₆H₄– |
| 3-((CH₃)₂N)C₆H₄– | 4-F-C₆H₄– |
| 3-(CH₃C(O))C₆H₄– | 4-F-C₆H₄– |
| 2-(CN)C₆H₄– | 4-F-C₆H₄– |
| 2-(CN)C₆H₄– | 4-Cl-C₆H₄– |
| 2-(CN)C₆H₄– | 4-CF₃-C₆H₄– |
| 2-(CN)C₆H₄– | 4-NC-C₆H₄– |
| 2-(CN)C₆H₄– | 4-(CH₃O₂S)C₆H₄– |
| 2-(CN)C₆H₄– | 4-O₂N-C₆H₄– |
| 2-(SCF₃)C₆H₄– | 4-F-C₆H₄– |
| 2-(SCF₃)C₆H₄– | 4-NC-C₆H₄– |

TABLE 3-continued

| R¹ | Ar¹ |
|---|---|
| 2-SCF₃-phenyl | 4-CH₃O₂S-phenyl |
| 2-SCF₃-phenyl | 4-O₂N-phenyl |
| 3-CF₃S-phenyl | 4-F-phenyl |
| 3-CF₃S-phenyl | 4-Cl-phenyl |
| 3-CF₃S-phenyl | 4-CF₃-phenyl |
| 3-CF₃S-phenyl | 4-NC-phenyl |
| 3-CF₃S-phenyl | 4-CH₃O₂S-phenyl |
| 3-CF₃S-phenyl | 4-O₂N-phenyl |
| 3-CF₃O₂S-phenyl | 4-F-phenyl |
| 3-CF₃O₂S-phenyl | 4-Cl-phenyl |
| 3-CF₃O₂S-phenyl | 4-CF₃-phenyl |
| 3-CF₃O₂S-phenyl | 4-NC-phenyl |
| 3-CF₃O₂S-phenyl | 4-CH₃O₂S-phenyl |
| 2-pyridyl | 4-F-phenyl |
| 3-pyridyl | 4-F-phenyl |
| 4-pyridyl | 4-F-phenyl |
| 2-Cl-6-pyridyl | 4-F-phenyl |
| phenyl | 2-Cl-4-(CH≡C—CH₂O)-5-F-phenyl |
| 3-CF₃-phenyl | 2-Cl-4-(CH≡C—CH₂O)-5-F-phenyl |
| 3-Cl-phenyl | 2-Cl-4-(CH≡C—CH₂O)-5-F-phenyl |

TABLE 3-continued

| R¹ | Ar¹ |
|---|---|
| 2-chlorophenyl | 5-chloro-4-fluoro-2-(propargyloxy)phenyl |
| 3-fluorophenyl | 4-fluorophenyl |
| 4-fluorophenyl | 4-fluorophenyl |
| 2-furyl | 4-fluorophenyl |
| 3-furyl | 4-fluorophenyl |
| 2-thienyl | 4-fluorophenyl |
| 2-thienylmethyl | 4-fluorophenyl |
| 2-(trifluoromethoxy)phenyl | 2,4-difluorophenyl |
| 3-(trifluoromethoxy)phenyl | 2,4-difluorophenyl |
| 2-cyanophenyl | 2,4-difluorophenyl |
| 3-cyanophenyl | 2,4-difluorophenyl |
| 2-(trifluoromethylthio)phenyl | 2,4-difluorophenyl |
| 3-(trifluoromethylthio)phenyl | 2,4-difluorophenyl |
| 2-(trifluoromethyl)phenyl | 2,4-difluorophenyl |
| 3-(trifluoromethylsulfonyl)phenyl | 2,4-difluorophenyl |
| 3-(methoxycarbonyl)phenyl | 2,4-difluorophenyl |
| 3-(methylsulfonyl)phenyl | 2,4-difluorophenyl |
| 3-(methoxycarbonyl)phenyl | 2,4-difluorophenyl |
| 3-(trifluoromethylsulfonyl)phenyl | 2,4-difluorophenyl |

TABLE 3-continued

| R¹ | Ar¹ |
|---|---|
| 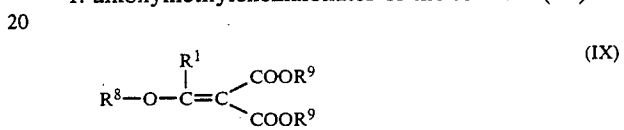 | |

The pyrazolin-5-one derivatives of the formula (VI) are partly known and partly the subject of a patent application not belonging to the published prior art, by the Applicant (cf. German Application No. P 36 25 686).

The new and known pyrazolin-5-one derivatives of the formula VI are obtained, for example, by reacting 1. alkoxymethylenemalonates of the formula (IX)

(IX)

in which
R¹ has the meaning given above and
R⁸ and R⁹ independently of one another represent methyl or ethyl,
with arylhydrazines of the formula (X)

$$Ar^1-NH-NH_2 \qquad (X)$$

in which
Ar¹ has the meaning given above,
initially in a first step, if appropriate in the presence of a diluent such as, for example, methanol or ethanol, at temperatures between 10° C. and 80° C., where the intermediate product of the formula (XI)

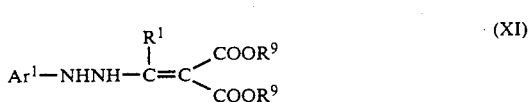
(XI)

in which
R¹, R⁹ and Ar¹ have the meaning given above,
can be isolated, where necessary, and cyclized in a separate reaction step, and the pyrazolecarboxylates thus obtained, of the formula (XII)

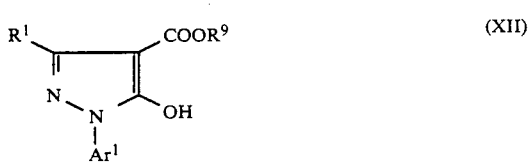
(XII)

in which
R¹, R⁹ and Ar¹ have the meanings given above,
are decarboxylated in a second step, if appropriate in the presence of a diluent such as, for example, methanol, and if appropriate in the presence of a base such as, for example, sodium hydroxide, at temperatures between 30° C. and 70° C.

The cyclization and following decarboxylation can optionally also be carried out in one reaction step as a "one-pot method" (cf., for example, Liebigs Ann.

Chem. 373, 142 (1910) and also the preparation examples).

The alkoxymethylenemalonates of the formula (IX) are compounds which are generally known in organic chemistry.

The arylhydrazines of the formula (X) are known or can be obtained by known processes (cf., for example, Houben-Weyl, Methoden der organischen Chemie [Methods of Organic Chemistry] Volume X, 2; p. 203, Thieme Verlag Stuttgart 1967) or the compounds of the formula (VI) can be obtained by reacting 2. β-ketoesters of the formula (XIII)

$$R^1-CO-CH_2-COOR^9 \qquad (XIII)$$

in which
$R^1$ and $R^9$ have the meaning given above,
with arylhydrazines of the formula (X), if appropriate in the presence of a diluent such as, for example, toluene, and if appropriate in the presence of a catalyst such as, for example, p-toluenesulphonic acid, at temperatures between 0° C. and 120° C. (cf., for example, J. Am. Chem. Soc. 64, 2133 (1942), or 3. by reacting propiolates of the formula (XIV)

$$CH\equiv C-COOR^9 \qquad (XIV)$$

in which
$R^9$ has the meaning given above,
with arylhydrazines of the formula (X), if appropriate in the presence of a diluent such as, for example, toluene, at temperatures between 0° C. and 120° C., and reacting the intermediate thus obtained, of the formula (XV)

$$Ar^1-NH-NH-CH=CH-COOR^9 \qquad (XV)$$

in which
$Ar^1$ and $R^9$ have the meaning given above,
in the presence of a strong base such as, for example, sodium methylate and if appropriate in the presence of a diluent such as, for example, methanol, at temperatures between 0° C. and 80° C., or 4. by reacting compounds of the formula (XIVa)

$$\begin{matrix} R^{9-1}O \\ R^{9-1}O \end{matrix} C=CH-COOR^{9-1} \qquad (XIVa)$$

in which
$R^{9-1}$ represents $C_1-C_4$-alkyl, in particular methyl or ethyl,
with arylhydrazines of the formula (X), if appropriate in the presence of a diluent such as, for example, ethanol, at temperatures between 0° C. and 120° C., and reacting the intermediate thus obtained, of the formula (XVa)

$$Ar^1-NH-NH-C=CH-COOR^{9-1} \atop OR^{9-1} \qquad (XVa)$$

in which
$Ar^1$ and $R^{9-1}$ have the meanings given above,
in the presence of a strong base such as, for example, sodium methylate and if appropriate in the presence of a diluent such as, for example, ethanol, at temperatures between 50° C. and 150° C.

The propiolates of the formula (XIV) and the compounds of the formula XIVa are compounds which are generally known in organic chemistry or which can be prepared by known methods.

The following pyrazolin-5-one derivatives of the formula (VI) may be mentioned separately in addition to the compounds mentioned in the preparation examples:

TABLE 4

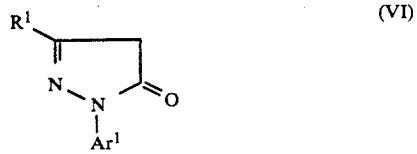

| $R^1$ | $Ar^1$ |
|---|---|
| 2-OCF₃-phenyl | 4-F-phenyl |
| 2-OCF₃-phenyl | 4-CF₃-phenyl |
| 2-OCF₃-phenyl | 4-Cl-phenyl |
| 2-OCF₃-phenyl | 4-NC-phenyl |
| 3-OCF₃-phenyl | 4-F-phenyl |
| 3-OCF₃-phenyl | 4-CF₃-phenyl |
| 3-OCF₃-phenyl | 4-Cl-phenyl |
| 3-OCF₃-phenyl | 4-NC-phenyl |

TABLE 4-continued
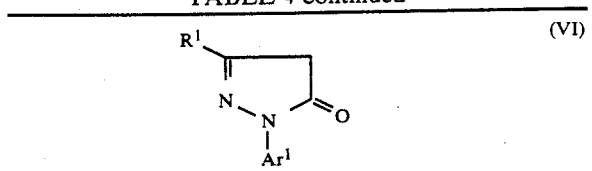
(VI)
| R¹ | Ar¹ |
|---|---|
| 2-CN-C₆H₄ | 4-F-C₆H₄ |
| 2-CN-C₆H₄ | 4-Cl-C₆H₄ |
| 2-CN-C₆H₄ | 4-CF₃-C₆H₄ |
| 2-CN-C₆H₄ | 4-CN-C₆H₄ |
| 2-CN-C₆H₄ | 4-CH₃O₂S-C₆H₄ |
| 2-CN-C₆H₄ | 4-O₂N-C₆H₄ |
| 2-SCF₃-C₆H₄ | 4-F-C₆H₄ |
| 2-SCF₃-C₆H₄ | 4-Cl-C₆H₄ |
| 2-SCF₃-C₆H₄ | 4-CF₃-C₆H₄ |
| 2-SCF₃-C₆H₄ | 4-CN-C₆H₄ |
| 2-SCF₃-C₆H₄ | 4-CH₃O₂S-C₆H₄ |
| 2-SCF₃-C₆H₄ | 4-O₂N-C₆H₄ |
| 3-CF₃S-C₆H₄ | 4-F-C₆H₄ |
| 3-CF₃S-C₆H₄ | 4-Cl-C₆H₄ |
| 3-CF₃S-C₆H₄ | 4-CF₃-C₆H₄ |
| 3-CF₃S-C₆H₄ | 4-CN-C₆H₄ |
| 3-CF₃S-C₆H₄ | 4-CH₃O₂S-C₆H₄ |

TABLE 4-continued
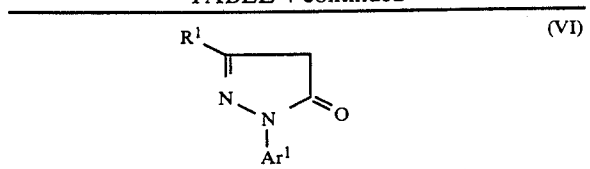
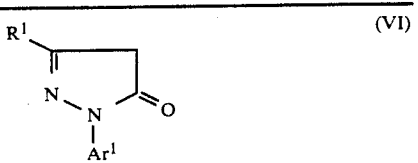
| R¹ (3-substituted phenyl) | Ar¹ (4-substituted phenyl) |
|---|---|
| 3-CF₃S | 4-O₂N |
| 3-CF₃O₂S | 4-F |
| 3-CF₃O₂S | 4-Cl |
| 3-CF₃O₂S | 4-CF₃ |
| 3-CF₃O₂S | 4-NC |
| 3-CF₃O₂S | 4-CH₃O₂S |
| 3-CF₃O₂S | 4-O₂N |
| 3-CH₃O₂C | 4-F |
| 3-CH₃O₂C | 4-Cl |
| 3-CH₃O₂C | 4-CF₃ |
| 3-CH₃O₂C | 4-NC |
| 3-CH₃O₂C | 4-CH₃O₂S |
| 3-CH₃O₂C | 4-O₂N |
| 2-CF₃ | 4-F |
| 2-SCHF₂ | 4-F |
| 3-F₂CHS | 4-F |
| 2-SO₂CH₃ | 4-F |
| 3-CH₃O₂S | 4-F |

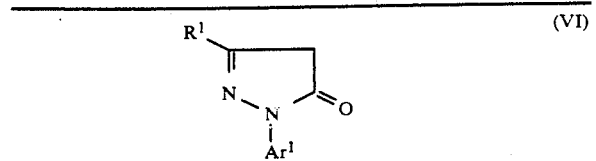

TABLE 4-continued
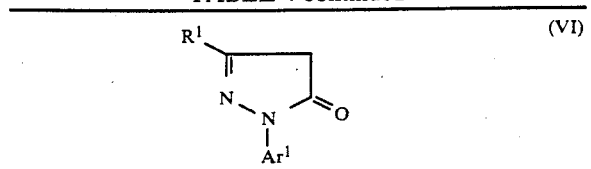
| R¹ | Ar¹ |
|---|---|
| 3-NC-C₆H₄- | 2,4-F₂-C₆H₃- |
| 2-SCF₃-C₆H₄- | 2,4-F₂-C₆H₃- |
| 3-CF₃S-C₆H₄- | 2,4-F₂-C₆H₃- |
| 2-CF₃-C₆H₄- | 2,4-F₂-C₆H₃- |
| 3-CF₃O₂S-C₆H₄- | 2,4-F₂-C₆H₃- |
| 3-CH₃O₂C-C₆H₄- | 2,4-F₂-C₆H₃- |
| 3-CH₃O₂S-C₆H₄- | 2,4-F₂-C₆H₃- |
| 3-CH₃O₂C-C₆H₄- | 2,4-F₂-C₆H₃- |
| 2-pyridyl | 2,4-F₂-C₆H₃- |
| 3-pyridyl | 2,4-F₂-C₆H₃- |
| 4-pyridyl | 2,4-F₂-C₆H₃- |
| 2-furyl | 2,4-F₂-C₆H₃- |
| 3-furyl | 2,4-F₂-C₆H₃- |
| 2-thienyl | 2,4-F₂-C₆H₃- |
| 1-naphthyl | 4-F-C₆H₄- |
| 1-naphthyl | 2,4-F₂-C₆H₃- |
| C₆H₅-CH=CH- | 4-F-C₆H₄- |
| C₆H₅-CH=CH- | 2,4-F₂-C₆H₃- |
| 3-CF₃-C₆H₄-CH=CH- | 4-F-C₆H₄- |

TABLE 4-continued

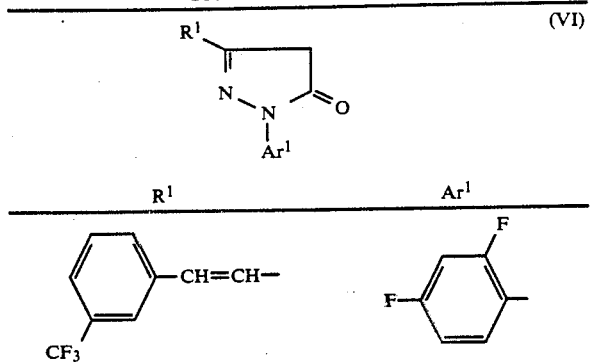

The amines to be used additionally as starting substances in the processes (Ia/α) and (Ia/β) according to the invention are generally defined by the formula (II). In this formula (II), $R^7$ represents those radicals which have already been mentioned for these substituents in connection with the description of the substances of the formula (Ia) according to the invention.

The amines of the formula (II) are compounds which are generally known in organic chemistry.

Some of the 4-formyl-pyrazolin-5-one derivatives of the formula (IVa)

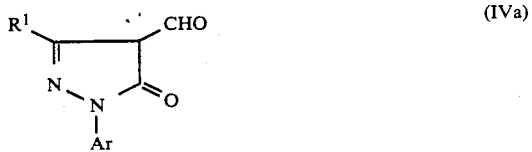

in which
R¹ and Ar represent those radicals which have already been mentioned for these substituents in connection with the description of the substances of the formula (I),
to be used as starting substances for the preparation of the substituted pyrazolin-5-one derivatives of the formula (I), are known [Kurkorskaya, L. N., Zh. Org. Khim., 11 (8), 1734 (1975)].

The 4-formyl-pyrazolin-5-one derivatives additionally to be used as starting substances in process (Ia/β) according to the invention are generally defined by the formula (IV). In this formula (IV), R¹ and Ar¹ represent those radicals which have already been mentioned for these substituents in connection with the description of the substances of the formula (Ia), according to the invention.

The compounds of the formula (IV) are new and are part of the present invention.

The compounds of the formula (IV) can be obtained by hydrolysing 4-(N,N-dimethylamino-methylidene)-pyrazolin-5-one derivatives of the formula (Id)

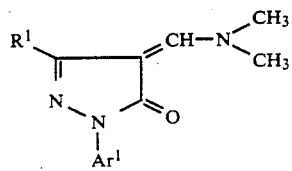

in which
R¹ and Ar¹ have the meaning given above, if appropriate in the presence of a diluent and in the presence of a base. The preparation of the starting substances of the formula (IV) is preferably performed using diluents.

As such can be considered practically all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone and also dimethyl sulphoxide, tetramethylene sulphone and hexamethylphosphoric acid triamide.

Alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate and potassium carbonate, sodium methylate and potassium methylate or sodium ethylate or potassium ethylate, are suitable bases, and are employed in excess.

The hydroxylamines to be used additionally as starting substances for the preparation of the substituted pyrazolin-5-one derivatives of the formula (Ib) are generally defined by the formula (V). In this formula (V), $R^6$ preferably represents those radicals which have already been mentioned as preferable for these substituents in connection with the description of the substances of the formula (Ib), according to the invention.

The hydroxylamines of the formula (V) are compounds which are generally known in organic chemistry.

The 4-(N,N-dimethylamino-methylidene)-pyrazolin-5-one derivatives to be used additionally as starting substances for the preparation of the substituted pyrazolin-5-one derivatives of the formulae (Ia), (Ib) and (Ic), and which are a part of the invention, are generally defined by the formula (Id).

The 1,3,5-triazine of the formula (VII) additionally necessary for the preparation of the substituted pyrazolin-5-one derivatives of the formula (Ic) according to process variation (Ic/β) is a compound which is generally known in organic chemistry.

The pyrazolin-5-ones to be used additionally as starting substances for the preparation of the substituted pyrazolin-5-one derivatives of the formula (Ic) according to process variation (Ic/β) are generally defined by the formula (VI). In this formula (VI), R¹ and Ar¹ preferably represent those radicals which have already been mentioned as preferable for these substituents in connection with the description of the substances of the formula (Ic), according to the invention.

The compounds of the formula (VI) have already been described above in the description of the starting substances for the preparation of the new compounds of the formula (Id). The processes for the preparation of the new pyrazolin-5-one derivatives of the formulae (Ia), (Ib), (Ic) and (Id) are preferably carried out using diluents.

Practically all inert organic solvents or aqueous systems can be considered as diluents. These preferably include alcohols such as methanol, ethanol, methoxyethanol, propanol or t-butanol, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoric acid triamide, and also water or aqueous-organic two-phase mixtures, such as dichloromethane-water or toluene-water.

The reaction temperatures can be varied over a relatively large range in the processes for the preparation of the new pyrazolin-5-one derivatives of the formulae (Ia), (Ib), (Ic) and (Id). In general, temperatures between 0° C. and 180° C., preferably temperatures between 10° C. and 150° C., are used.

The processes for the preparation of the new pyrazolin-5-one derivatives of the formulae (Ia) to (Id) are generally carried out at atmospheric pressure. Under certain conditions, however, increased or decreased pressure can also be used.

In carrying out the processes for the preparation of the new pyrazolin-5-one derivatives of the formula (Ia), (Ib) (Ic) and (Id) the starting substances necessary in each case are generally employed in approximately equimolar amounts. It is also possible, however, to use one of the two components employed in each case in a relatively large excess. The reaction mixture is stirred for several hours at the temperature required in each case. Working up and isolation are by customary methods.

The compounds of the formulae (Ia) to (Id), according to the invention, or the compounds to be used according to the invention, of the formula (I), can, if appropriate, be converted into salt-like compounds with an acid or base.

For the preparation of acid addition salts of the compounds of the formulae (I) to (Id), the following acids may preferably be considered: the hydrogen halide acids such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids such as, for example, acetic acid, maleic acid, succinic acid, fumaric acid, tartaric acid, citric acid, salicyclic acid, sorbic acid, lactic acid, and also sulphonic acids such as, for example, p-toluenesulphonic acid and 1,5-naphthalenedisulphonic acid.

The acid addition salts of the compounds of the formulae (I) to (Id) can be obtained in a simple manner by customary salt formation methods, for example by dissolving a compound of the formulae (I) to (Id) in a suitable organic solvent and adding the acid, for example hydrochloric acid, to it, and can be isolated in a known manner, for example by filtering off, and can where appropriate be purified by washing with an inert organic solvent.

For the preparation of base addition salts of the compounds of the formula (Ib), amines may preferably be considered: the alkylamines such as, for example, methylamine and dimethylamine; cycloalkylamines such as, for example, cyclopentylamine and cyclohexylamine; heterocyclic amines, such as piperidine, pyrrolidine and pyrazole. Furthermore, alkali and alkaline earth metal hydroxides such as, for example, sodium hydroxide and potassium hydroxide. The preparation can be carried out as described for the acid addition salts.

The process conditions for the preparation of pyrazolin-5-one derivatives of the formula (If) according to the process variations (If/α and β) correspond to the reaction conditions which have already been mentioned above in the description of processes (Ia/α and β).

The amines necessary as starting substances in the methods (If/α and β) according to the invention are generally defined by the formula (IIa). In the formula (IIa), $R^{7-1}$ represents those radicals which have already been mentioned for these substituents in connection with the description of the substances of the formula (If) according to the invention. The amines of the formula (IIa) are compounds which are known in organic chemistry.

The subject of the additionally necessary compounds of the formula (IIIa) has already been discussed in detail above in the description of the substances of the formula (III). In the formula (IIIa), $R^{1-1}$ has those meanings which have already been mentioned for these substituents in the description of the substances according to the invention, of the formula (If).

The 4-formyl-pyrazolin-5-one derivatives of the formula (IVb) necessary in process (If/β) come under the formula (IV) described above. $R^{1-1}$ in the formula (IVb) has those meanings which have been mentioned for this radical in the description of the substances of the formula (If).

The arylhydrazines of the formula (X), compounds of the formula (XVI) and (XIX) necessary in the process for the preparation of substituted pyrazolin-5-one derivatives of the formula (I) or (Ia), (Ib), (Ic) and (Id) with $R^1=-NH-CO-R^{10}$ are known or can be prepared in a simple manner by known methods [cf. for example, Chem. Ber. 28, 478 (1895)].

In the formulae (X), (XVII), (XVIII), (XIX) and (VIa), $Ar^1$ and $R^{11}$ have those meanings which have already been given for these substituents in the description of the substances according to the invention, of the formulae (Ia), (Ib), (Ic) or (Id).

The first and second steps of the processes are preferably carried out in the presence of a diluent.

Practically all inert organic solvents can be considered as diluents. These preferably include alcohols such as methanol, ethanol, methoxyethanol, propanol or t-butanol, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl acetate and ethyl acetate, acetic acid, nitriles such as, for example, acetonitrile and propionitrile, amides such as, for example, dimethylformamide, dimethylacetamide and N-methylpyrrolidone and also dimethyl sulphoxide, tetramethylene sulphone and hexamethylphosphoric acid triamide. The second step of the method is carried out in the presence of strong bases. Preferably, sodium methylate and sodium ethylate are used.

The reaction temperatures can be varied over a relatively large range in both the first and the second steps. In general, temperatures between 0° C. and 180° C., preferably temperatures between 10° C. and 150° C., are used.

For carrying out the process of the first and second steps the starting substances necessary in each case are generally employed in approximately equimolar amounts. It is also possible, however, to use one or both of the components employed in each case in a relatively large excess.

Inert organic solvents can be considered as diluents for carrying out the acylation of compounds of the formula (XVIII). Preferably, aliphatic or aromatic, optionally halogenated hydrocarbons, such as benzine, benzene, toluene, xylene, pentane, hexane, heptane, cyclohexane, petroleum ether, ligroin, methylene chloride, ethylene chloride, chloroform, tetrachloromethane, chlorobenzene or dichlorobenzene, ethers, such as diethyl ether or diisopropyl ether, ethylene glycol dimethyl ether, tetrahydrofuran or dioxane, ketones, such as acetone or butanone, methyl isopropyl ketone or methyl isobutyl ketone, esters, such as ethyl acetate, nitriles, such as acetonitrile or propionitrile, amides, such as dimethylformamide, dimethylacetamide, N-methylpyrrolidone or hexamethylphosphoric acid triamide, are used.

If the compounds of the formula (XIX) are used in liquid form, then it is also possible to employ these in a suitable excess as diluents.

All the inorganic and organic bases which can customarily be used can be considered as acid-binding agents for the acylation. Preferably, alkali metal hydroxides or alkali metal carbonates such as, for example, sodium hydroxide, potassium hydroxide, sodium carbonate or potassium carbonate and also tertiary amines such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU), are used.

The reaction temperatures can be varied over a relatively large range in the acylation. In general, temperatures between 0° C. and +180° C., preferably between 10° C. and +150° C., are used.

For carrying out the acylation, in general 1 to 20 mol, preferably 1 to 15 mol, of acylating agent of the formula (XIX) and in general 1 to 3 mol, preferably 1 to 2 mol, of acid-binding agent are employed per mol of 3-aminopyrazolin-5-one of the formula (XVIII). The performance of the reaction, working and isolation of the compounds of the formula (VIa) are of customary type and manner.

The active compounds which can be used according to the invention can be used as defoliants, desiccants, agents for destroying broad-leaved plants and, especially, as weedkillers. By weeds, in the broadest sense, there are to be understood all plants which grown in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success for selectively combating monocotyledon and dicotyledon weeds in monocotyledon and dicotyledon cultures, in pre- and post-emergence methods.

The active compounds utilizable according to the invention exhibit, inter alia, a strong microbicidal activity and can be employed practically for the control of undesired microorganisms. The active compounds are suitable, for example, for use as plant protection agents, particularly as fungicides.

In plant protection, fungicidal agents are employed for the control of Plasmodiophoromycetes, Oomycetes, Chytridiomycetes, Zygomycetes, Ascomycetes, Basidiomycetes and Deuteromycetes.

Some initiators of fungal and bacterial diseases, which come under the general headings listed above, may be mentioned by way of example but are not intended to be limiting:

Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species; such as, for example, *Alternaria brassicae*; and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In the treatment of parts of plants, the active compound concentrations in the use forms can be varied within a relatively large range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The active compounds which can be used according to the invention can be used protectively and systemically, against Phytophthora in tomatoes, with particularly good success.

Furthermore, the active compounds according to the invention also exhibit a fungicidal action against Pyricularia in rice.

Depending on their particular physical and/or chemical properties, the active compounds which can be used according to the invention can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or form-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds which can be used according to the invention, as such or in the form of their formulations, can also be used, for combating weeds, as mixtures with known herbicides, finished formulations or tank mixes being possible.

Known herbicides can be used for the mixtures, such as, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 3-($\alpha,\alpha,\alpha$-trifluoro-m-tolyl)-1,1-dimethylurea, 2-tert.-butylamino-4-ethylamino-6-methylthio-s-triazine, 2-chloro-N-{[4-methoxy-6-methyl-1,3,5-triazin-2-yl)-amino]-carbonyl}-benzenesulphonamide, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H,3H)-dione, 2-{4-[(3-chloro-5-trifluoromethyl-2-pyridinyl)oxy]-phenoxy}-propionic acid, the R enantiomer of (trimethylsilyl)-methyl 2-{4-[(3,5-dichloro-2-pyridinyl)oxy]-phenoxy}-propionate, 2,4-dichlorophenoxyacetic acid, 2-(2,4-dichlorophenoxy)-propionic acid, 2-(4-chloro-2-methyl-phenoxy)-propionic acid, 3,5-diiodo-4-hydroxybenzonitrile, [(4-amino-3,5-dichloro-6-fluoro-2-pyridinyl- )oxy]-acetic acid, 3-isopropyl-2,1,3-benzothiadiazin-4-one 2,2-dioxide, N-methyl-2-(1,3-benzothiazol-2-yloxy)-acetanilide, α-chloro-2',6'-diethyl-N-(2-propoxyethyl)-acetanilide, thioethyl hexahydro-1H-azepine-1-carbamate, N,N-dimethyl-N'-(3,4-dichlorophenyl)urea, 2-chloro-N-(2-ethyl-6-methylphenyl)-N-(2-methoxy-1-methylethyl)-acetamide, 2'-chloro-2-(4-chloro-o-tolyloxy)acetanilide, methyl 5-(2,4-dichlorophenoxy)-2-nitrobenzoate, methyl 2-[[[[(4-methoxy-6-methyl-1,3,5-triazin-2-yl)-amino]-carbonyl]-amino]-sulphonyl]-benzoate, methyl 2-((((((4,6-dimethoxy-2-pyrimidinyl)-amino)-carbonyl)-amino-sulphonyl)-methyl)-benzoate, N-(3,4-dichlorophenyl)-propanamide. Some mixtures surprisingly also exhibit a synergistic effect.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a relatively large range. It depends essentially on the nature of the desired effect. In general, the amounts used are between 0.01 and 15 kg of active compound per hectare of soil surface, preferably between 0.05 and 10 kg per ha.

The use and the preparation of the active compounds according to the invention is illustrated by the following examples.

USE EXAMPLES

In the following use examples the compounds listed below are used as comparison substances:

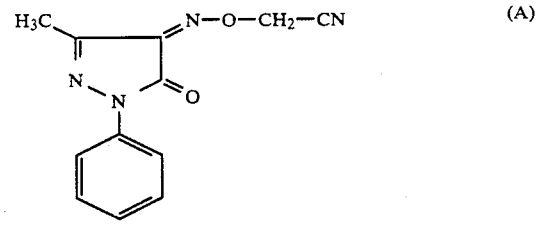

(A)

4-(Cyanomethyloximino)-3-methyl-1-phenyl-pyrazolin-5-one (known from EP-OS (European Published Specification) No. 0,166,171) and

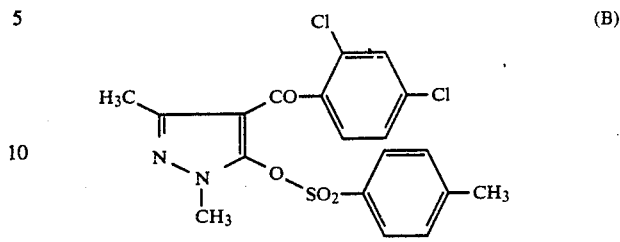

(B)

[4-(2,4-Dichlorobenzoyl)-1,3-dimethylpyrazol-5-yl]-4-methylphenylsulphonate (known from DE-OS (German Published Specification) No. 2,513,750, page 43).

EXAMPLE A

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test the compounds in the following table A, for example, exhibit markedly better herbicidal activity than the comparison substance (B).

TABLE A

Pre-emergence test/greenhouse

| Active substance | Application rate g/ha | Cotton-wool | Rice | Amaranthus | Portulak | Sinapis | Viola | Echino-chloa |
|---|---|---|---|---|---|---|---|---|
| B (known) | 500 | 0 | 0 | 0 | 0 | 0 | 0 | 0 |
| Ia-17 | 500 | 0 | 0 | 100 | 100 | 95 | 100 | 90 |
| Ia-42 | 500 | 10 | 20 | 100 | 100 | 80 | 100 | 70 |
| Ia-55 | 500 | 0 | 40 | 95 | 100 | 100 | 70 | 90 |
| Ia-87 | 500 | 10 | 0 | 100 | 100 | 70 | 70 | 40 |
| Ia-106 | 500 | 10 | 0 | 100 | 100 | 70 | 95 | 60 |
| Ia-111 | 500 | 10 | 0 | 100 | 80 | 70 | 80 | 60 |
| Ia-133 | 500 | 0 | 0 | 100 | 90 | 50 | 90 | 20 |
| Ia-137 | 500 | 10 | 0 | 80 | 80 | 90 | 95 | 30 |
| Ia-146 | 500 | 0 | 0 | 100 | 100 | 90 | 70 | 70 |
| Ia-153 | 500 | 10 | 20 | 100 | 60 | 100 | 100 | 90 |

TABLE A-continued

| | | Pre-emergence test/greenhouse | | | | | | |
|---|---|---|---|---|---|---|---|---|
| Active substance | Application rate g/ha | Cotton-wool | Rice | Amaranthus | Portulak | Sinapis | Viola | Echino-chloa |
| Ia-154 | 500 | 10 | 10 | 100 | 100 | 100 | 70 | 90 |
| Ia-172 | 500 | 20 | 0 | 100 | 100 | 70 | 90 | 90 |
| Ia-188 | 500 | 0 | 0 | 95 | 80 | 50 | — | 60 |
| Ia-189 | 500 | 10 | 0 | 100 | 100 | 70 | — | 70 |
| Ia-190 | 500 | 10 | 20 | 100 | 100 | 95 | — | 80 |

EXAMPLE B

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test the compounds listed in Table B below, for example, exhibit very good herbicidal activity, particularly in rice and wheat.

TABLE B

| | | Post-emergence test/greenhouse | | | | | |
|---|---|---|---|---|---|---|---|
| Active substance | Application rate g/ha | Rice | Wheat | Amaran-thus | Gal-ium | Vi-ola | Set-aria |
| Ia-17 | 1000 | 10 | 0 | 100 | 70 | 80 | 80 |
| Ia-42 | 1000 | 10 | 60 | 80 | 100 | 90 | 100 |
| Ia-55 | 1000 | 20 | 20 | 90 | 20 | 80 | 95 |
| Ia-87 | 500 | 10 | 0 | 80 | — | 70 | 40 |
| Ia-111 | 1000 | 60 | 40 | 100 | 60 | 90 | 90 |
| Ia-133 | 500 | 30 | 20 | 90 | 70 | 90 | 70 |
| Ia-136 | 500 | 10 | 0 | 95 | 70 | 80 | 80 |
| Ia-137 | 1000 | 0 | 0 | 95 | 50 | 95 | 70 |
| Ia-142 | 1000 | 20 | 20 | 90 | 30 | 70 | 50 |
| Ia-146 | 1000 | 10 | 10 | 95 | 80 | 50 | 60 |
| Ia-153 | 1000 | 10 | 10 | 100 | 100 | 95 | 100 |
| Ia-154 | 1000 | 20 | 10 | 60 | 30 | 70 | 60 |
| Ia-172 | 1000 | 0 | 10 | 100 | 60 | 90 | 100 |
| Ia-183 | 500 | 30 | 20 | 80 | 60 | 80 | 95 |
| Ia-187 | 500 | 60 | 20 | 70 | 60 | 90 | 70 |
| Ia-188 | 1000 | 30 | 0 | 80 | 10 | 80 | 40 |
| Ia-189 | 1000 | 30 | 0 | 100 | 95 | 95 | 50 |
| Ia-190 | 1000 | 30 | 0 | 90 | 50 | 100 | 70 |

EXAMPLE C

Phytophthora Test (Tomatoes)/Systemic

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for systemic activity, the active substance preparation is poured onto standard soil, in which young test plants are growing. Three days after treatment, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

In this test, the substances according to the invention [(Ic-1)], [(Ic)-2], [(Ic)-5], [(1c)-6], [(1c)-12] and [(Ic)-13], for example, exhibit better activity than the comparison substance (A).

TABLE C

Phytophthora test (tomato)/systemic

| Active compound | % attack at an active compound concentration of 100 ppm |
|---|---|
| 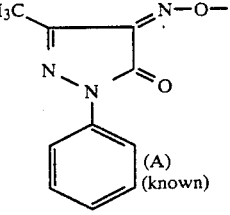 (A) (known) | 70 |
| 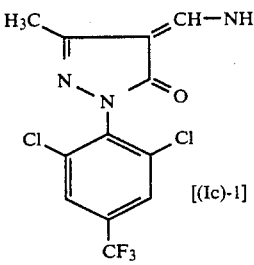 [(Ic)-1] | 10 |
| 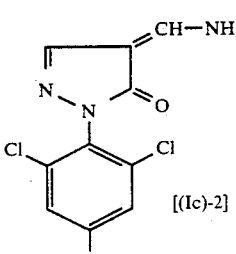 [(Ic)-2] | 24 |

TABLE C-continued

Phytophthora test (tomato)/systemic

| Active compound | % attack at an active compound concentration of 100 ppm |
|---|---|
| [(Ic)-5] — pyrazolone with H$_7$C$_3$ and CH—NH$_2$, N-(2,4,6-trichlorophenyl) | 5 |
| [(Ic)-6] — pyrazolone with H$_3$C and CH—NH$_2$, N-(2,4,6-trichlorophenyl) | 2 |
| [(Ic)-12] — pyrazolone with H$_5$C$_2$ and CH—NH$_2$, N-(2,6-dichloro-4-trifluoromethylphenyl) | 29 |
| [(Ic)-13] — pyrazolone with (CH$_3$)$_2$CH and CH—NH$_2$, N-(2,6-dichloro-4-trifluoromethylphenyl) | 15 |

EXAMPLE D

Phytophthora Test (Tomato)/Protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

In this test, the substances according to the invention [(Ic)-1], [(Ic)-2], [(Ic)-6], [(Ib)-11] and [(Ia)-11], for example, exhibit better activity than the comparison substance (A).

TABLE D

Phytophthora test (tomato)/protective

| Active compound | % attack at an active compound concentration of 10 ppm |
|---|---|
| (A) (known) — pyrazolone with H$_3$C and =N—O—CH$_2$—CN, N-phenyl | 63 |
| [(Ic)-1] — pyrazolone with H$_3$C and CH—NH$_2$, N-(2,6-dichloro-4-trifluoromethylphenyl) | 7 |
| [(Ic)-2] — pyrazolone with CH—NH$_2$, N-(2,6-dichloro-4-trifluoromethylphenyl) | 10 |
| [(Ic)-6] — pyrazolone with H$_3$C and CH—NH$_2$, N-(2,4,6-trichlorophenyl) | 10 |
| [(Ib)-11] — pyrazolone with H$_3$C and CH=N—OCH$_3$, N-(4-methylphenyl) | 30 |

TABLE D-continued

Phytophthora test (tomato)/protective

| Active compound | % attack at an active compound concentration of 10 ppm |
|---|---|
| 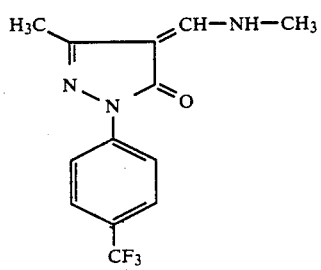 [(Ia)-11] | 30 |

Preparation Examples

EXAMPLE 1

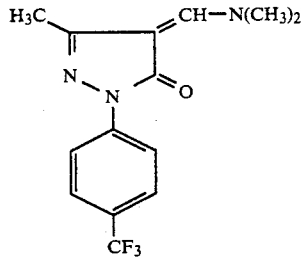 [(Ia)-1]

(Variation [(Ia)-α]

5 g (0.0168 mol) of 1-(4-trifluoromethyl-phenyl)-4-N,N-dimethylamino-methylidene-3-methyl-pyrazolin-5-one are dissolved in 50 ml of methanol and, after addition of 14 g of 30% methylamine solution, the mixture is stirred at room temperature until reaction is complete (chromatographic check). The solvent is then stripped off, the residue is stirred in petroleum ether, and the product is filtered off with suction and dried.

3.8 g (79.1% of theory) of 1-(4-trifluoromethyl-phenyl)-4-methylamino-methylidene-3-methyl-pyrazolin-5-one of melting point 129°-130° C. are obtained.

Preparation of the Starting Substances

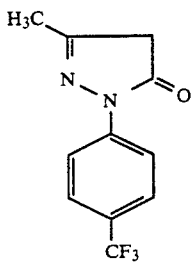

[(III-69) corresponds to a compound of the formula (Id)]

28.6 g (0.12 mol) of 1-(4-trifluoromethyl-phenyl)-3-methyl-pyrazolin-5-one are taken up in 150 ml of toluene and, after addition of 10.9 g (0.129 mol) of N,N-dimethylformamide dimethylacetal, the mixture is stirred at room temperature until the reaction is complete (chromatographic check). The solvent is then stripped off, the residue is stirred with petroleum ether, and the product is filtered off with suction and dried.

29.4 g (82.6% of theory) of 1-(4-trifluoromethyl-phenyl)-4-N,N-dimethylamino-methylidene-3-methyl-pyrazolin-5-one of melting point 230°-233° C. are obtained.

(VI-1)

(Process 2)

22.2 g (0.17 mol) of ethyl acetoacetate and 30 g (0.170 mol) of 4-trifluoromethyl hydrazine are heated for 24 hours in toluene on a water separator after addition of a spatula tip of p-toluenesulphonic acid. After cooling, the mixture is washed with water, dried and evaporated. The residue is stirred with petroleum ether, and the product is filtered off with suction and dried.

28.6 g (69.5% of theory) of 1-(4-trifluoromethyl-phenyl)-3-methyl-pyrazolin-5-one of melting point 130° C. are obtained.

EXAMPLE 2

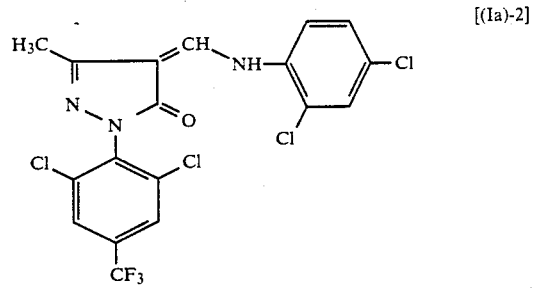 [(Ia)-2]

(Variation [(Ia)-β]

5 g (0.0148 mol) of 1-(2,6-dichloro-4-trifluoromethyl-phenyl)-4-formyl-3-methyl-pyrazolin-5-one are taken up in 50 ml of dioxane and, after addition of 2.4 g (0.0148 mol) of 2,4-dichloroaniline, the solution is heated to 80° C. for 30 minutes. The solvent is then stripped off, the residue is stirred with petroleum ether, and the product is filtered off with suction and dried.

5.0 g (70% of theory) of 4-[(2,4-dichloro-phenylamino)-methylidene]-1-(2,6-dichloro-4-trifluoromethylphenyl)-3-methyl-pyrazolin-5-one of melting point 230°-232° C. are obtained.

Preparation of the Starting Substances

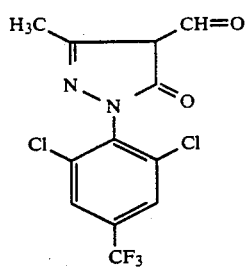

(IV-1)

7.32 g (0.02 mol) of 1-(2,6-dichloro-4-trifluoromethyl-phenyl)-3-methyl-4-N,N-dimethylamino-methylidene-pyrazolin-5-one are suspended in 70 ml of water and, after addition of 1.12 g (0.02 mol) of potassium hydroxide, the suspension is stirred for 3 hours at 45° to 50° C. It is then cooled to 0° C. and acidified using 10% strength hydrochloric acid, and the precipitated solid is filtered off with suction and dried.

6.15 g (90.4% of theory) of 1-(2,6-dichloro-4-trifluoromethyl-phenyl)-4-formyl-3-methyl-pyrazolin-5-one of melting point 195°–197° C. are obtained.

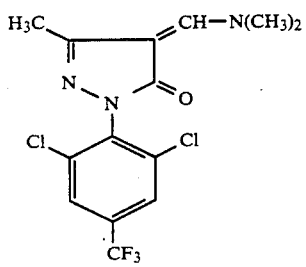

[(III-1) corresponds to a compound of the formula (Id)]

18.7 g (0.06 mol) of 1-(4-trifluoromethyl-2,6-dichloro-phenyl)-3-methyl-pyrazolin-5-one are taken up in 100 ml of toluene and added at room temperature to 7.5 g (0.063 mol) of N,N-dimethylformamide dimethylacetal. The reaction mixture is then stirred at room temperature until reaction is complete (chromatographic check). The solvent is stripped off, and the residue is triturated with petroleum ether, filtered off with suction and dried.

21.8 g (99% of theory) of 1-(4-trifluoromethyl-2,6-dichlorophenyl)-3-methyl-4-N,N-dimethylamino-methylidene-pyrazolin-5-one of melting point 195° C. are obtained.

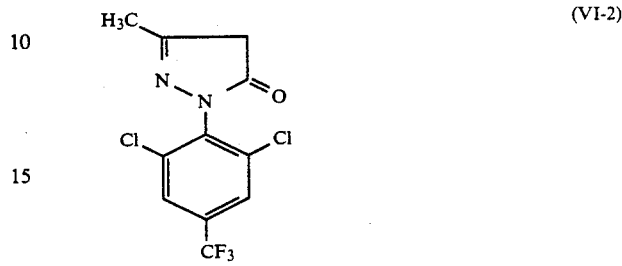

(VI-2)

(Process 2)

116 g (1 mol) of ethyl acetoacetate and 245 g (1 mol) of 2,6-dichloro-4-trifluoromethyl-phenylhydrazine are heated in 1 l of toluene, after the addition of a catalytic amount of p-toluenesulphonic acid, on a water separator until reaction is complete (chromatographic check). The solution is then cooled in an ice-bath, and the precipitated solid is filtered off with suction, stirred with petroleum ether, filtered off with suction and dried.

218.5 g (70.2% of theory) of 1-(4-trifluoromethyl-2,6-dichloro-phenyl)-3-methyl-pyrazolin-5-one of melting point 174°–175° C. are obtained.

The following end products of the formula (Ia)

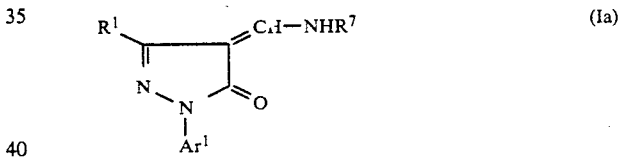

(Ia)

can be obtained analogously to the preparation examples [(Ia)-1] and [(Ia)-2] and in accordance with the given processes.

TABLE 5

| Example No. | $R^1$ | $R^7$ | $Ar^1$ | Melting point (°C.) |
|---|---|---|---|---|
| (Ia)-3 | $CH_3$ | $CH_3$ | 2,6-dichloro-4-CF$_3$-phenyl | 199 |
| (Ia)-4 | $CH_3$ | $C_2H_5$ | 2,6-dichloro-4-CF$_3$-phenyl | 177 |

TABLE 5-continued
| Example No. | R¹ | R⁷ | Ar¹ | Melting point (°C.) |
|---|---|---|---|---|
| (Ia)-5 | CH₃ | —CH₂—CH=CH₂ | 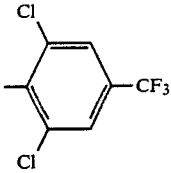 | 152 |
| (Ia)-6 | CH₃ | 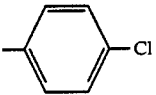 | 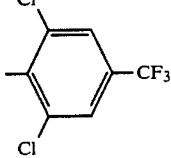 | 239 |
| (Ia)-7 | CH₃ | —CH(CH₃)₂ | 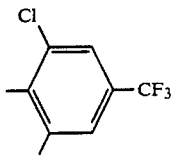 | 197 |
| (Ia)-8 | CH₃ | CH₃ | 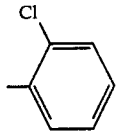 | 198 |
| (Ia)-9 | CH₃ | CH₃ | 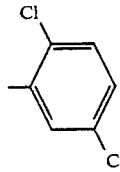 | 192 |
| (Ia)-10 | CH₃ | CH₃ | 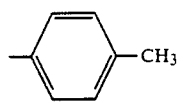 | 195 |
| (Ia)-11 | n-C₃H₇ | CH₃ | 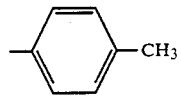 | 120 |
| (Ia)-12 | n-C₃H₇ | CH₃ | 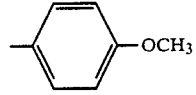 | 98 |
| (Ia)-13 | C₂H₅ | CH₃ | 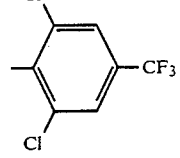 | 187–188 |
| (Ia)-14 | —CH(CH₃)₂ | CH₃ | 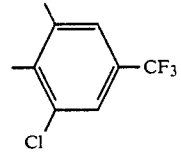 | 175 |

TABLE 5-continued
| Example No. | R¹ | R⁷ | Ar¹ | Melting point (°C.) |
|---|---|---|---|---|
| (Ia)-15 | —C(CH₃)₃ | CH₃ | 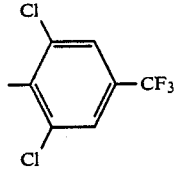 | 207 |
| (Ia)-16 | CH₃ | CH₃ | 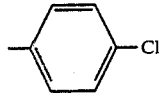 | 195 |
| (Ia)-17 | n-C₃H₇ | CH₃ | 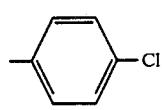 | 126 |
| (Ia)-18 | CH₃ | CH₃ | 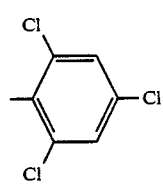 | 216 |
| (Ia)-19 | n-C₃H₇ | CH₃ | 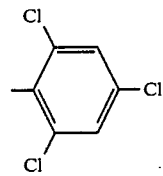 | 227 |
| (Ia)-20 | CH₃ | CH₃ | 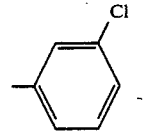 | 130–133 |
| (Ia)-21 | H | CH₃ | 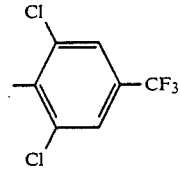 | 183 |
| (Ia)-22 | CH₃ | CH₃ |  | 156 |
| (Ia)-23 | n-C₃H₇ | CH₃ |  | 80 |
| (Ia)-24 | CH₃ |  | 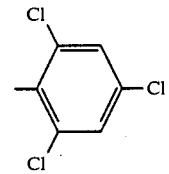 | 208–209 |

TABLE 5-continued

| Example No. | R¹ | R⁷ | Ar¹ | Melting point (°C.) |
|---|---|---|---|---|
| (Ia)-25 | $CF_3$ | $CH_3$ | 2,6-dichloro-4-(trifluoromethyl)phenyl | 231–236 |
| (Ia)-26 | phenyl | $CH_3$ | 2,6-dichloro-4-(trifluoromethyl)phenyl | 240–241 |
| (Ia)-27 | $n\text{-}C_3H_7$ | $CH_3$ | 2,6-dichloro-4-(trifluoromethyl)phenyl | 158 |
| (Ia)-28 | $CH_3$ | 4-fluorophenyl | 2,6-dichloro-4-(trifluoromethyl)phenyl | 206 |
| (Ia)-29 | cyclopropyl | $CH_3$ | 2,6-dichloro-4-(trifluoromethyl)phenyl | 216–218 |
| (Ia)-30 | $CH_3$ | $CH_3$ | 2-chloro-4-(trifluoromethyl)phenyl | 213 |
| (Ia)-31 | $CH_3$ | 4-methylphenyl | 2,6-dichloro-4-(trifluoromethyl)phenyl | 216 |
| (Ia)-32 | $CH_3$ | 4-(dimethylamino)phenyl | 2,6-dichloro-4-(trifluoromethyl)phenyl | 100 (decomposition) |
| (Ia)-33 | $CH_3$ | 3,4-dichlorophenyl | 2,6-dichloro-4-(trifluoromethyl)phenyl | 172–173 |

TABLE 5-continued
| Example No. | R¹ | R⁷ | Ar¹ | Melting point (°C.) |
|---|---|---|---|---|
| (Ia)-34 | CH₃ | CH₃ | 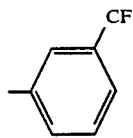 | 119-120 |
| (Ia)-35 | H | CH₃ | 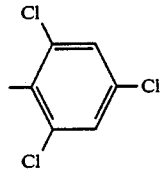 | 169-171 |
| (Ia)-36 | n-C₃H₇ | —CH₂—C(CH₃)₃ | 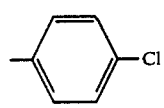 | 95 |
| (Ia)-37 | n-C₃H₇ | —(CH₂)₅—CH₃ | 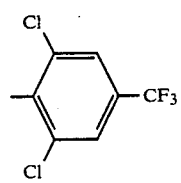 | 69-72 |
| (Ia)-38 | n-C₃H₇ | —CH(CH₃)₂ | 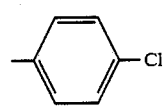 | 100 |
| (Ia)-39 | n-C₃H₇ | —CH₂CH(CH₃)₂ | 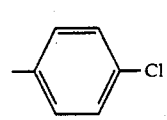 | 70-72 |
| (Ia)-40 | CH₃ | CH₃ | 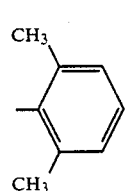 | 185 |
| (Ia)-41 | —CH₂OCH₃ | CH₃ | 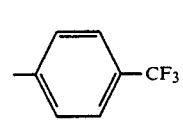 | 145-147 |
| (Ia)-42 | n-C₃H₇ | CH₃ | 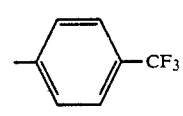 | 145-146 |
| (Ia)-43 | n-C₃H₇ | C₂H₅ | 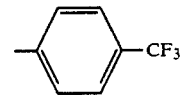 | 75-77 |
| (Ia)-44 | —CH₂OCH₃ | C₂H₅ | 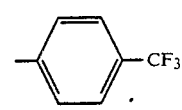 | 88-90 |

TABLE 5-continued

| Example No. | R¹ | R⁷ | Ar¹ | Melting point (°C.) |
|---|---|---|---|---|
| (Ia)-45 | $CH_3$ | $C_2H_5$ | 4-$CF_3$-phenyl | 112–114 |
| (Ia)-46 | n-$C_3H_7$ | $C_2H_5$ | 3-Cl-4-$CF_3$-phenyl | 120–122 |
| (Ia)-47 | n-$C_3H_7$ | n-$C_3H_7$ | 4-$CF_3$-phenyl | 63–64 |
| (Ia)-48 | $-CH_2OCH_3$ | n-$C_3H_7$ | 4-$CF_3$-phenyl | 41–43 |
| (Ia)-49 | $CH_3$ | n-$C_3H_7$ | 4-$CF_3$-phenyl | 79 |
| (Ia)-50 | n-$C_3H_7$ | n-$C_3H_7$ | 3-Cl-4-$CF_3$-phenyl | 105–106 |
| (Ia)-51 | n-$C_3H_7$ | $-CH(CH_3)_2$ | 4-$CF_3$-phenyl | 60–61 |
| (Ia)-52 | $CH_3$ | $-CH(CH_3)_2$ | 4-$CF_3$-phenyl | 106 |
| (Ia)-53 | $-CH_2OCH_3$ | $-CH(CH_3)_2$ | 4-$CF_3$-phenyl | 39–42 |
| (Ia)-54 | n-$C_3H_7$ | $-CH(CH_3)_2$ | 3-Cl-4-$CF_3$-phenyl | 116–118 |
| (Ia)-55 | n-$C_3H_7$ | $CH_3$ | 4-$NO_2$-phenyl | 215–217 |
| (Ia)-56 | n-$C_3H_7$ | $C_2H_5$ | 4-$NO_2$-phenyl | 164–165 |
| (Ia)-57 | n-$C_3H_7$ | n-$C_3H_7$ | 4-$NO_2$-phenyl | 123–124 |

TABLE 5-continued

| Example No. | R¹ | R⁷ | Ar¹ | Melting point (°C.) |
|---|---|---|---|---|
| (Ia)-58 | n-C$_3$H$_7$ | —CH(CH$_3$)$_2$ | 4-NO$_2$-C$_6$H$_4$— | 149–150 |
| (Ia)-59 | n-C$_3$H$_7$ | 2,4-F$_2$-C$_6$H$_3$— | 3-Cl-4-CF$_3$-C$_6$H$_3$— | 204 |
| (Ia)-60 | —CH$_2$—CH(CH$_3$)$_2$ | CH$_3$ | 4-Cl-C$_6$H$_4$— | 87–90 |
| (Ia)-61 | —CH$_2$—CH(CH$_3$)$_2$ | C$_2$H$_5$ | 4-Cl-C$_6$H$_4$— | 79–83 |
| (Ia)-62 | —CH(CH$_3$)$_2$ | CH$_3$ | 4-Cl-C$_6$H$_4$— | 115–117 |
| (Ia)-63 | —CH(CH$_3$)$_2$ | C$_2$H$_5$ | 4-Cl-C$_6$H$_4$— | 93–96 |
| (Ia)-64 | n-C$_4$H$_9$ | CH$_3$ | 4-Cl-C$_6$H$_4$— | 150–160 |
| (Ia)-65 | n-C$_4$H$_9$ | C$_2$H$_5$ | 4-Cl-C$_6$H$_4$— | 172 |
| (Ia)-66 | —C(CH$_3$)$_3$ | CH$_3$ | 4-Cl-C$_6$H$_4$— | 132–134 |
| (Ia)-67 | —C(CH$_3$)$_3$ | C$_2$H$_5$ | 4-Cl-C$_6$H$_4$— | 134–136 |
| (Ia)-68 | C$_2$H$_5$ | CH$_3$ | 4-Cl-C$_6$H$_4$— | 147–151 |
| (Ia)-69 | C$_2$H$_5$ | C$_2$H$_5$ | 4-Cl-C$_6$H$_4$— | 76–80 |
| (Ia)-70 | C$_2$H$_5$ | n-C$_3$H$_7$ | 4-Cl-C$_6$H$_4$— | 182 |

TABLE 5-continued

| Example No. | R¹ | R⁷ | Ar¹ | Melting point (°C.) |
|---|---|---|---|---|
| (Ia)-71 | C$_2$H$_5$ | —CH(CH$_3$)$_2$ | 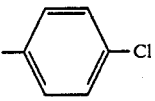 4-Cl-C$_6$H$_4$ | 195–198 |
| (Ia)-72 | —C(CH$_3$)$_3$ | —CH(CH$_3$)$_2$ | 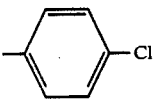 4-Cl-C$_6$H$_4$ | 141–146 |
| (Ia)-73 | n-C$_3$H$_7$ | n-C$_3$H$_7$ | 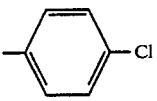 4-Cl-C$_6$H$_4$ | 150–162 |
| (Ia)-74 | —CH$_2$CH(CH$_3$)$_2$ | n-C$_3$H$_7$ | 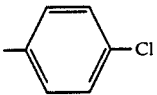 4-Cl-C$_6$H$_4$ | 63–65 |
| (Ia)-75 | —CH$_2$CH(CH$_3$)$_2$ | —CH(CH$_3$)$_2$ | 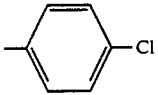 4-Cl-C$_6$H$_4$ | 93–94 |
| (Ia)-76 | —CH(CH$_3$)$_2$ | n-C$_3$H$_7$ | 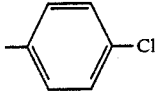 4-Cl-C$_6$H$_4$ | 59–61 |
| (Ia)-77 | —CH(CH$_3$)$_2$ | —CH(CH$_3$)$_2$ | 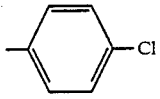 4-Cl-C$_6$H$_4$ | 96–98 |
| (Ia)-78 | n-C$_4$H$_9$ | —CH(CH$_3$)$_2$ | 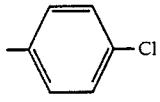 4-Cl-C$_6$H$_4$ | 245–247 |
| (Ia)-79 | n-C$_3$H$_7$ | CH$_3$ | 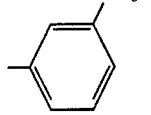 3-CF$_3$-C$_6$H$_4$ | 99 |
| (Ia)-80 | n-C$_3$H$_7$ | C$_2$H$_5$ | 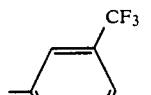 3-CF$_3$-C$_6$H$_4$ | 52–53 |
| (Ia)-81 | n-C$_3$H$_7$ | n-C$_3$H$_7$ | 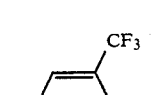 3-CF$_3$-C$_6$H$_4$ | 51 |
| (Ia)-82 | n-C$_3$H$_7$ | —CH(CH$_3$)$_2$ | 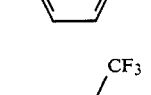 3-CF$_3$-C$_6$H$_4$ | 44 |

TABLE 5-continued

| Example No. | R¹ | R⁷ | Ar¹ | Melting point (°C.) |
|---|---|---|---|---|
| (Ia)-83 | n-C$_3$H$_7$ | 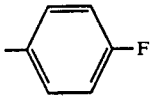 4-F-C$_6$H$_4$ | 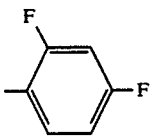 4-CF$_3$-C$_6$H$_4$ | 172–174 |
| (Ia)-84 | n-C$_3$H$_7$ | 2,4-F$_2$-C$_6$H$_3$ | 4-CF$_3$-C$_6$H$_4$ | 196–200 |
| (Ia)-85 | n-C$_3$H$_7$ | CH$_3$ | 2,3-(CH$_3$)$_2$-C$_6$H$_3$ | 123 |
| (Ia)-86 | CH$_3$ | CH$_3$ | 2,3-(CH$_3$)$_2$-C$_6$H$_3$ | 166 |
| (Ia)-87 | C$_6$H$_5$ | CH$_3$ | 4-Cl-C$_6$H$_4$ | 160 |
| (Ia)-88 | C$_6$H$_5$ | C$_2$H$_5$ | 4-Cl-C$_6$H$_4$ | 136 |
| (Ia)-89 | CH$_3$ | 2,4-F$_2$-C$_6$H$_3$ | 2,4,6-Cl$_3$-C$_6$H$_2$ | 229–230 |
| (Ia)-90 | CH$_3$ | 4-F-C$_6$H$_4$ | 2,4,6-Cl$_3$-C$_6$H$_2$ | 183 |
| (Ia)-91 | CH$_3$ | CH$_3$ | 4-OCF$_3$-C$_6$H$_4$ | 92–94 |
| (Ia)-92 | C$_2$H$_5$ | CH$_3$ | 4-OCF$_3$-C$_6$H$_4$ | 67–68 |
| (Ia)-93 | n-C$_3$H$_7$ | CH$_3$ | 4-OCF$_3$-C$_6$H$_4$ | 53–54 |
| (Ia)-94 | CH$_3$ | 4-Cl-C$_6$H$_4$ | 4-OCF$_3$-C$_6$H$_4$ | 182–183 |

TABLE 5-continued
| Example No. | R¹ | R⁷ | Ar¹ | Melting point (°C.) |
|---|---|---|---|---|
| (Ia)-95 | $C_2H_5$ | 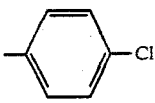 | 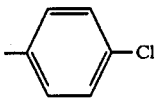 | 141–142 |
| (Ia)-96 | n-$C_3H_7$ | 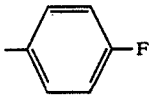 | 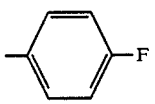 | 131–132 |
| (Ia)-97 | $CH_3$ | 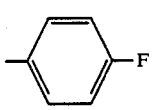 | 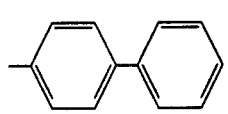 | 175–176 |
| (Ia)-98 | $C_2H_5$ | 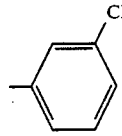 | 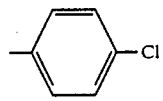 | 141–142 |
| (Ia)-99 | n-$C_3H_7$ | 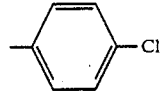 | 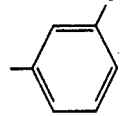 | 112–113 |
| (Ia)-100 | n-$C_3H_7$ | $CH_3$ | 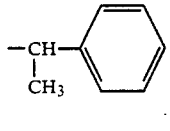 | 93 |
| (Ia)-101 | $C_2H_5$ | $CH_3$ | 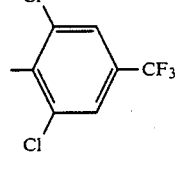 | 145 |
| (Ia)-102 | —$CH_2OCH_3$ | $CH_3$ | 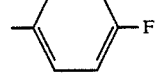 | 138–139 |
| (Ia)-103 | $CF_3$ | $CH_3$ |  | 195 |
| (Ia)-104 | $CH_3$ | $CH_3$ |  | 210–212 |
| (Ia)-105 | $CH_3$ |  |  | 160 |
| (Ia)-106 | n-$C_3H_7$ | $CH_3$ |  | 68 |

TABLE 5-continued
| Example No. | R¹ | R⁷ | Ar¹ | Melting point (°C.) |
|---|---|---|---|---|
| (Ia)-107 | n-C₃H₇ | CH₃ | 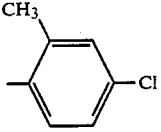 | 147-149 |
| (Ia)-108 | —CH₂SC₂H₅ | CH₃ | 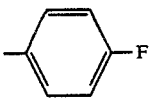 | 125 |
| (Ia)-109 | CH₃ | CH₃ | 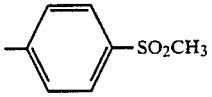 | 243 |
| (Ia)-110 | CH₃ | CH₃ | 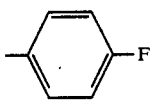 | 145 |
| (Ia)-111 | 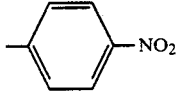 | CH₃ | 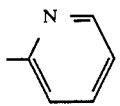 | 270 |
| (Ia)-112 | CH₃ | CH₃ | 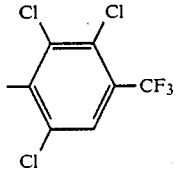 | 81 |
| (Ia)-113 | —CH₂SC₂H₅ | CH₃ | 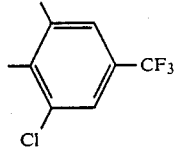 | 163-167 |
| (Ia)-114 | 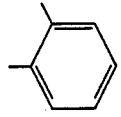 | CH₃ | | 241 |
| (Ia)-115 | —CH₂SCH₃ | CH₃ | | 103 |
| (Ia)-116 | —CH₂SCH₃ | CH₃ | 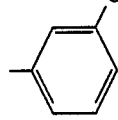 | 136 |
| (Ia)-117 | —CH₂SCH₃ | CH₃ | 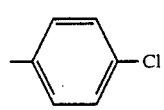 | 155 |

TABLE 5-continued

| Example No. | R¹ | R⁷ | Ar¹ | Melting point (°C.) |
|---|---|---|---|---|
| (Ia)-118 | —CH₂SCH₃ | CH₃ | 2,4,5-trichlorophenyl | 140 |
| (Ia)-119 | —CH₂SCH₃ | CH₃ | 2,6-dichloro-4-(trifluoromethyl)phenyl | 185 |
| (Ia)-120 | —CH₂SCH₃ | CH₃ | 4-fluorophenyl | 126 |
| (Ia)-121 | —CH₂SCH₃ | CH₃ | 4-(trifluoromethyl)phenyl | 143 |
| (Ia)-122 | —CH₂SCH₃ | CH₃ | 4-nitrophenyl | 234 |
| (Ia)-123 | —CH₂SCH₃ | CH₃ | 2,3,6-trichloro-4-(trifluoromethyl)phenyl | 208 |
| (Ia)-124 | —CH₂SCH₃ | —CH₂—CH=CH₂ | 2-chlorophenyl | 62 |
| (Ia)-125 | —CH₂SCH₃ | —CH₂—CH=CH₂ | 4-chlorophenyl | 133 |
| (Ia)-126 | —CH₂SCH₃ | —CH₂—CH=CH₂ | 2,6-dichloro-4-(trifluoromethyl)phenyl | 169 |
| (Ia)-127 | —CH₂SCH₃ | —CH₂—CH=CH₂ | 4-(trifluoromethyl)phenyl | 113 |
| (Ia)-128 | —CH₂SCH₃ | —CH₂—CH=CH₂ | 4-nitrophenyl | 140 |

TABLE 5-continued

| Example No. | R¹ | R⁷ | Ar¹ | Melting point (°C.) |
|---|---|---|---|---|
| (Ia)-129 | —CH₂SCH₃ | —CH₂—CH=CH₂ | 2,3-Cl₂-5-Cl-4-CF₃-phenyl | 138 |
| (Ia)-130 | H | CH₃ | 2,3-Cl₂-5-Cl-4-CF₃-phenyl | 203–204 |
| (Ia)-131 | H | CH₃ | 3-Cl-phenyl | 112–114 |
| (Ia)-132 | n-C₃H₇ | CH₃ | 4-SO₂CF₃-phenyl | 159 |
| (Ia)-133 | phenyl | CH₃ | 4-CF₃-phenyl | 151 |
| (Ia)-134 | 3,4-Cl₂-phenyl | CH₃ | 4-Cl-phenyl | 200–202 |
| (Ia)-135 | 3-Cl-phenyl | CH₃ | 4-CF₃-phenyl | 145–149 |
| (Ia)-136 | 3-Cl-phenyl | CH₃ | 4-Cl-phenyl | 168–172 |
| (Ia)-137 | 2-Cl-phenyl | CH₃ | 4-Cl-phenyl | 224 |
| (Ia)-138 | 2-Cl-phenyl | CH₃ | 2,6-Cl₂-4-CF₃-phenyl | 125–130 |

TABLE 5-continued

| Example No. | R¹ | R⁷ | Ar¹ | Melting point (°C.) |
|---|---|---|---|---|
| (Ia)-139 | 3-Cl-C₆H₄- | CH₃ | 2,6-Cl₂-4-CF₃-C₆H₂- | 208–212 |
| (Ia)-140 | 4-CH₃-C₆H₄- | CH₃ | 4-Cl-C₆H₄- | 185 |
| (Ia)-141 | 4-CH₃-C₆H₄- | CH₃ | 4-NO₂-C₆H₄- | 256–259 |
| (Ia-142) | 3-Cl-C₆H₄- | CH₃ | 4-NO₂-C₆H₄- | 250 |
| (Ia)-143 | 4-CH₃-C₆H₄- | CH₃ | 2,6-Cl₂-4-CF₃-C₆H₂- | 178 |
| (Ia)-144 | 4-Cl-C₆H₄- | CH₃ | 2,6-Cl₂-4-CF₃-C₆H₂- | 238 |
| (Ia)-145 | 2-furyl | CH₃ | 2,6-Cl₂-4-CF₃-C₆H₂- | 240 |
| (Ia)-146 | n-C₃H₇ | CH₃ | 4-SO₂CH₃-C₆H₄- | 194 |
| (Ia)-147 | 4-Cl-C₆H₄- | CH₃ | 4-NO₂-C₆H₄- | 290 |
| (Ia)-148 | 2,4-Cl₂-C₆H₃- | CH₃ | 4-Cl-C₆H₄- | 229 |

TABLE 5-continued
| Example No. | R¹ | R⁷ | Ar¹ | Melting point (°C.) |
|---|---|---|---|---|
| (Ia)-149 | 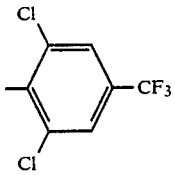 | CH₃ | 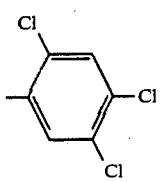 | 225-226 |
| (Ia)-150 | CH₃ | CH₃ | 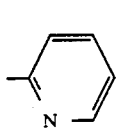 | 230-231 |
| (Ia)-151 | n-C₃H₇ | CH₃ | 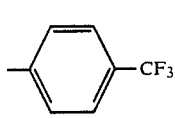 | 188-190 |
| (Ia)-152 | —CH₂SC₂H₅ | CH₃ | 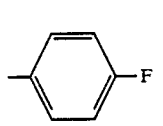 | 110 |
| (Ia)-153 | 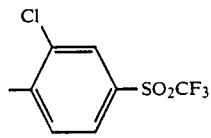 | CH₃ | 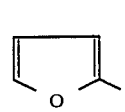 | 145 |
| (Ia)-154 | n-C₃H₇ | CH₃ | 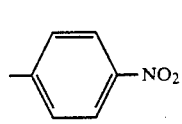 | 185 |
| (Ia)-155 | 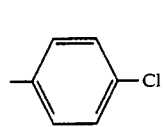 | CH₃ | 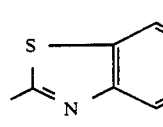 | 249 |
| (Ia)-156 | —CH₂SC₂H₅ | CH₃ | 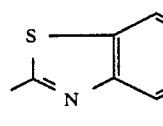 | 147 |
| (Ia)-157 | CH₃ | CH₃ | 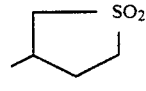 | 195 (decomposition) |
| (Ia)-158 | n-C₃H₇ | CH₃ | 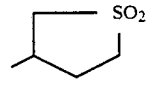 | 179-181 |
| (Ia)-159 | CH₃ | CH₃ |  | 226 |
| (Ia)-160 | CH₃ | n-C₃H₇ |  | 177 |

TABLE 5-continued

| Example No. | R¹ | R⁷ | Ar¹ | Melting point (°C.) |
|---|---|---|---|---|
| (Ia)-161 | —CH₂SC₂H₅ | CH₃ | 4-NO₂-C₆H₄ | 189–192 |
| (Ia)-162 | CH₃ | —CH₂CH₂OCH₃ | 2,4,6-tri-Cl-C₆H₂ | 178–180 |
| (Ia)-163 | CH₃ | —CH₂CH₂CH₂OCH₃ | 2,4,6-tri-Cl-C₆H₂ | 130–132 |
| (Ia)-164 | CH₃ | —CH₂CH₂OCH₃ | 4-CH₃-C₆H₄ | 206 |
| (Ia)-165 | CH₃ | —CH₂CH₂CH₂OCH₃ | 4-CH₃-C₆H₄ | 132 |
| (Ia)-166 | CH₃ | —CH₂CH₂OCH₃ | 4-NO₂-C₆H₄ | 58 |
| (Ia)-167 | CH₃ | —CH₂CH₂CH₂OCH₃ | 4-NO₂-C₆H₄ | 37 |
| (Ia)-168 | n-C₃H₇ | —CH₂CH₂CH₂OCH₃ | 4-Cl-C₆H₄ | 68–70 |
| (Ia)-169 | CH₃ | —CH₂CH₂CH₂OCH₃ | 3-CF₃-C₆H₄ | — |
| (Ia)-170 | C₆H₅ | —CH₂CH₂OCH₃ | 4-Cl-C₆H₄ | 108 |
| (Ia)-171 | C₆H₅ | —CH₂CH₂CH₂OCH₃ | 4-Cl-C₆H₄ | 116 |
| (Ia)-172 | n-C₃H₇ | CH₃ | 4-CN-C₆H₄ | 183 |

TABLE 5-continued

| Example No. | R¹ | R⁷ | Ar¹ | Melting point (°C.) |
|---|---|---|---|---|
| (Ia)-173 | n-C₃H₇ | —CH₂CH₂OCH₃ | 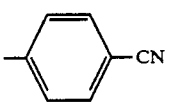 4-CN-C₆H₄ | 124 |
| (Ia)-174 | n-C₃H₇ | —CH₂CH₂OCH₃ | 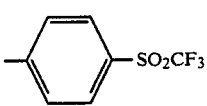 4-SO₂CF₃-C₆H₄ | 120 |
| (Ia)-175 | —CH₂-C₆H₅ 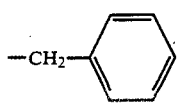 | CH₃ | 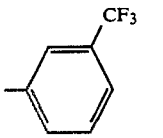 3-CF₃-C₆H₄ | 128 |
| (Ia)-176 | —CH₂-C₆H₅ 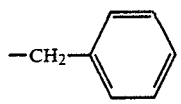 | CH₃ | 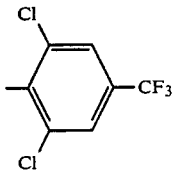 2,6-Cl₂-4-CF₃-C₆H₂ | 179 |
| (Ia)-177 | —CH₂-C₆H₅ 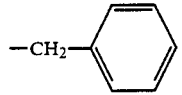 | CH₃ | 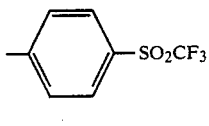 4-SO₂CF₃-C₆H₄ | 188 |
| (Ia)-178 | —CH₂SCH₃ | —CH(CH₃)-C₆H₅ 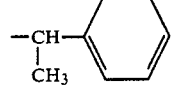 | 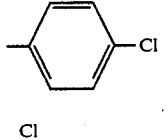 4-Cl-C₆H₄ | 60 |
| (Ia)-179 | —CH₂SCH₃ | —CH(CH₃)-C₆H₅ 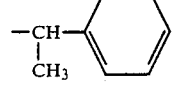 | 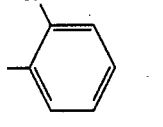 2-Cl-C₆H₄ | oil |
| (Ia)-180 | —CH₂SCH₃ | —CH(CH₃)-C₆H₅ 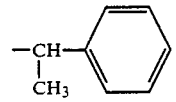 | 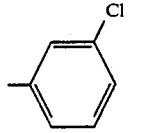 3-Cl-C₆H₄ | oil |
| (Ia)-181 | —CH₂SCH₃ | —CH(CH₃)-C₆H₅ 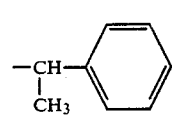 | 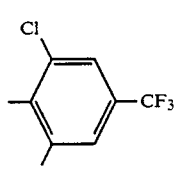 2,6-Cl₂-4-CF₃-C₆H₂ | oil |
| (Ia)-182 | nC₃H₇ | CH₃ | 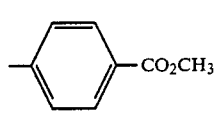 4-CO₂CH₃-C₆H₄ | 169 |
| (Ia)-183 | —C₆H₅ 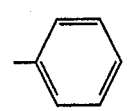 | CH₃ | 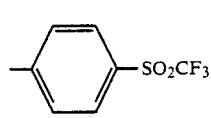 4-SO₂CF₃-C₆H₄ | 185–186 |
| (Ia)-184 | —CH₂-C₆H₅ 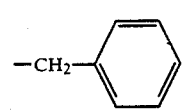 | CH₃ | 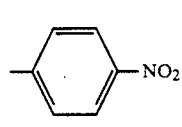 4-NO₂-C₆H₄ | 247 |

TABLE 5-continued

| Example No. | R¹ | R⁷ | Ar¹ | Melting point (°C.) |
|---|---|---|---|---|
| (Ia)-185 | —C₃H₇ | CH₃ | 4-CO₂H-C₆H₄— | 236 |
| (Ia)-186 | —OC₂H₅ | CH₃ | 2,6-Cl₂-4-CF₃-C₆H₂— | 202 |
| (Ia)-187 | —OC₂H₅ | CH₃ | 4-NO₂-C₆H₄— | 199 |
| (Ia)-188 | —CH₂-C₆H₅ | CH₃ | 4-F-C₆H₄— | 169 |
| (Ia)-189 | 3-Cl-C₆H₄— | CH₃ | 4-F-C₆H₄— | 142 |
| (Ia)-190 | 2-Cl-C₆H₄— | CH₃ | 4-F-C₆H₄— | 202–205 |
| (Ia)-191 | —OC₂H₅ | CH₃ | 4-F-C₆H₄— | 117 |
| (Ia)-192 | —CH₂-(2-Cl-C₆H₄) | CH₃ | 4-F-C₆H₄— | 165–168 |
| (Ia)-193 | —CH₂-(3-Cl-C₆H₄) | CH₃ | 2,6-Cl₂-4-CF₃-C₆H₂— | 158 |
| (Ia)-194 | —CH₂-(3-Cl-C₆H₄) | CH₃ | 4-F-C₆H₄— | 152 |

TABLE 5-continued

| Example No. | R¹ | R⁷ | Ar¹ | Melting point (°C.) |
|---|---|---|---|---|
| (Ia)-195 | —CH₂—C₆H₄—Cl (4-Cl) | CH₃ | 2,6-Cl₂-4-CF₃-C₆H₂— | 223–224 |
| (Ia)-196 | —CH₂—C₆H₄—Cl (4-Cl) | CH₃ | 4-F-C₆H₄— | 117–120 |
| (Ia)-197 | 2,4-Cl₂-C₆H₃— | CH₃ | 4-F-C₆H₄— | 229 |
| (Ia)-198 | C₆H₅— | CH₃ | 3-CF₃-C₆H₄— | 155–156 |
| (Ia)-199 | 2-CF₃-C₆H₄— | CH₃ | C₆H₅— | 126–127 |
| (Ia)-200 | CH₃ | CH₃ | 3,5-Cl₂-C₆H₃— | 136 |
| (Ia)-201 | n-C₃H₇ | CH₃ | 3,5-Cl₂-C₆H₃— | 137 |
| (Ia)-202 | C₆H₅— | CH₃ | 3,5-Cl₂-C₆H₃— | 211–212 |
| (Ia)-203 | n-C₃H₇ | CH₃ | 2,4-F₂-C₆H₃— | 68 |
| (Ia)-204 | C₆H₅— | CH₃ | 2,4-F₂-C₆H₃— | 121 |

TABLE 5-continued

| Example No. | R¹ | R⁷ | Ar¹ | Melting point (°C.) |
|---|---|---|---|---|
| (Ia)-205 | 3-CF₃-C₆H₄- | CH₃ | 2,4-F₂-C₆H₃- | 159–162 |
| (Ia)-206 | CH₃ | CH₃ | 2,4-F₂-C₆H₃- | 156 |
| (Ia)-207 | C₆H₅- | C₂H₅ | 4-F-C₆H₄- | 95 |
| (Ia)-208 | C₆H₅- | n-C₃H₇ | 4-F-C₆H₄- | 143 |
| (Ia)-209 | C₆H₅- | i-C₃H₇ | 4-F-C₆H₄- | 153 |
| (Ia)-210 | C₆H₅- | tert.—C₄H₉ | 4-F-C₆H₄- | 159 |
| (Ia)-211 | C₆H₅- | —CH₂—CH₂—OC₂H₅ | 4-F-C₆H₄- | 97 |
| (Ia)-212 | C₆H₅- | —CH₂—C(CH₃)₃ | 4-F-C₆H₄- | 158–159 |
| (Ia)-213 | 3-CF₃-C₆H₄- | CH₃ | 4-F-C₆H₄- | 133 |
| (Ia)-214 | 2,4-Cl₂-C₆H₃-CH₂- | CH₃ | 4-F-C₆H₄- | 180 |
| (Ia)-215 | 2,4-Cl₂-C₆H₃-CH₂- | CH₃ | 3-CF₃-C₆H₄- | 116 |

TABLE 5-continued

| Example No. | R¹ | R⁷ | Ar¹ | Melting point (°C.) |
|---|---|---|---|---|
| (Ia)-216 | —CH₂—C₆H₅ | CH₃ | 3-CF₃-C₆H₄— | 103–105 |
| (Ia)-217 | C₆H₅— | CH₃ | C₆H₅— | 121–122 |
| (Ia)-218 | —CH₂—S—C₆H₄-4-Cl | CH₃ | 4-F-C₆H₄— | 142–145 |
| (Ia)-219 | —CH₂—C₆H₄-3-CF₃ | CH₃ | 4-F-C₆H₄— | 136 |
| (Ia)-220 | —CH₂—C(CH₃)₃ | CH₃ | 4-F-C₆H₄— | 110–114 |
| (Ia)-221 | —CH₂—C₆H₄-3-CF₃ | CH₃ | C₆H₅— | 121 |
| (Ia)-222 | —CH₂—C₆H₄-3-CF₃ | CH₃ | 2,4-F₂-C₆H₃— | 165 |
| (Ia)-223 | —CH₂—C₆H₅ | CH₃ | 2,4-F₂-C₆H₃— | 145 |
| (Ia)-224 | C₆H₅— | CH₃ | 3-Cl-4-SO₂CF₃-C₆H₃— | 189 |
| (Ia)-225 | —NH—CO—CH₃ | CH₃ | C₆H₅— | 50–60 |
| (Ia)-226 | —NH—CO—C₆H₅ | CH₃ | C₆H₅— | 215 |

TABLE 5-continued
| Example No. | R¹ | R⁷ | Ar¹ | Melting point (°C.) |
|---|---|---|---|---|
| (Ia)-227 | —COOCH₃ | CH₃ | 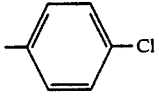 4-Cl-C₆H₄— | 204 |
| (Ia)-228 | —COOC₂H₅ | CH₃ |  4-F-C₆H₄— | 112–113 |
| (Ia)-229 | 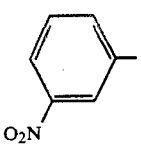 3-O₂N-C₆H₄— | CH₃ |  4-F-C₆H₄— | 287–288 |
| (Ia)-230 | 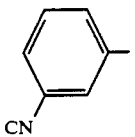 3-NC-C₆H₄— | CH₃ |  4-F-C₆H₄— | 112–115 |
| (Ia)-231 | 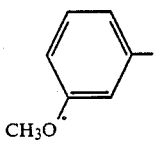 3-CH₃O-C₆H₄— | CH₃ | 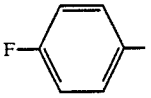 4-F-C₆H₄— | 138–139 |
| (Ia)-232 | 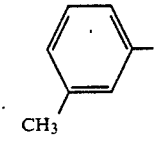 3-CH₃-C₆H₄— | CH₃ | 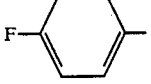 4-F-C₆H₄— | 115 |
| (Ia)-233 | 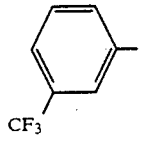 3-CF₃-C₆H₄— | CH₃ | 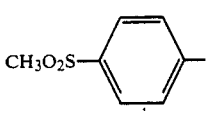 4-CH₃O₂S-C₆H₄— | 180 |
| (Ia)-234 | 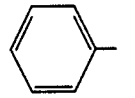 C₆H₅— | CH₃ | 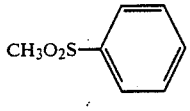 CH₃O₂S-C₆H₄— | 224 |
| (Ia)-235 | 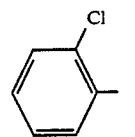 2-Cl-C₆H₄— | CH₃ | 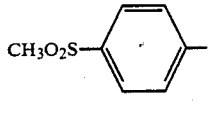 4-CH₃O₂S-C₆H₄— | 249 |
| (Ia)-236 | 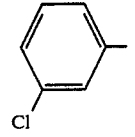 3-Cl-C₆H₄— | CH₃ | 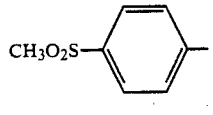 4-CH₃O₂S-C₆H₄— | 202 |
| (Ia)-237 | 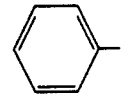 C₆H₅— | CH₃ | 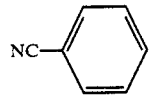 NC-C₆H₄— | 186 |

TABLE 5-continued

| Example No. | R¹ | R⁷ | Ar¹ | Melting point (°C.) |
|---|---|---|---|---|
| (Ia)-238 | 2-Cl-phenyl | CH₃ | 4-CN-phenyl | 262 |
| (Ia)-239 | 3-Cl-phenyl | CH₃ | 4-CN-phenyl | 225 |
| (Ia)-240 | 3-CF₃-phenyl | CH₃ | 3-CN-phenyl | 188 |
| (Ia)-241 | phenyl-CH₂CH₂- | CH₃ | 4-F-phenyl | 116 |
| (Ia)-242 | 2-Cl-phenyl | CH₃ | 5-NO₂-pyridin-2-yl | 310 |
| (Ia)-243 | 3-Cl-phenyl | CH₃ | 5-NO₂-pyridin-2-yl | 286 |
| (Ia)-244 | 2,5-diCl-phenyl | CH₃ | 4-F-phenyl | 186 |
| (Ia)-245 | 3-CH₃O-phenyl | CH₃ | 2,4-diF-phenyl | 178-179 |
| (Ia)-246 | 2-F-phenyl | CH₃ | 4-F-phenyl | 187-188 |
| (Ia)-247 | phenyl | CH₃ | 5-NO₂-pyridin-2-yl | 279-280 |
| (Ia)-248 | CH₃NH-C(O)- | CH₃ | 4-F-phenyl | 177-178 |

TABLE 5-continued
| Example No. | R¹ | R⁷ | Ar¹ | Melting point (°C.) |
|---|---|---|---|---|
| (Ia)-249 | CH₃ | CH₃ | 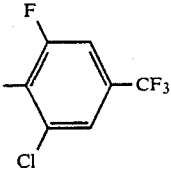 | 205 |
| (Ia)-250 | 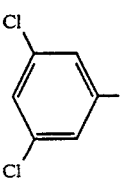 | CH₃ | 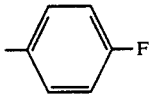 | 224–225 |
| (Ia)-251 | 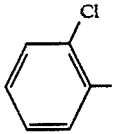 | CH₃ | 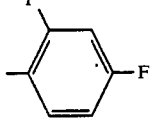 | 157 |
| (Ia)-252 | 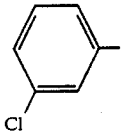 | CH₃ | 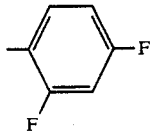 | 159 |
| (Ia)-253 | 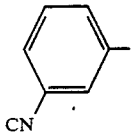 | CH₃ | 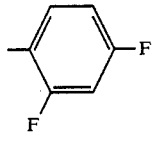 | 186 |
| (Ia)-254 | 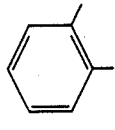 | CH₃ | 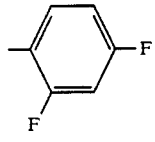 | 149 |
| (Ia)-255 | 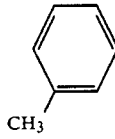 | CH₃ | 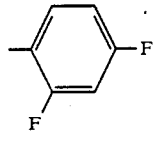 | 98 |
| (Ia)-256 | 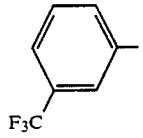 | CH₃ | 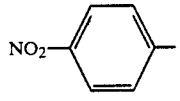 | 226 |
| (Ia)-257 | 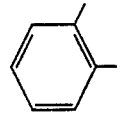 | CH₃ | 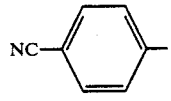 | 227 |
| (Ia)-258 | 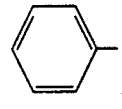 | CH₃ | 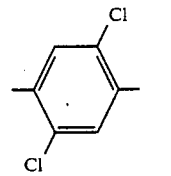 | 203 |

TABLE 5-continued

| Example No. | R¹ | R⁷ | Ar¹ | Melting point (°C.) |
|---|---|---|---|---|
| (Ia)-259 | 3-(F₃C)-C₆H₄- | CH₃ | 4-Cl-C₆H₄- | 142 |
| (Ia)-260 | 2-furyl- | CH₃ | 4-F-C₆H₄- | 154 |
| (Ia)-261 | 2-furyl-CH₂- | CH₃ | 4-F-C₆H₄- | 158–160 |
| (Ia)-262 | 3-F-C₆H₄- | CH₃ | 4-F-C₆H₄- | 176 |
| (Ia)-263 | 2,5-Cl₂-C₆H₃- | CH₃ | 4-F-C₆H₄- | 186 |
| (Ia)-264 | 2-thienyl-CH₂- | CH₃ | 4-F-C₆H₄- | 158–160 |
| (Ia)-265 | 2-CH₃-C₆H₄- | CH₃ | 4-F-C₆H₄- | 95–97 |
| (Ia)-266 | C₆H₅-C(=O)-NH- | CH₃ | 4-F-C₆H₄- | 197–200 |
| (Ia)-267 | C₆H₅-C(=O)-NH- | CH₃ | 2,4-F₂-C₆H₃- | 186 |
| (Ia)-268 | 3-Br-C₆H₄- | CH₃ | 4-F-C₆H₄- | 153 |

EXAMPLE 3

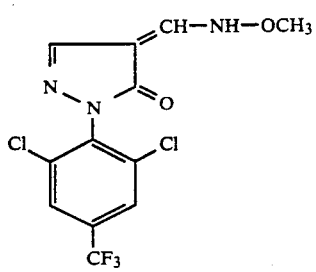

6 g (0.017 mol) of 1-(4-trifluoromethyl-2,6-dichlorophenyl)-4-N,N-dimethylamino-methylidene-pyrazolin-5-one are dissolved in 50 ml of ethanol and, after addition of 1.4 g (0.017 mol) of O-methylhydroxylamine hydrochloride, the mixture is stirred for 2 hours at room temperature. The solution is then concentrated on a rotary evaporator, and the residue is taken up with water and extracted with methylene chloride. The combined organic phases are dried and the solvent is stripped off.

3.5 g (58.2% of theory) of 1-(4-trifluoromethyl-2,6-dichloro-phenyl)-4-methyloximino-methylidene-pyrazolin-5-one of melting point 154°–160° C. are obtained.

Preparation of the Starting Substances

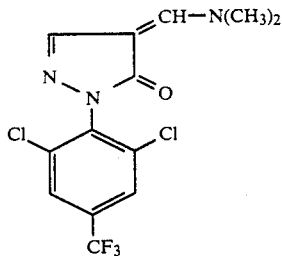

[(III-70) corresponds to a compound of the formula (Id)]

5 g (0.0179 mol) of 5-hydroxy-1-(2,6-dichloro-4-trifluoromethyl-phenyl)-pyrazole are taken up in 50 ml of toluene and, after the addition of 2.4 g (0.02 mol) of N,N-dimethylformamide dimethylacetal, the mixture is stirred at room temperature until reaction is complete (chromatographic check). The precipitated solid is filtered off with suction and stirred with petroleum ether, and the product is filtered off with suction and dried.

2.55 g (40.5% of theory) of 1-(4-trifluoromethyl-2,6-dichloro-phenyl)-4-N,N-dimethylamino-methylidenepyrazolin-5-one are obtained.

$^1$H-NMR (CDCl$_3$) [3.34 (s, 3H); 3.42 (s, 3H); 7.64 (s, 1H); 7.70 (s, 2H); 7.85 (s, 1H)

Initial Products for the Preparation of Compounds of the Formula (VI) According to Process 1

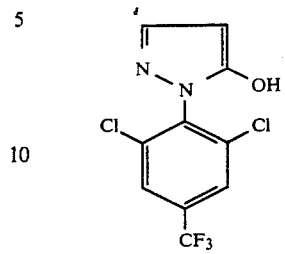

105 g (0.253 mol) of finely powdered diethyl β-(2,6-dichloro-4-trifluoromethyl-phenyl)-hydrazinomethylenemalonate are introduced in portions at 80°–85° C. with stirring into a solution of 30 g (0.75 mol) of sodium hydroxide in 1,000 ml of water, and the mixture is then stirred for a further 48 hours at 97°–98° C. The cooled reaction mixture is carefully acidified to pH 2 using concentrated hydrochloric acid and the precipitate thus obtained is filtered off with suction and dried on clay.

100 g (67% of theory) of 5-hydroxy-1-(2,6-dichloro-4-trifluoromethyl-phenyl)-pyrazole of melting point 223°–225° C. are obtained.

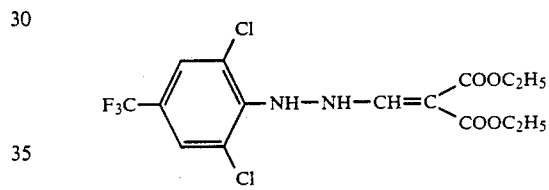

115 g (0.53 mol) of diethyl ethoxymethylenemalonate are added dropwise in the course of 30 minutes with stirring at 70°–75° C. to a solution of 122.5 g (0.5 mol) of 2,6-dichloro-4-trifluoromethyl-phenylhydrazine in 1,000 ml of ethanol, and the mixture is stirred for a further 5 hours at 70° C. to 75° C. after the end of the addition. For working up, the solvent is removed in vacuo, and the residue is triturated with water, filtered off with suction and dried on clay.

202 g (97% of theory) of diethyl β-(2,6-dichloro-4-trifluoromethylphenyl)-hydrazinomethylene-malonate of melting point 73° C.–83° C. are obtained.

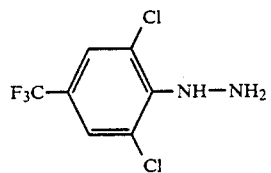

6.2 g (0.025 mol) of 3,4,5-trichloro-trifluoromethyl-benzene and 6.25 g (0.125 mol) of hydrazine hydrate are heated under reflux for 48 hours at 115°–120° C. in 12 ml of pyridine. For working up, the solvent is distilled off, and the residue is taken up in water and extracted three times with about 30 ml of dichloromethane each time. The combined organic phases are dried over magnesium sulphate and evaporated in vacuo, and the residue is then distilled.

5.1 g (83% of theory) of 2,6-dichloro-4-trifluoromethylphenylhydrazine of melting point 56° to 57° C. are obtained.

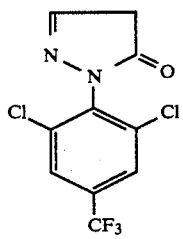

(Process 3)

240 g (0.73 mol) of methyl 1-(2,6-dichloro-4-trifluoromethyl-phenylhydrazine)-acrylate are dissolved in 730 ml of methanol and, after the addition of 151 g of 30% strength sodium methylate solution, the mixture is stirred for 20 hours at room temperature. The solution is then poured into 3 l of water and acidified using 80 ml of concentrated hydrochloric acid, and the solid is filtered off with suction, washed with water and dried.

210 g (96.9% of theory) of 1-(2,6-dichloro-4-trifluoromethyl-phenyl)-pyrazolin-5-one of melting point 228° C. are obtained.

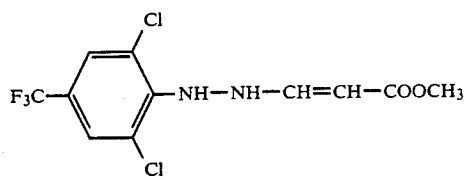
(VI-3)

2.45 g (1.0 mol) of 2,6-dichloro-4-trifluoromethylphenylhydrazine and 100 g (1.2 mol) of methyl propiolate are dissolved in 1,000 ml of toluene and the solution is stirred at 95°–100° C. for 24 hours. The solvent is then stripped off in vacuo, the residue is stirred with petroleum ether and the precipitated solid is filtered off with suction.

245 g (74.5% of theory) of methyl 1-(2,6-dichloro-4-trifluoromethylphenylhydrazine)-acrylate of melting point 70° C. are obtained.

The following end products of the formula (Ib) can be obtained analogously to the preparation example [(Ib)-1] and in correspondence with the given process:

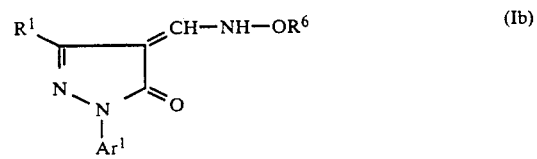
(Ib)

TABLE 6

| Example No. | $R^1$ | $R^6$ | $Ar^1$ | Melting point (°C.) |
|---|---|---|---|---|
| (Ib)-2 | CH$_3$ | CH$_3$ | 2,6-Cl$_2$-4-CF$_3$-C$_6$H$_2$ | 174 |
| (Ib)-3 | CH$_3$ | —CH$_2$CH$_3$ | 2,6-Cl$_2$-4-CF$_3$-C$_6$H$_2$ | 170 |
| (Ib)-4 | CH$_3$ | —CH$_2$CH=CH$_2$ | 2,6-Cl$_2$-4-CF$_3$-C$_6$H$_2$ | 163 |
| (Ib)-5 | CH$_3$ | —CH$_2$-C$_6$H$_4$-NO$_2$ | 2,6-Cl$_2$-4-CF$_3$-C$_6$H$_2$ | 161–162 |

TABLE 6-continued
| Example No. | R¹ | R⁶ | Ar¹ | Melting point (°C.) |
|---|---|---|---|---|
| (Ib)-6 | CH₃ | —CH(CH₃)₂ | 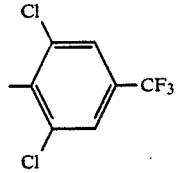 | 170 |
| (Ib)-7 | CH₃ | —CH₃ | 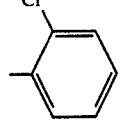 | 58 |
| (Ib)-8 | CH₃ | 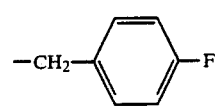 | 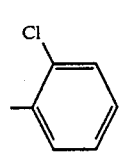 | 140* |
| (Ib)-9 | CH₃ | —CH₃ | 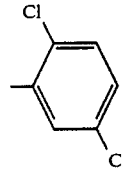 | 158–159 |
| (Ib)-10 | CH₃ | 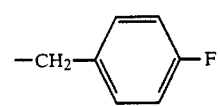 | 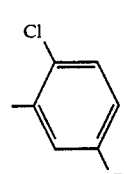 | 147* |
| (Ib)-11 | CH₃ | CH₃ | 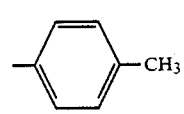 | 145 |
| (Ib)-12 | CH₃ | 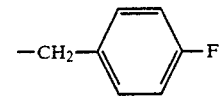 | 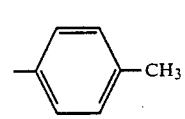 | 150–152* |
| (Ib)-13 | n-C₃H₇ | CH₃ | 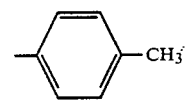 | 113 |
| (Ib)-14 | n-C₃H₇ | 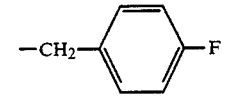 | 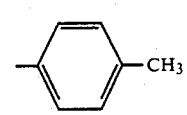 | 97* |
| (Ib)-15 | n-C₃H₇ | CH₃ | 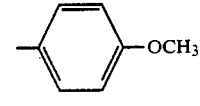 | 90 |
| (Ib)-16 | n-C₃H₇ | 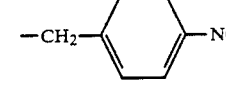 | 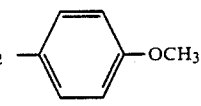 | 118–119* |

TABLE 6-continued
| Example No. | R¹ | R⁶ | Ar¹ | Melting point (°C.) |
|---|---|---|---|---|
| (Ib)-17 | —CH(CH₃)₂ | CH₃ | 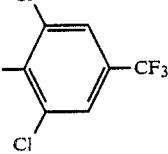 2,6-Cl₂-4-CF₃-C₆H₂ | 166 |
| (Ib)-18 | —C(CH₃)₃ | CH₃ | 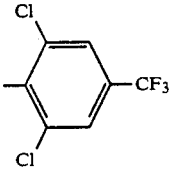 2,6-Cl₂-4-CF₃-C₆H₂ | 138 |
| (Ib)-19 | —C(CH₃)₃ | —CH₂—C₆H₄—NO₂ (p) | 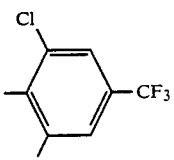 2,6-Cl₂-4-CF₃-C₆H₂ | 171–173* |
| (Ib)-20 | CH₃ | CH₃ | 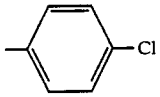 4-Cl-C₆H₄ | 150 |
| (Ib)-21 | CH₃ | —CH₂—C₆H₄—NO₂ (p) | 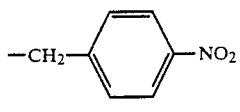 4-Cl-C₆H₄ | 212* |
| (Ib)-22 | n-C₃H₇ | CH₃ | 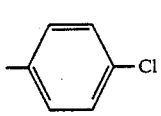 4-Cl-C₆H₄ | 131 |
| (Ib)-23 | CH₃ | CH₃ | 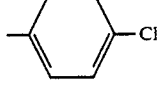 2,4,6-Cl₃-C₆H₂ | 182 |
| (Ib)-24 | n-C₃H₇ | CH₃ | 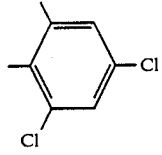 2,4,6-Cl₃-C₆H₂ | 182 |
| (Ib)-25 | n-C₃H₇ | —CH₂—C₆H₄—NO₂ (p) | 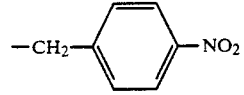 2,4,6-Cl₃-C₆H₂ | 100–104* |
| (Ib)-26 | CH₃ | CH₃ | 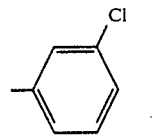 4-Cl-C₆H₄ | 130 |

TABLE 6-continued
| Example No. | R¹ | R⁶ | Ar¹ | Melting point (°C.) |
|---|---|---|---|---|
| (Ib)-27 | H | 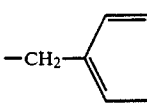 | 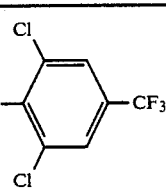 | 95–102* |
| (Ib)-28 | —CF₃ | CH₃ |  | 102 |
| (Ib)-29 | 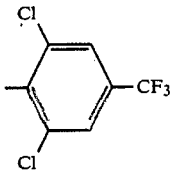 | CH₃ | 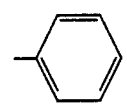 | 80–85 |
| (Ib)-30 | n-C₃H₇ | CH₃ | 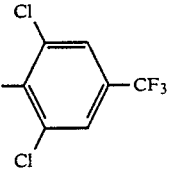 | 198 |
| (Ib)-31 | 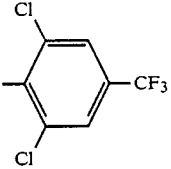 | CH₃ | 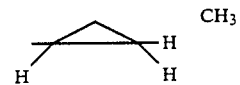 | 134 |
| (Ib)-32 | CH₃ | CH₃ | 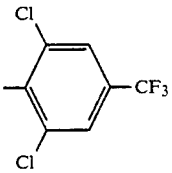 | 168 |
| (Ib)-33 | CH₃ | CH₃ | 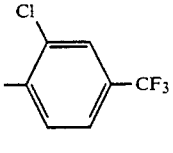 | 96 |
| (Ib)-34 | n-C₃H₇ | —C₂H₅ | 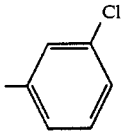 | 96 |
| (Ib)-35 | CH₃ | CH₃ |  | 161 |

TABLE 6-continued

| Example No. | R¹ | R⁶ | Ar¹ | Melting point (°C.) |
|---|---|---|---|---|
| (Ib)-36 | n-C₃H₇ | —CH₂CH=CH₂ | 3-CF₃-C₆H₄— | 48 |
| (Ib)-37 | —CH₂—CH(CH₃)₂ | —CH₂CH=CH₂ | 4-Cl-C₆H₄— | 105 |
| (Ib)-38 | C₆H₅— | —CH₂CH=CH₂ | 4-Cl-C₆H₄— | 88 |
| (Ib)-39 | CH₃ | —CH₂CH=CH₂ | 4-Cl-C₆H₄— | 119 |
| (Ib)-40 | CH₃ | —CH₂CH=CH₂ | 3-Cl-C₆H₄— | 63 |
| (Ib)-41 | CF₃ | —CH₂CH=CH₂ | 2,6-Cl₂-4-CF₃-C₆H₂— | $n_D^{23}$ = 1.5192 |
| (Ib)-42 | CH₃ | —CH₂CH=CH₂ | 4-CH₃-C₆H₄— | 103 |
| (Ib)-43 | CH₃ | —CH₂CH=CH₂ | 4-NO₂-C₆H₄— | 118 |
| (Ib)-44 | —C(CH₃)₃ | —CH₂CH=CH₂ | 2,6-Cl₂-4-CF₃-C₆H₂— | 67 |
| (Ib)-45 | n-C₃H₇ | —CH₂CH=CH₂ | 2,6-Cl₂-4-CF₃-C₆H₂— | 149 |
| (Ib)-46 | cyclopropyl | —CH₂CH=CH₂ | 2,6-Cl₂-4-CF₃-C₆H₂— | 106 |

TABLE 6-continued

| Example No. | R¹ | R⁶ | Ar¹ | Melting point (°C.) |
|---|---|---|---|---|
| (Ib)-47 | $CH_3$ | $-CH_2CH=CH_2$ | 2,6-dimethylphenyl | 126–127 |
| (Ib)-48 | $-CH(CH_3)_2$ | $-CH_2CH=CH_2$ | 4-chlorophenyl | 91 |
| (Ib)-49 | n-$C_3H_7$ | $-CH_2CH=CH_2$ | 4-$OCF_3$-phenyl | 53 |
| (Ib)-50 | $CH_3$ | $-CH_2CH=CH_2$ | 4-$OCF_3$-phenyl | 83 |
| (Ib)-51 | $-C_2H_5$ | $-CH_2CH=CH_2$ | 3-$CF_3$-phenyl | 71–72 |
| (Ib)-52 | $-CF_3$ | $-CH_2CH=CH_2$ | 4-chlorophenyl | 34 |
| (Ib)-53 | $CH_3$ | $-CH_2CH=CH_2$ | 3-$NO_2$-phenyl | 68–70 |
| (Ib)-54 | n-$C_3H_7$ | $-CH_2CH=CH_2$ | 2-(CH₃C(=N-)S-)-4-$NO_2$-phenyl | 170 (decomposition) |
| (Ib)-55 | n-$C_3H_7$ | $-CH_2CH=CH_2$ | 3,5-bis($CF_3$)-4-Cl-phenyl | 68 |
| (Ib)-56 | $CH_3$ | $-CH_2CH=CH_2$ | 3,5-dichloro-2,6-difluoro-4-cyanophenyl | 120 |
| (Ib)-57 | n-$C_3H_7$ | $CH_3$ | 4-fluorophenyl | 124 |

TABLE 6-continued
| Example No. | R¹ | R⁶ | Ar¹ | Melting point (°C.) |
|---|---|---|---|---|
| (Ib)-58 | n-C₃H₇ | CH₃ | 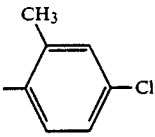 | 147–149 |
| (Ib)-59 | CH₃ | CH₃ | 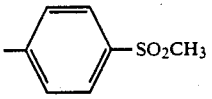 | 166 (decomposition) |
| (Ib)-60 | CH₃ | CH₃ |  | 146 |
| (Ib)-61 | —CH₂SCH₃ | H | 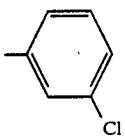 | 150 |
| (Ib)-62 | —CH₃SCH₃ | H | 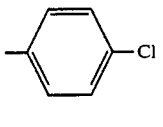 | 146 |
| (Ib)-63 | —CH₂SCH₃ | H | 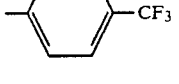 | 134 |
| (Ib)-64 | —CH₂SCH₃ | H | 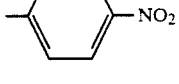 | 209 |
| (Ib)-65 | —CH₂SCH₃ | CH₃ | 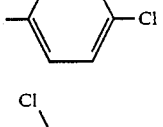 | 102 |
| (Ib)-66 | —CH₂SCH₃ | CH₃ | 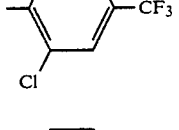 | 105 |
| (Ib)-67 | —CH₂SCH₃ | CH₃ | 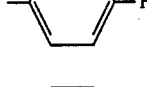 | 64 |
| (Ib)-68 | —CH₂SCH₃ | CH₃ | 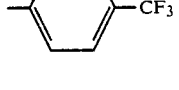 | 91 |
| (Ib)-69 | —CH₂SCH₃ | —CH₂CH=CH₂ | 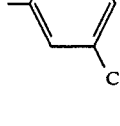 | OIL |

TABLE 6-continued

| Example No. | R¹ | R⁶ | Ar¹ | Melting point (°C.) |
|---|---|---|---|---|
| (Ib)-70 | —CH₂SCH₃ | —CH₂CH=CH₂ | 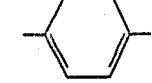 4-Cl-C₆H₄ | 68 |
| (Ib)-71 | —CH₂SCH₃ | —CH₂CH=CH₂ | 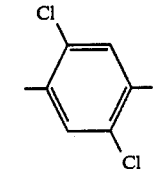 2,4,5-trichlorophenyl | 95 |
| (Ib)-72 | —CH₂SCH₃ | —CH₂CH=CH₂ | 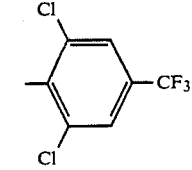 2,6-dichloro-4-CF₃-phenyl | Oil |
| (Ib)-73 | 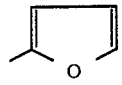 2-furyl | CH₃ |  4-NO₂-C₆H₄ | 178–180 |
| (Ib)-74 | CH₃ | CH₃ | 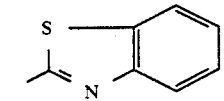 benzothiazol-2-yl | 181–182 |
| (Ib)-75 | 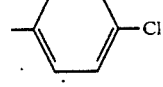 4-Cl-C₆H₄ | CH₃ | 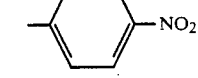 4-NO₂-C₆H₄ | 210–211 |
| (Ib)-76 |  4-Cl-C₆H₄ | CH₃ | 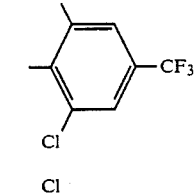 2,6-dichloro-4-CF₃-phenyl | 167–168 |
| (Ib)-77 | 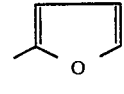 2-furyl | CH₃ | 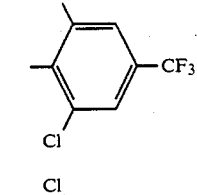 2,6-dichloro-4-CF₃-phenyl | 126 |
| (Ib)-78 | n-C₃H₇ | CH₃ | 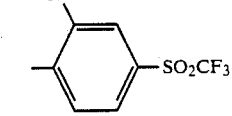 2-Cl-4-SO₂CF₃-phenyl | 105–107 |
| (Ib)-79 | n-C₃H₇ | CH₃ | 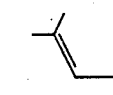 2-pyridyl | 65 |
| (Ib)-80 | —CH₂SC₂H₅ | CH₃ | 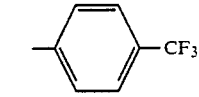 4-CF₃-C₆H₄ | 67 |

TABLE 6-continued
| Example No. | R¹ | R⁶ | Ar¹ | Melting point (°C.) |
|---|---|---|---|---|
| (Ib)-81 | —CH$_2$SC$_2$H$_5$ | CH$_3$ | 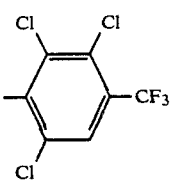 | 60–65 |
| (Ib)-82 | CH$_3$ | CH$_3$ | 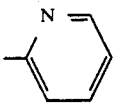 | 164 |
| (Ib)-83 | 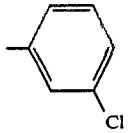 | CH$_3$ | 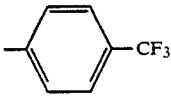 | 60 |
| (Ib)-84 | 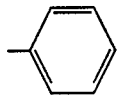 | CH$_3$ | 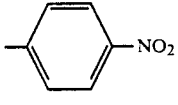 | 174–176 |
| (Ib)-85 | 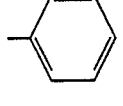 | CH$_3$ | 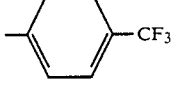 | 104 |
| (Ib)-86 | CH$_3$ | CH$_3$ |  | 157 |
| (Ib)-87 | n-C$_3$H$_7$ | CH$_3$ | 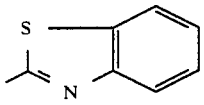 | 148 |
| (Ib)-88 | 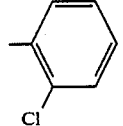 | CH$_3$ | 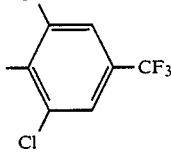 | 55–60 |
| (Ib)-89 | —CH$_2$SC$_2$H$_5$ | CH$_3$ | 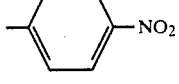 | 124–128 |
| (Ib)-90 | 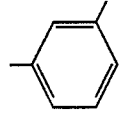 | CH$_3$ | 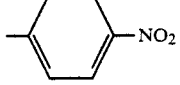 | 185–186 |
| (Ib)-91 | 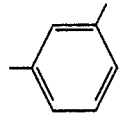 | CH$_3$ | 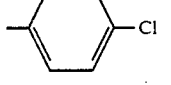 | 134–136 |

TABLE 6-continued

| Example No. | R¹ | R⁶ | Ar¹ | Melting point (°C.) |
|---|---|---|---|---|
| (Ib)-92 | n-C₃H₇ | C₂H₅ | 2-pyridyl | 61 |
| (Ib)-93 | n-C₃H₇ | —CH₂—CH=CH₂ | 2-pyridyl | 56 |

The compounds marked * exist as dimethylamine salts.

EXAMPLE 4

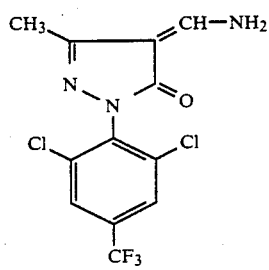

[(Ic)-1]

(Variation [(Ic)-α]

10 g (0.0273 mol) of 1-(4-trifluoromethyl-2,6-dichlorophenyl)-3-methyl-4-N,N-dimethylamino-methylidenepyrazolin-5-one are suspended in 40 ml of toluene, and ammonia is passed in at 80° C. until the reaction is complete (chromatographic check). The mixture is then cooled to 0° C., and the solid is filtered off with suction, washed with petroleum ether/ether 2:1 and dried.

6.2 g (67.2% of theory) of 1-(4-trifluoromethyl-2,6-dichlorophenyl)-3-methyl-4-aminomethylidene-pyrazolin-5-one of melting point 184°–185° C. are obtained.

EXAMPLE 5

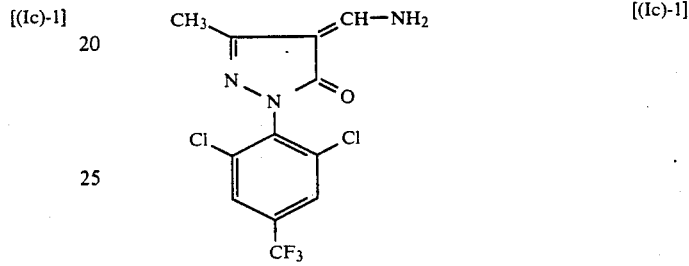

[(Ic)-1]

[Variation [(Ic)-β]

The solution of 27.5 g (0.105 mol) of 1-(4-trifluoromethyl-2,6-dichlorophenyl)-3-methyl-pyrazolin-5-one in 500 ml of absolute ethanol is added dropwise in the course of 8 hours to a solution of 5.67 g (0.07 mol) of s-triazine in 100 ml of absolute ethanol. The solution is then stirred overnight at room temperature and is evaporated to dryness. The remaining oil is purified by column chromatography on silica gel (eluent: chloroform and 20% methanol).

17.9 g (50.4% of theory) of 1-(4-trifluoromethyl-2,6-dichlorophenyl)-3-methyl-4-aminomethylidene-pyrazolin-5-one of melting point 184°–185° C. are obtained.

The following end products of the formula (I-c) can be obtained analogously to the preparation example [(Ic)-1] and in correspondence with the given processes:

TABLE 7

(Ic)

| Example No. | R¹ | Ar¹ | Melting point (°C.) |
|---|---|---|---|
| (Ic)-2 | H | 2,5-dichloro-4-CF₃-phenyl | 243 |
| (Ic)-3 | CH₃ | phenyl | 151 |

TABLE 7-continued (Ic) structure: pyrazolone with R¹ at 5-position, =CH-NH₂ at 4-position, Ar¹ on N1, C=O at 3-position.

| Example No. | R¹ | Ar¹ | Melting point (°C.) |
|---|---|---|---|
| (Ic)-4 | n-C₃H₇ | phenyl | 130 |
| (Ic)-5 | n-C₃H₇ | 2,4,6-trichlorophenyl | 167 |
| (Ic)-6 | CH₃ | 2,4,6-trichlorophenyl | 204 |
| (Ic)-7 | n-C₃H₇ | 4-nitrophenyl | 291–294 |
| (Ic)-8 | CH₃ | 4-methylphenyl | 179 |
| (Ic)-9 | CH₃ | 2-chlorophenyl | 163–164 |
| (Ic)-10 | CH₃ | 2,5-dichlorophenyl | 204 |
| (Ic)-11 | n-C₃H₇ | 4-methylphenyl | 117 |
| (Ic)-12 | —C₂H₅ | 2,6-dichloro-4-trifluoromethylphenyl | 65 |

TABLE 7-continued
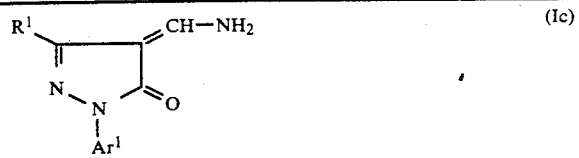
(Ic)
| Example No. | R¹ | Ar¹ | Melting point (°C.) |
|---|---|---|---|
| (Ic)-13 | —CH(CH₃)₂ | 2,6-Cl₂-4-CF₃-C₆H₂ | 73 |
| (Ic)-14 | —C(CH₃)₃ | 2,6-Cl₂-4-CF₃-C₆H₂ | 253 |
| (Ic)-15 | cyclohexyl | 2,6-Cl₂-4-CF₃-C₆H₂ | 86–88 |
| (Ic)-16 | —CF₃ | 2,6-Cl₂-4-CF₃-C₆H₂ | 187 |
| (Ic)-17 | CH₃ | 3-Cl-C₆H₄ | 286 |
| (Ic)-18 | CH₃ | 4-Cl-C₆H₄ | 170 |
| (Ic)-19 | n-C₃H₇ | 4-Cl-C₆H₄ | 122 |
| (Ic)-20 | cyclopropyl | 2,6-Cl₂-4-CF₃-C₆H₂ | 171 |
| (Ic)-21 | phenyl | 2,6-Cl₂-4-CF₃-C₆H₂ | 221 |

TABLE 7-continued
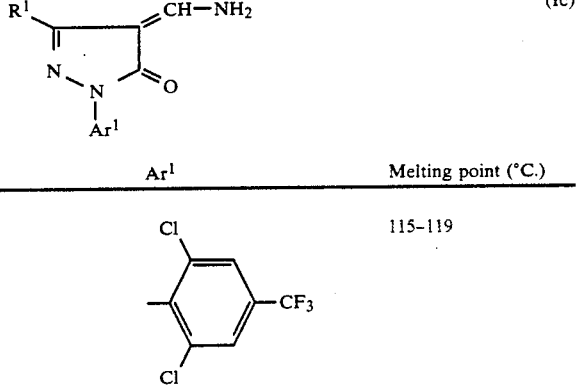
(Ic)
| Example No. | R¹ | Ar¹ | Melting point (°C.) |
|---|---|---|---|
| (Ic)-16 | n-C₃H₇ | 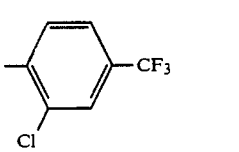 | 115–119 |
| (Ic)-23 | CH₃ | 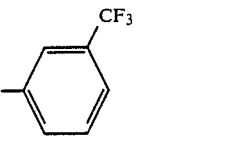 | 102–109 |
| (Ic)-24 | CH₃ | 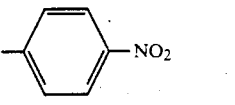 | 138 |
| (Ic)-25 | CH₃ | 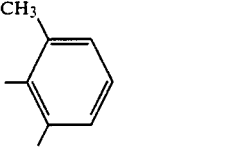 | >300 |
| (Ic)-26 | CH₃ | 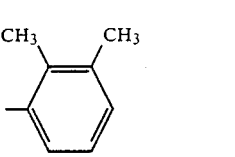 | 187 |
| (Ic)-27 | n-C₃H₇ | 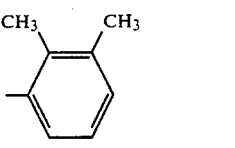 | 180 |
| (Ic)-28 | CH₃ | 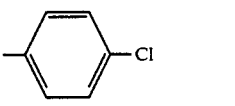 | 172–176 |
| (Ic)-29 | 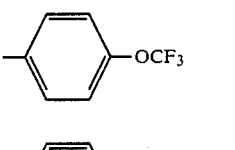 | 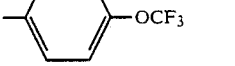 | 167–169 |
| (Ic)-30 | CH₃ | —⟨◯⟩—OCF₃ | 136 |
| (Ic)-31 | C₂H₅ | —⟨◯⟩—OCF₃ | 126–127 |

TABLE 7-continued
(Ic)
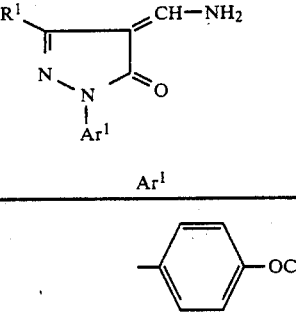
| Example No. | R$^1$ | Ar$^1$ | Melting point (°C.) |
|---|---|---|---|
| (Ic)-32 | n-C$_3$H$_7$ | 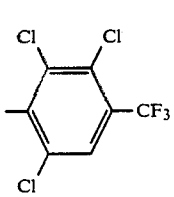 | 77–78 |
| (Ic)-33 | CH$_3$ | 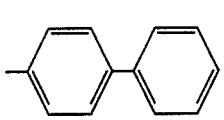 | 65 |
| (Ic)-34 | n-C$_3$H$_7$ | 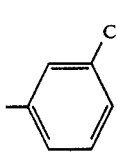 | 172 |
| (Ic)-35 | C$_2$H$_5$ |  | 93 |
| (Ic)-36 | —CH$_2$OCH$_3$ | 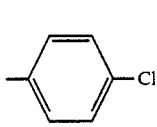 | 134–135 |
| (Ic)-37 | —CF$_3$ | 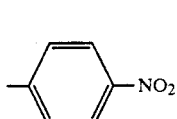 | 191–192 |
| (Ic)-38 | 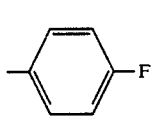 | 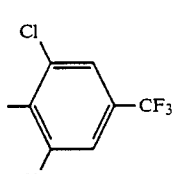 | >320 |
| (Ic)-39 | n-C$_3$H$_7$ | 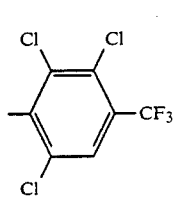 | 56–58 |
| (Ic)-40 | —CH$_2$SCH$_3$ | (2,6-Cl$_2$-4-CF$_3$-phenyl) | 222 |
| (Ic)-41 | —CH$_2$SCH$_3$ | (2,5-Cl$_2$-3-CF$_3$-phenyl) | 147 |

TABLE 7-continued
(Ic)
| Example No. | R¹ | Ar¹ | Melting point (°C.) |
|---|---|---|---|
| (Ic)-42 | —CH$_2$SCH$_3$ | 4-Cl-C$_6$H$_4$ | 116 |
| (Ic)-43 | —CH$_2$SCH$_3$ | 4-NO$_2$-C$_6$H$_4$ | >260 |
| (Ic)-44 | —CH$_2$SCH$_3$ | 4-CF$_3$-C$_6$H$_4$ | 131 |
| (Ic)-45 | —CH$_2$SCH$_3$ | 2,4,5-Cl$_3$-C$_6$H$_2$ | 80 |
| (Ic)-46 | H | 2,4,5-Cl$_3$-C$_6$H$_2$ | 255–256 |
| (Ic)-47 | CH$_3$ | 2,4,5-Cl$_3$-C$_6$H$_2$ | 50–52 |
| (Ic)-48 | 3,4-Cl$_2$-C$_6$H$_3$ | 2,6-Cl$_2$-4-CF$_3$-C$_6$H$_2$ | 201–203 |
| (Ic)-49 | 2-furyl | 2,6-Cl$_2$-4-CF$_3$-C$_6$H$_2$ | 181–184 |
| (Ic)-50 | 3-Cl-C$_6$H$_4$ | 2,6-Cl$_2$-4-CF$_3$-C$_6$H$_2$ | 144 |

TABLE 7-continued (Ic): 1-Ar¹-pyrazol-5(4H)-one with R¹ at 3-position and =CH-NH₂ at 4-position

| Example No. | R¹ | Ar¹ | Melting point (°C.) |
|---|---|---|---|
| (Ic)-51 | 4-CH₃-C₆H₄- | 4-NO₂-C₆H₄- | >320 |
| (Ic)-52 | 4-Cl-C₆H₄- | 2,6-diCl-4-CF₃-C₆H₂- | 241 |
| (Ic)-53 | 4-CH₃-C₆H₄- | 4-Cl-C₆H₄- | 204 |
| (Ic)-54 | 3-Cl-C₆H₄- | 4-Cl-C₆H₄- | 189 |
| (Ic)-55 | 3-Cl-C₆H₄- | 4-NO₂-C₆H₄- | >320 |
| (Ic)-56 | —CH₂SC₂H₅ | 4-F-C₆H₄- | 92 |
| (Ic)-57 | n-C₃H₇ | 2-CH₃-4-Cl-C₆H₃- | 110–114 |
| (Ic)-58 | —CH₂SC₂H₅ | 4-CF₃-C₆H₄- | 75–79 |
| (Ic)-59 | CH₃ | 2-pyridyl | 242 |
| (Ic)-60 | n-C₃H₇ | 2-pyridyl | 202 |

TABLE 7-continued
(Ic)
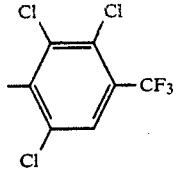
| Example No. | R¹ | Ar¹ | Melting point (°C.) |
|---|---|---|---|
| (Ic)-61 | —CH$_2$SC$_2$H$_5$ | 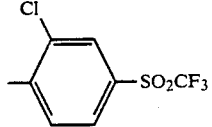 | 70 |
| (Ic)-62 | n-C$_3$H$_7$ | 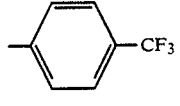 | 40–45 |
| (Ic)-63 | 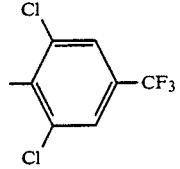 | 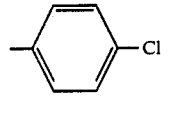 | 157 |
| (Ic)-64 | 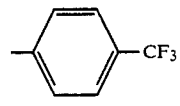 | 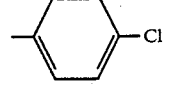 | 189–190 |
| (Ic)-65 | 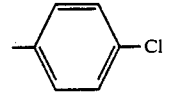 | 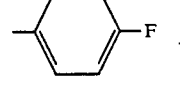 | 214–216 |
| (Ic)-66 | 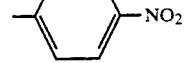 | (4-CF$_3$-phenyl) | 160–166 |
| (Ic)-67 | (3,4-diCl-phenyl) | (4-Cl-phenyl) | 227 |
| (Ic)-68 | —CH$_2$CO$_2$C$_2$H$_5$ | (4-Cl-phenyl) | 136 |
| (Ic)-69 | (phenyl) | (4-F-phenyl) | 156 |
| (Ic)-70 | (2-furyl) | (4-NO$_2$-phenyl) | 309 |

TABLE 7-continued
(Ic) 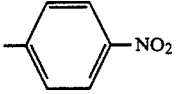
| Example No. | R¹ | Ar¹ | Melting point (°C.) |
|---|---|---|---|
| (Ic)-71 | —CH$_2$SC$_2$H$_5$ |  | 247–249 |
| (Ic)-72 | n-C$_3$H$_7$ | 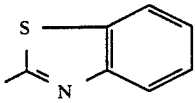 | 118–120 |
| (Ic)-73 | n-C$_3$H$_7$ | 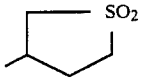 | 247–249 |
| (Ic)-74 | CH$_3$ | 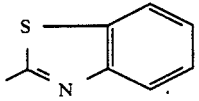 | 200–202 |
| (Ic)-75 | CH$_3$ |  | 270–274 |
| (Ic)-76 | 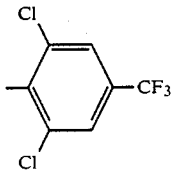 |  | 58 |
| (Ic)-77 | CH$_3$ | 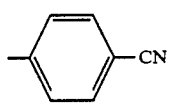 | 138–140 |
| (Ic)-78 | n-C$_3$H$_7$ | 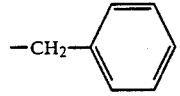 | 211 |
| (Ic)-79 | 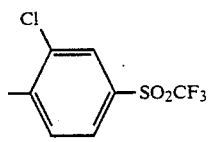 | 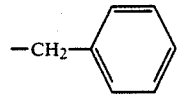 | 47 |
| (Ic)-80 |  | 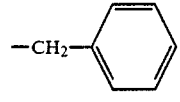 | 118 |
| (Ic)-81 | —CH$_2$— | 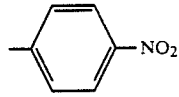 | 283 |

TABLE 7-continued
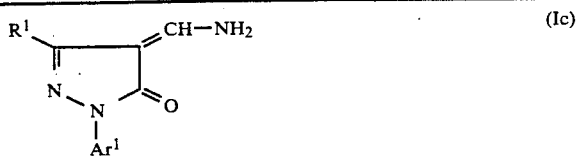
(Ic)
| Example No. | $R^1$ | $Ar^1$ | Melting point (°C.) |
|---|---|---|---|
| (Ic)-82 | —CH$_2$—C$_6$H$_5$ | 2,6-Cl$_2$-4-CF$_3$-C$_6$H$_2$— | 156 |
| (Ic)-83 | n-C$_3$H$_7$ | 4-SO$_2$CF$_3$-C$_6$H$_4$— | 196 |
| (Ic)-84 | H | 2,3,6-Cl$_3$-4-CF$_3$-C$_6$H— | 253–262 |
| (Ic)-85 | H | 4-Cl-C$_6$H$_4$— | 179 |
| (Ic)-86 | H | C$_6$H$_5$— | 124 |
| (Ic)-87 | C$_6$H$_5$— | 4-SO$_2$CF$_3$-C$_6$H$_4$— | 217 |
| (Ic)-88 | H | 3-Cl-C$_6$H$_4$— | 160 |
| (Ic)-89 | C$_3$H$_7$ | 4-CO$_2$CH$_3$-C$_6$H$_4$— | 127 |
| (Ic)-90 | —CH$_2$—C$_6$H$_5$ | 4-F-C$_6$H$_4$— | 85 |
| (Ic)-91 | 3-Cl-C$_6$H$_4$— | 4-F-C$_6$H$_4$— | 137–139 |

TABLE 7-continued $$\text{(Ic)}$$

Structure: pyrazolone with R¹ at 5-position, =CH-NH₂ at 4-position, N-Ar¹ at 1-position, C=O at 3-position.

| Example No. | R¹ | Ar¹ | Melting point (°C.) |
|---|---|---|---|
| (Ic)-92 | 2-Cl-phenyl | 4-F-phenyl | 179 |
| (Ic)-93 | -CH₂-(2-Cl-phenyl) | 4-F-phenyl | 65–66 |
| (Ic)-94 | -CH₂-(3-Cl-phenyl) | 2,6-diCl-4-CF₃-phenyl | 156 |
| (Ic)-95 | -CH₂-(3-Cl-phenyl) | 4-F-phenyl | 111 |
| (Ic)-96 | -CH₂-(4-Cl-phenyl) | 2,6-diCl-4-CF₃-phenyl | 190–192 |
| (Ic)-97 | -CH₂-(4-Cl-phenyl) | 4-F-phenyl | 131–133 |
| (Ic)-98 | 2,4-diCl-phenyl | 4-F-phenyl | 202 |
| (Ic)-99 | phenyl | 3-CF₃-phenyl | 154 |
| (Ic)-100 | CH₃ | 3,5-diCl-phenyl | 215 |

TABLE 7-continued (Ic)

structure: pyrazolone with R¹ at 5-position, =CH—NH₂ at 4-position, Ar¹ on N1, C=O at 3-position

| Example No. | R¹ | Ar¹ | Melting point (°C.) |
|---|---|---|---|
| (Ic)-101 | n-C₃H₇ | 3,5-dichlorophenyl | 134 |
| (Ic)-102 | phenyl | 3,5-dichlorophenyl | 223 |
| (Ic)-103 | n-C₃H₇ | 2,4-difluorophenyl | 92 |
| (Ic)-104 | phenyl | 2,4-difluorophenyl | 132 |
| (Ic)-105 | CH₃ | 2,4-difluorophenyl | 152 |
| (Ic)-106 | 3-(CF₃)phenyl | 4-fluorophenyl | 114 |
| (Ic)-107 | phenyl | phenyl | 166 |
| (Ic)-108 | —CH₂S—(4-Cl-phenyl) | 4-fluorophenyl | 117 |
| (Ic)-109 | —CH₂—(3-CF₃-phenyl) | 4-fluorophenyl | 110 |
| (Ic)-110 | —CH₂—C(CH₃)₃ | 4-fluorophenyl | 104 |

TABLE 7-continued $$\text{(Ic)}$$

Structure (Ic): pyrazolone with R¹ at 4-position, CH—NH₂ (=CH-NH₂) at 3-position substituent, N-N-Ar¹, C=O.

| Example No. | R¹ | Ar¹ | Melting point (°C.) |
|---|---|---|---|
| (Ic)-111 | —S—CH₂—(4-Cl-C₆H₄) | 2,6-Cl₂-4-CF₃-C₆H₂ | 176 |
| (Ic)-112 | —CH₂—(3-CF₃-C₆H₄) | C₆H₅ | 123 |
| (Ic)-113 | —CH₂—(3-CF₃-C₆H₄) | 2,4-F₂-C₆H₃ | 79–82 |
| (Ic)-114 | —CH₂—C₆H₅ | 2,4-F₂-C₆H₃ | 71 |
| (Ic)-115 | C₆H₅ | 2-Cl-4-SO₂CF₃-C₆H₃ | 138 |
| (Ic)-116 | —OC₂H₅ | 2,6-Cl₂-4-CF₃-C₆H₂ | 142 |
| (Ic)-117 | —NH—CO—CH₃ | 2,6-Cl₂-4-CF₃-C₆H₂ | 237 |
| (Ic)-118 | —NH—CO—C₆H₅ | 2,6-Cl₂-4-CF₃-C₆H₂ | 145–150 |
| (Ic)-119 | —NH—CO—C₆H₅ | C₆H₅ | 168–175 |

TABLE 7-continued

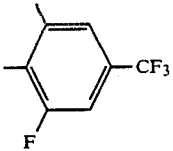

| Example No. | R¹ | Ar¹ | Melting point (°C.) |
|---|---|---|---|
| (Ic)-120 | CH₃ | 2-Cl, 4-CF₃, 5-F-phenyl | 205 |

The following starting products of the formula (III), which at the same time in part are end products of the formula (Id) according to the invention, are obtained analogously to the preparation examples (II-1), (III-69) and (III-70):

TABLE 8

(III) structure: R¹ and CH—N(CH₃)₂ on pyrazolone ring with N-Ar

| Example No. | R¹ | Ar | Refractive index ($n_D^{20}$); melting point (°C.) |
|---|---|---|---|
| III-2 | CH₃ | phenyl | 127 |
| III-3 | n-C₃H₇ | 2,4,6-trichlorophenyl | 164 |
| III-4 | n-C₃H₇ | phenyl | 107 |
| III-5 | CH₃ | 2,4,6-trichlorophenyl | 196 |
| III-6 | C₂H₅ | 2,6-dichloro-4-CF₃-phenyl | 111–113 |
| III-7 | CH₃ | 4-methylphenyl | 206 |

TABLE 8-continued
$$\underset{Ar}{\underset{N}{\overset{R^1}{\bigvee}}\underset{\|}{\overset{CH-N(CH_3)_2}{\bigvee}}}\quad(III)$$
| Example No. | R¹ | Ar | |
|---|---|---|---|
| III-8 | CH₃ | 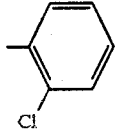 2-Cl-C₆H₄ | 170 |
| III-9 | CH₃ | 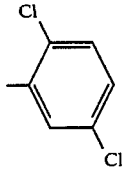 2,5-Cl₂-C₆H₃ | 128 |
| III-10 | —CH(CH₃)₂ | 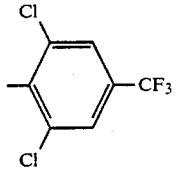 2,6-Cl₂-4-CF₃-C₆H₂ | 114 |
| III-11 | 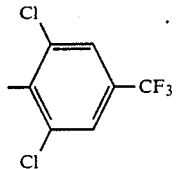 cyclohexyl (H) | 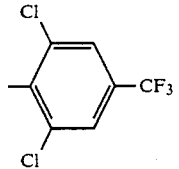 2,6-Cl₂-4-CF₃-C₆H₂ | 151–156 |
| III-12 | —CF₃ | 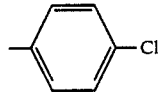 2,6-Cl₂-4-CF₃-C₆H₂ | 139 |
| III-13 | CH₃ | 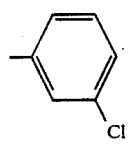 4-Cl-C₆H₄ | 200 |
| III-14 | CH₃ | 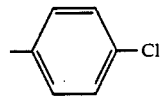 3-Cl-C₆H₄ | 133 |
| III-15 | n-C₃H₇ | 4-Cl-C₆H₄ | 121 |
| III-16 | n-C₃H₇ | 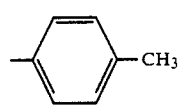 4-CH₃-C₆H₄ | 134 |

TABLE 8-continued $$\underset{Ar}{\overset{R^1}{\underset{N}{\bigvee}}}\overset{CH-N(CH_3)_2}{\underset{O}{\bigvee}}\quad (III)$$

| Example No. | R¹ | Ar | |
|---|---|---|---|
| III-17 | n-C₃H₇ | —⟨⟩—OCH₃ (4-methoxyphenyl) | 117 |
| III-18 | —C(CH₃)₃ | 2,6-dichloro-4-(trifluoromethyl)phenyl | 173 |
| III-19 | phenyl | 2,6-dichloro-4-(trifluoromethyl)phenyl | 132–134 |
| III-20 | n-C₃H₇ | 2,6-dichloro-4-(trifluoromethyl)phenyl | 113–115 |
| III-21 | cyclopropyl | 2,6-dichloro-4-(trifluoromethyl)phenyl | 183–184 |
| III-22 | CH₃ | 2,6-dimethylphenyl | 166 |
| III-23 | C₂H₅ | 4-(trifluoromethoxy)phenyl | 82–85 |
| III-24 | n-C₃H₇ | 4-(trifluoromethoxy)phenyl | 116–117 |
| III-25 | C₂H₅ | 3-(trifluoromethyl)phenyl | 125 |

TABLE 8-continued
$$\underset{Ar}{\overset{R^1}{\underset{N-N}{\bigg|}}}\overset{CH=N(CH_3)_2}{\underset{O}{\bigg|}} \quad (III)$$
| Example No. | R¹ | Ar | |
|---|---|---|---|
| III-26 | CH₂OCH₃ | 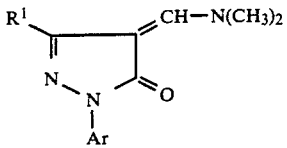 4-Cl-C₆H₄ | 163 |
| III-27 | CH₃ | 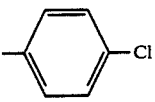 3-NO₂-C₆H₄ | 181–182 |
| III-28 | CF₃ | 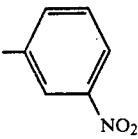 4-Cl-C₆H₄ | 182 |
| III-29 | CH₃ | 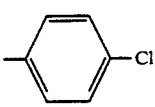 3,5-Cl₂-2,6-F₂-4-CN-C₆ | 132 |
| III-30 | —CH₂OCH₃ | 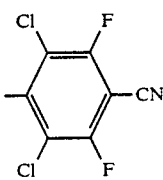 4-NO₂-C₆H₄ | 86 |
| III-31 | n-C₃H₇ | 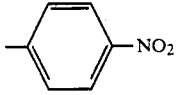 2-CF₃-4-CF₃-5-Cl-C₆H₂ | 131–132 |
| III-32 | 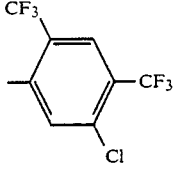 C₆H₅ | 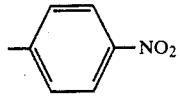 4-NO₂-C₆H₄ | 210–212 |
| III-33 | n-C₃H₇ | 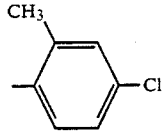 2-CH₃-4-Cl-C₆H₃ | 1,5983 |
| III-34 | n-C₃H₇ | 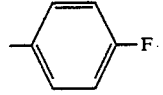 4-F-C₆H₄ | 134–137 |
| III-35 | C₆H₅ | 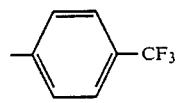 4-CF₃-C₆H₄ | 156–158 |

TABLE 8-continued
(III)
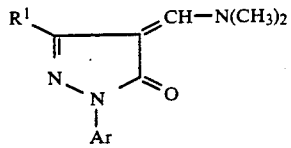
| Example No. | R¹ | Ar | |
|---|---|---|---|
| III-36 | n-C$_3$H$_7$ | 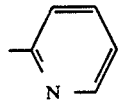 | 182 |
| III-37 | CH$_3$ | 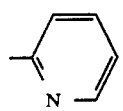 | 180 |
| III-38 | n-C$_3$H$_7$ | 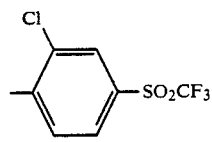 | 138–142 |
| III-39 | CH$_3$ | 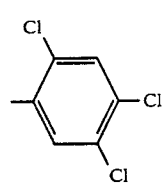 | 127 |
| III-40 | n-C$_3$H$_7$ | 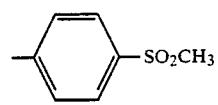 | 157 |
| III-41 | CH$_3$ | 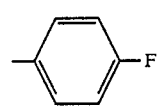 | 175 |
| III-42 | 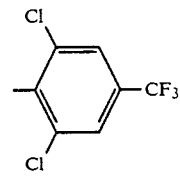 | 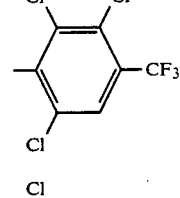 | 204–205 |
| III-43 | —CH$_2$SC$_2$H$_5$ | 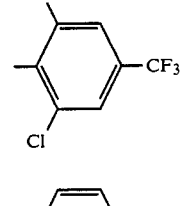 | 90–92 |
| III-44 | 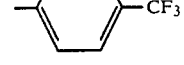 | 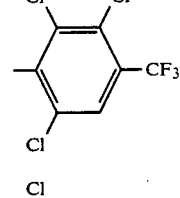 | 195–196 |
| III-45 | —CH$_2$SC$_2$H$_5$ | 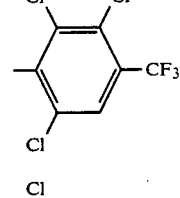 | 114–115 |

TABLE 8-continued
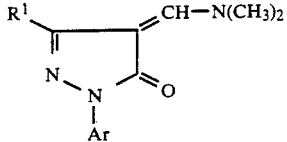
(III)
| Example No. | R¹ | Ar | |
|---|---|---|---|
| III-46 | 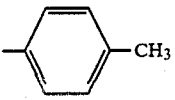 | 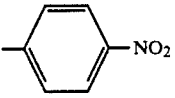 | 253-254 |
| III-47 | 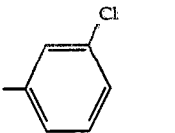 | 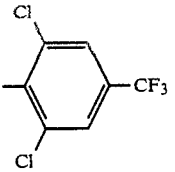 | 146 |
| III-48 | 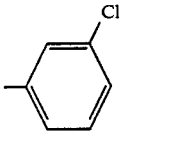 | 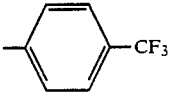 | 135-138 |
| III-49 | 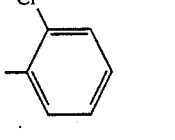 | 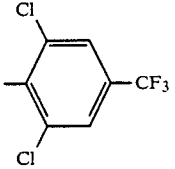 | 171-173 |
| III-50 | 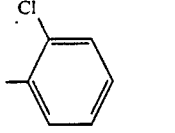 | 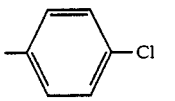 | 145 |
| III-51 | 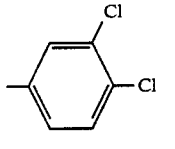 | 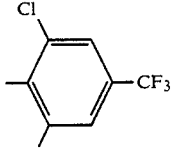 | 207 |
| III-52 | 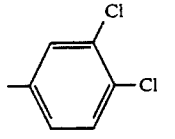 | 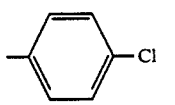 | 174 |
| III-53 | —CH$_2$SCH$_3$ | 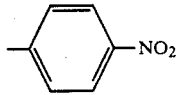 | 187 |
| III-54 | —CH$_2$SCH$_3$ | 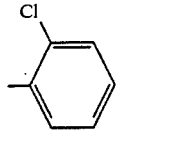 | 112 |

TABLE 8-continued
$$\text{(III)}$$
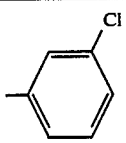
| Example No. | R¹ | Ar | |
|---|---|---|---|
| III-55 | —CH₂SCH₃ |  | Oil |
| III-56 | —CH₂SCH₃ | 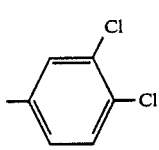 | 157 |
| III-57 | —CH₂SCH₃ | 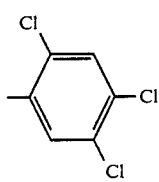 | 188 |
| III-58 | —CH₂SCH₃ | 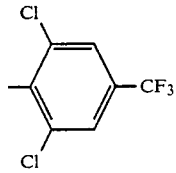 | 140 |
| III-59 | —CH₂SCH₃ |  | 175 |
| III-60 | —CH₂SCH₃ | 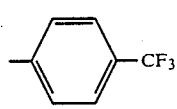 | 151 |
| III-61 | —CH₂SCH₃ | 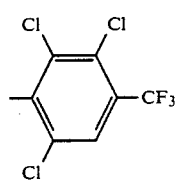 | 170 |
| III-62 | —CH₂SCH₃ | 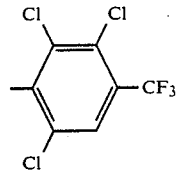 | 158 |
| III-63 | H | 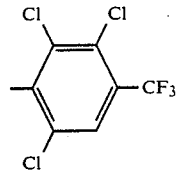 | 226 |

TABLE 8-continued $$\text{(III)}$$

Structure: pyrazolone with R¹ at 5-position, =CH-N(CH₃)₂ at 4-position, N-Ar at N1, C=O at 3-position.

| Example No. | R¹ | Ar | mp |
|---|---|---|---|
| III-64 | H | 2,4,6-trichlorophenyl | >250 |
| III-65 | H | phenyl | 210 |
| III-66 | H | 3-chlorophenyl | 192–198 |
| III-67 | H | 4-chlorophenyl | 242–243 |
| III-68 | 2,4-dichlorophenyl | 4-chlorophenyl | 163 |
| III-69 | CH₃ | 4-(trifluoromethyl)phenyl | 230–233 |
| III-70 | H | 2,6-dichloro-4-(trifluoromethyl)phenyl | 220 |
| III-71 | phenyl | 4-fluorophenyl | 136 |
| III-72 | 3-methylphenyl | 4-fluorophenyl | 143–144 |
| III-73 | CH₃ | 4-nitrophenyl | >300 |

TABLE 8-continued (III) Structure: R¹ and CH—N(CH₃)₂ on pyrazolone ring with N—N—Ar, C=O

| Example No. | R¹ | Ar | Melting Point (°C.) or ¹H-NMR in CDCl₃ (δ N(CH₃)₂) |
|---|---|---|---|
| III-74 | CH₃ | 3-CF₃-C₆H₄— | 130 |
| III-75 | CH₃ | 2-Cl-4-CF₃-C₆H₃— | 3.27/3.79 |
| III-76 | 3-NC-C₆H₄— | 4-F-C₆H₄— | 219 |
| III-77 | n-C₃H₇ | 2-Cl-4-CF₃-C₆H₃— | 3.32/3.83 |
| III-78 | n-C₃H₇ | 4-CF₃-C₆H₄— | 111–112 |
| III-79 | 3-CH₃O-C₆H₄— | 4-F-C₆H₄— | 135–136 |
| III-80 | n-C₃H₇ | 4-O₂N-C₆H₄— | 139 |
| III-81 | n-C₃H₇ | 3-CF₃-C₆H₄— | 108–109 |
| III-82 | (CH₃)₂CH—CH₂— | 4-Cl-C₆H₄— | 114 |
| III-83 | (CH₃)₂CH— | 4-Cl-C₆H₄— | 107 |

TABLE 8-continued $$\underset{Ar}{\underset{N-N}{R^1}}\overset{CH-N(CH_3)_2}{\underset{O}{\bigvee}}$$ (III)

| Example No. | R¹ | Ar | |
|---|---|---|---|
| III-84 | n-C₄H₉ | 4-Cl-C₆H₄– | 194 |
| III-85 | (CH₃)₃C | 4-Cl-C₆H₄– | 3.30/3.65 |
| III-86 | n-C₃H₇ | 2,3-(CH₃)₂-C₆H₃– | 103–105 |
| III-87 | CH₃ | 2,4-Cl₂-3-CF₃-C₆H₂– (2,4-Cl, 3-CF₃) | 3.35/3.80 |
| III-88 | CH₃ | 4-CH₃O₂S-C₆H₄– | 3.22/3.79 |
| III-89 | C₂H₅SCH₂– | 4-F-C₆H₄– | 138 |
| III-90 | C₂H₅SCH₂– | 4-Cl-C₆H₄– | 119 |
| III-91 | C₆H₅– | 4-NC-C₆H₄– | 173 |
| III-92 | 4-CH₃-C₆H₄– | 2,5-Cl₂-3-CF₃-C₆H₂– | 142 |
| III-93 | 4-CH₃-C₆H₄– | 4-Cl-C₆H₄– | 175 |

TABLE 8-continued
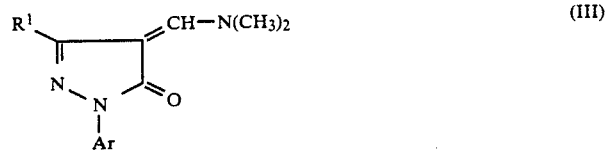
(III)
| Example No. | R¹ | Ar | m.p. |
|---|---|---|---|
| III-94 | 3-Cl-C₆H₄ | 4-O₂N-C₆H₄ | 201 |
| III-95 | 3-Cl-C₆H₄ | 4-Cl-C₆H₄ | 171 |
| III-96 | 2,4-Cl₂-C₆H₃ | 2,6-Cl₂-4-CF₃-C₆H₂ | 180–182 |
| III-97 | C₂H₅O—C(O)— | 4-Cl-C₆H₄ | 124–126 |
| III-98 | C₂H₅O—C(O)—CH₂— | 4-Cl-C₆H₄ | 150 |
| III-99 | n-C₃H₇ | 4-CF₃O₂S-C₆H₄ | 156 |
| III-100 | CH₃—C(O)—NH— | 2,6-Cl₂-4-CF₃-C₆H₂ | 264 |
| III-101 | CH₃—C(O)—NH— | 2,6-Cl₂-4-CF₃-C₆H₂ | 55–60 |
| III-102 | C₆H₅—CH₂— | 2,6-Cl₂-4-CF₃-C₆H₂ | 175–178 |

TABLE 8-continued (III) Structure: R¹ at 3-position, 4-position bearing =CH—N(CH₃)₂, pyrazolinone with N—Ar and C=O.

| Example No. | R¹ | Ar | |
|---|---|---|---|
| III-103 | C₆H₅—CH₂— | 4-O₂N—C₆H₄— | 213 |
| III-104 | C₆H₅—CH₂— | 3-CF₃—C₆H₄— | 130 |
| III-105 | C₆H₅—CH₂— | 4-Cl—C₆H₄— | 115 |
| III-106 | C₆H₅—CH₂— | 3-Cl-4-(CF₃O₂S)—C₆H₃— | 124 |
| III-107 | C₆H₅— | 4-(CF₃O₂S)—C₆H₄— | 234 |
| III-108 | n-C₃H₇ | 4-(CH₃O₂C)—C₆H₄— | 57 |
| III-109 | C₂H₅O— | 4-O₂N—C₆H₄— | 207 |
| III-110 | C₂H₅O— | 2,6-Cl₂-4-CF₃—C₆H₂— | 98 |
| III-111 | C₆H₅—CH₂ | 4-F—C₆H₄— | 135 |
| III-112 | 3-Cl—C₆H₄— | 4-F—C₆H₄— | 161 |
| III-113 | 2-Cl—C₆H₄— | 4-F—C₆H₄— | 88–92 |

TABLE 8-continued $$\underset{\text{Ar}}{\overset{R^1}{\underset{N}{\bigvee}}}\overset{CH-N(CH_3)_2}{\underset{O}{\bigvee}}\quad\text{(III)}$$

| Example No. | R¹ | Ar | mp (°C) |
|---|---|---|---|
| III-114 | C₂H₅O— | 4-F-C₆H₄— | 127 |
| III-115 | 2-Cl-C₆H₄-CH₂— | 4-F-C₆H₄— | 135 |
| III-116 | 3-Cl-C₆H₄-CH₂— | 3,5-Cl₂-4-CF₃-C₆H₂— (2,6-Cl₂-4-CF₃-C₆H₂—) | 132 |
| III-117 | 3-Cl-C₆H₄-CH₂— | 4-F-C₆H₄— | 150 |
| III-118 | 4-Cl-C₆H₄-CH₂— | 3,5-Cl₂-4-CF₃-C₆H₂— | 140 |
| III-119 | 4-Cl-C₆H₄-CH₂ | 4-F-C₆H₄— | 119 |
| III-120 | 2,4-Cl₂-C₆H₃— | 4-F-C₆H₄— | 164 |
| III-121 | 4-Cl-C₆H₄-OCH₂— | 4-F-C₆H₄— | 152–154 |
| III-122 | C₆H₅— | 3-CF₃-C₆H₄— | 137–138 |
| III-123 | CH₃ | 2,4-F₂-C₆H₃— | 138 |

TABLE 8-continued
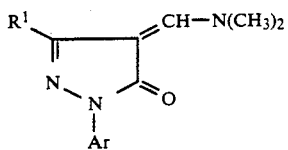
| Example No. | R¹ | Ar | |
|---|---|---|---|
| III-124 | n-C₃H₇ | 2,4-difluorophenyl | 125 |
| III-125 | phenyl | 2,4-difluorophenyl | 122 |
| III-126 | 3-CF₃-phenyl | 2,4-difluorophenyl | 72 |
| III-127 | 3-CF₃-phenyl | 4-F-phenyl | 158 |
| III-128 | phenyl | phenyl | 148–151 |
| III-129 | 4-Cl-C₆H₄-S-CH₂- | 4-F-phenyl | 143–145 |
| III-130 | 2,4-Cl₂-C₆H₃-CH₂- | 4-F-phenyl | 164–165 |
| III-131 | 2,4-Cl₂-C₆H₃-CH₂- | 3-CF₃-phenyl | 99–101 |
| III-132 | C₆H₅-CH₂- | 3-CF₃-phenyl | 116–119 |
| III-133 | 4-Cl-C₆H₄-S-CH₂- | 3-CF₃-2,5-Cl₂-phenyl | 182–184 |

TABLE 8-continued (III) [structure: R¹ at position with CH=N(CH₃)₂ group, pyrazolone ring with N-N-Ar, =O]

| Example No. | R¹ | Ar | |
|---|---|---|---|
| III-134 | 3-(CF₃)C₆H₄-CH₂- | 4-F-C₆H₄- | 113-114 |
| III-135 | (CH₃)₃C-CH₂- | 4-F-C₆H₄- | 128 |
| III-136 | C₆H₅- | 3-Cl-4-(CF₃O₂S)-C₆H₃- | 171 |
| III-137 | C₆H₅-CH₂- | 2,4-F₂-C₆H₃- | 123-124 |
| III-138 | 3-(CF₃)C₆H₄-CH₂- | 2,4-F₂-C₆H₃- | 120-122 |
| III-139 | 2-F-C₆H₄- | 4-F-C₆H₄- | 161-162 |
| III-140 | C₆H₅- | 5-O₂N-2-pyridyl | 196-198 |
| III-141 | 3-O₂N-C₆H₄- | 4-F-C₆H₄- | 251-253 |
| III-142 | 2,5-Cl₂-C₆H₃- | 4-F-C₆H₄- | 130 |
| III-143 | C₂H₅O-C(O)- | 4-F-C₆H₄- | 148-149 |

TABLE 8-continued $$\text{(III)}$$

Structure (III): pyrazolone with R¹ at 5-position, =CH–N(CH₃)₂ at 4-position, =O at 3-position, N-Ar at 1-position.

| Example No. | R¹ | Ar | mp (°C) |
|---|---|---|---|
| III-144 | 3-Cl-C₆H₄– | 6-(5-nitropyridin-2-yl)– | 272 |
| III-145 | 2-Cl-C₆H₄– | 6-(5-nitropyridin-2-yl)– | 240 |
| III-146 | C₆H₅–CH₂CH₂– | 4-F-C₆H₄– | 114 |
| III-147 | 3-CF₃-C₆H₄– | 4-(CH₃O₂S)-C₆H₄– | 138 |
| III-148 | 3-Cl-C₆H₄– | 4-(CH₃O₂S)-C₆H₄– | 174 |
| III-149 | 2-Cl-C₆H₄– | 4-(CH₃O₂S)-C₆H₄– | 213 |
| III-150 | C₆H₅– | 4-(CH₃O₂S)-C₆H₄– | 185–186 |
| III-151 | 3-CF₃-C₆H₄– | 4-NC-C₆H₄– | 178 |
| III-152 | 3-Cl-C₆H₄– | 4-NC-C₆H₄– | 195–198 |
| III-153 | 2-Cl-C₆H₄– | 4-NC-C₆H₄– | 201 |

TABLE 8-continued (III) structure: R¹ substituted pyrazolone with =CH—N(CH₃)₂, N-Ar

| Example No. | R¹ | Ar | |
|---|---|---|---|
| III-154 | CH₃ | 3-Cl, 4-(substituent), 5-F, with F₃C at position | 201 |
| III-155 | 2-Cl-phenyl | 2,4-difluorophenyl | 128 |
| III-156 | 3-Cl-phenyl | 2,4-difluorophenyl | 137 |
| III-157 | 3-NC-phenyl | 2,4-difluorophenyl | 149 |
| III-158 | 2-F-phenyl | 2,4-difluorophenyl | 120 |
| III-159 | 3-H₃C-phenyl | 2,4-difluorophenyl | 108 |
| III-160 | 3-CH₃O-phenyl | 2,4-difluorophenyl | 110 |
| III-161 | 3,5-diCl-phenyl | 4-F-phenyl | 236 |
| III-162 | 3-F₃C-phenyl | 4-NO₂-phenyl | 214 |

TABLE 8-continued (III) structure: $R^1$-pyrazolin-5-one with =CH-N(CH$_3$)$_2$ at 4-position and Ar on N1

| Example No. | R$^1$ | Ar | m.p. (°C) |
|---|---|---|---|
| III-163 | 2-fluorophenyl | 4-NC-phenyl | 215 |
| III-164 | phenyl | 2,5-dichlorophenyl | 130 |
| III-165 | 3-(trifluoromethyl)phenyl | 4-chlorophenyl | 156 |
| III-166 | 5-methylfuran-2-yl | 4-fluorophenyl | 133 |
| III-167 | furan-2-ylmethyl | 4-fluorophenyl | 116–117 |

The substituted pyrazolin-5-one derivatives of the formula (If) listed in the following Table 9

(If) structure: $R^{1-1}$-pyrazolin-5-one with =CH-N(R$^{7-1}$)(R$^{7-2}$) at 4-position and phenyl on N1 can be obtained as in the given process, cf, in particular, the performance of the reaction according to the preparation examples [(Ia)-1] and [(Ia)-2]:

TABLE 9

| Example No. | R$^{1-1}$ | R$^{7-1}$ | R$^{7-2}$ | Melting point (°C.) |
|---|---|---|---|---|
| If-1 | 3-(trifluoromethyl)phenyl | CH$_3$ | CH$_3$ | 190 |
| If-2 | 3-(trifluoromethyl)benzyl | CH$_3$ | CH$_3$ | 125 |
| If-3 | 3-chlorophenyl | CH$_3$ | CH$_3$ | 170 |
| If-4 | 2-chlorophenyl | CH$_3$ | CH$_3$ | 112–113 |
| If-5 | 3-methoxyphenyl | CH$_3$ | CH$_3$ | 125 |

TABLE 9-continued

| Example No. | R¹⁻¹ | R⁷⁻¹ | R⁷⁻² | Melting point (°C.) |
|---|---|---|---|---|
| If-6 | 3-cyanophenyl (NC-C₆H₄-) | CH₃ | CH₃ | 162–163 |
| If-7 | 3-methylphenyl (CH₃-C₆H₄-) | CH₃ | CH₃ | 154 |
| If-8 | 2,4-dichlorophenyl | CH₃ | CH₃ | |
| If-9 | 3-nitrophenyl (O₂N-C₆H₄-) | CH₃ | CH₃ | |
| If-10 | C₆H₅-CH₂CH₂- | CH₃ | CH₃ | 109 |
| If-11 | 3-methylphenyl | H | CH₃ | 126 |
| If-12 | 3-cyanophenyl | H | CH₃ | 179 |
| If-13 | 3-methoxyphenyl (CH₃O-C₆H₄-) | H | CH₃ | 138–139 |
| If-14 | 3-chlorophenyl | H | CH₃ | 119–120 |
| If-15 | 2-chlorophenyl | H | CH₃ | 190–191 |
| If-16 | C₆H₅-CH₂-CH₂- | H | CH₃ | 118 |
| If-17 | 3-nitrophenyl | H | CH₃ | 238 |
| If-18 | 2,4-dichlorophenyl | H | CH₃ | 138 |
| If-19 | n-C₃H₇ | CH₃ | CH₃ | 136 |
| If-20 | 3,5-dichlorophenyl | H | CH₃ | 213–214 |
| If-21 | furan-2-yl | CH₃ | CH₃ | 125 |
| If-22 | furan-2-ylmethyl | CH₃ | CH₃ | 147 |
| If-23 | furan-2-yl | H | CH₃ | 128 |
| If-24 | furan-2-ylmethyl | H | CH₃ | 100–101 |
| If-25 | thiophen-2-ylmethyl | H | CH₃ | 100–101 |
| If-26 | 2-methylphenyl | H | CH₃ | 121 |
| If-27 | 3-bromophenyl | H | CH₃ | 136 |

The intermediates of the formula (IV), (IVa), (IVb) or (IVc), which are summarized in the general formula (IVa), can be obtained analogously to the preparation example (IV-1) and as in the given process:

TABLE 10

Structure (IVa): pyrazolone with R¹, CHO, N-N-Ar, =O

| Example No. | R¹ | Ar | Melting point (°C.) |
|---|---|---|---|
| (IV-2) | —CH$_2$SCH$_3$ | 3-Cl-phenyl | Oil |
| (IV-3) | —CH$_2$SCH$_3$ | 4-NO$_2$-phenyl | 125 |
| (IV-4) | —CH$_2$SCH$_3$ | 4-F-phenyl | 90 |
| (IV-5) | —CH$_2$SCH$_3$ | 2,4,5-trichlorophenyl | 103 |
| (IV-6) | —CH$_2$SCH$_3$ | 4-CF$_3$-phenyl | 127 |
| (IV-7) | H | 3-CF$_3$-2,5-dichlorophenyl | 110 |
| (IV-8) | H | phenyl | 182 |
| (IV-9) | H | 4-Cl-phenyl | 204 |
| (IV-10) | H | 4-F-phenyl | 159–160 |

The intermediates of the formula (VI) listed in Table 11

$$\text{(VI)}$$

or of the formula (VIa)

$$\text{(VIa)}$$

in which
Ar² represents unsubstituted phenyl,
can be obtained analogously to the preparation examples (VI-1), (VI-2) and (VI-3) and as in the given processes. Compounds of the formula (VIa) here serve as intermediates for the preparation of known compounds of the formula (I).

TABLE 11

| Example No. | R¹ | Ar¹ | Melting point (°C.) |
|---|---|---|---|
| (VI-4) | —CH$_2$SCH$_3$ | 3-Cl-phenyl | 89 |
| (VI-5) | —CH$_2$SCH$_3$ | 2-Cl-phenyl | 144 |

TABLE 11-continued

| Example No. | R¹ | Ar¹ | Melting point (°C.) |
|---|---|---|---|
| (VI-6) | —CH$_2$SCH$_3$ | 4-F-C$_6$H$_4$ | 63 |
| (VI-7) | H | 2,5-Cl$_2$-3-CF$_3$-C$_6$H$_2$ (2,3-Cl$_2$-6-CF$_3$,5-Cl) | 183–185 |
| (VI-8) | —COOC$_2$H$_5$ | 4-Cl-C$_6$H$_4$ | 167–168 |
| (VI-9) | CF$_3$ | 3-Cl-4-CF$_3$-C$_6$H$_3$ | 208–209 |
| (VI-10) | CH$_3$ | 2,4,6-Cl$_3$-C$_6$H$_2$ | 171 |
| (VI-11) | n-C$_3$H$_7$ | 2,4,6-Cl$_3$-C$_6$H$_2$ | 159 |
| (VI-12) | CH$_3$ | 3-Cl-C$_6$H$_4$ | 124 |
| (VI-13) | n-C$_3$H$_7$ | 4-Cl-C$_6$H$_4$ | 90–91 |
| (VI-14) | CH$_3$ | 4-Cl-C$_6$H$_4$ | 169 |
| (VI-15) | (CH$_3$)$_3$C | 2,4-Cl$_2$-5-CF$_3$-C$_6$H$_2$ | 163 |

TABLE 11-continued
| Example No. | R¹ | Ar¹ | Melting point (°C.) |
|---|---|---|---|
| (VI-16) | $C_2H_5$ | 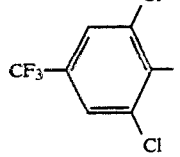 | 123 |
| (VI-17) | $n-C_3H_7$ | 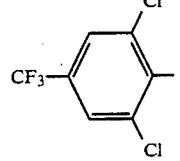 | 115 |
| (VI-18) | $(CH_3)_2CH-$ | 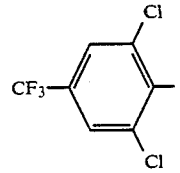 | 120 |
| (VI-19) | 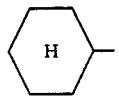 | 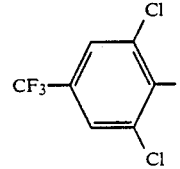 | 134 |
| (VI-20) | $n-C_3H_7$ | 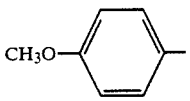 | 104–105 |
| (VI-21) | $CH_3$ | 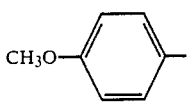 | 160 |
| (VI-22) | $n-C_3H_7$ | 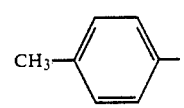 | 121 |
| (VI-23) |  | 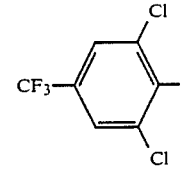 | 125–130 |
| (VI-24) | $CH_3$ | 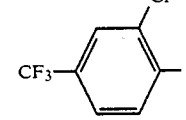 | 132–133 |
| (VI-25) | $CH_3$ | 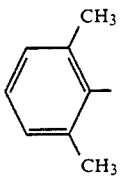 | 183–185 |

TABLE 11-continued

| Example No. | R¹ | Ar¹ | Melting point (°C.) |
|---|---|---|---|
| (VI-26) | n-$C_3H_7$ | 4-$CF_3$-$C_6H_4$- | 92-93 |
| (VI-27) | $CH_3$ | 4-$CF_3$-$C_6H_4$- | 172 |
| (VI-28) | $CH_3OCH_2$— | 4-$CF_3$-$C_6H_4$- | 83 |
| (VI-29) | n-$C_3H_7$ | 2-Cl-4-$CF_3$-$C_6H_3$- | 67 |
| (VI-30) | n-$C_3H_7$ | 4-$O_2N$-$C_6H_4$- | 131-132 |
| (VI-31) | n-$C_3H_7$ | 3-$CF_3$-$C_6H_4$- | 62-63 |
| (VI-32) | $(CH_3)_2CH$—$CH_2$— | 4-Cl-$C_6H_4$- | 107-109 |
| (VI-33) | $(CH_3)_2CH$ | 4-Cl-$C_6H_4$- | 120 |
| (VI-34) | n-$C_4H_9$ | 4-Cl-$C_6H_4$- | 55 |
| (VI-35) | $(CH_3)_3C$— | 4-Cl-$C_6H_4$- | 119-122 |
| (VI-36) | $C_2H_5$ | 4-Cl-$C_6H_4$- | 91-93 |
| (VI-37) | n-$C_3H_7$ | 2,3-$(CH_3)_2$-$C_6H_3$- | 85 |

TABLE 11-continued

| Example No. | R¹ | Ar¹ | Melting point (°C.) |
|---|---|---|---|
| (VI-38) | $CH_3$ | 2,3-dimethylphenyl | 133–135 |
| (VI-39) | $CH_3OCH_2$ | 4-chlorophenyl | 124 |
| (VI-40) | $CH_3$ | 2,4-dichloro-3-(trifluoromethyl)phenyl | 162–163 |
| (VI-41) | $C_2H_5$ | 4-(trifluoromethoxy)phenyl | 85–86 |
| (VI-42) | $n$-$C_3H_7$ | 4-(trifluoromethoxy)phenyl | 88–90 |
| (VI-43) | $CH_3$ | 4-(trifluoromethoxy)phenyl | 90–91 |
| (VI-44) | $CF_3$ | 4-chlorophenyl | 215 |
| (VI-45) | $C_2H_5$—S—$CH_2$— | 2,6-dichloro-4-(trifluoromethyl)phenyl | 108–110 (decomposition) |
| (VI-46) | $C_2H_5$—$SCH_2$— | 4-chlorophenyl | 87 |
| (VI-47) | $n$-$C_3H_7$ | 3-chloro-2,5-bis(trifluoromethyl)phenyl | 104–105 |
| (VI-48) | $n$-$C_3H_7$ | 4-chloro-2-methylphenyl | 162–163 |

TABLE 11-continued

| Example No. | R¹ | Ar¹ | Melting point (°C.) |
|---|---|---|---|
| (VI-49) | n-C₃H₇ | 4-F-C₆H₄- | 69–70 |
| (VI-50) | CH₃ | 2-pyridyl | 99–100 |
| (VI-51) | n-C₃H₇ | 3-Cl-5-(CF₃O₂S)-C₆H₃- | 124–126 |
| (VI-52) | n-C₃H₇ | 4-(CH₃O₂S)-C₆H₄- | 99–100 |
| (VI-53) | n-C₃H₇ | 4-(CF₃O₂S)-C₆H₄- | 63–64 |
| (VI-54) | 2-furyl | 4-O₂N-C₆H₄- | 186–187 |
| (VI-55) | C₂H₅—S—CH₂— | 2,3,5-Cl₃-4-CF₃-C₆H- | 66–68 |
| (VI-56) | C₂H₅—S—CH₂— | 4-CF₃-C₆H₄- | 67 |
| (VI-57) | C₂H₅—C(O)—CH₂— | 4-Cl-C₆H₄- | 110 |
| (VI-58) | 3-F-C₆H₄- | 4-F-C₆H₄- | 121–123 |
| (VI-59) | CH₃—C(O)—NH— | 3,5-Cl₂-4-CF₃-C₆H₂- | 233 |

TABLE 11-continued
| Example No. | R¹ | Ar¹ | Melting point (°C.) |
|---|---|---|---|
| (VI-60) | CH₃ | 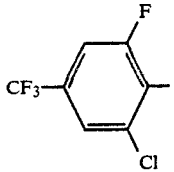 | 168–173 |
| (VI-61) | n-C₃H₇ | 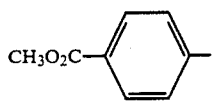 | 135–137 |
| (VI-62) | C₂H₅O— | 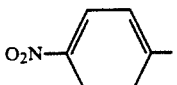 | 143 |
| (VI-63) | C₂H₅O— | 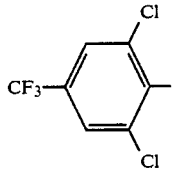 | 113 |
| (VI-64) | C₂H₅O | 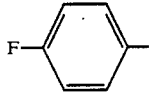 | 112 |
| (VI-65) | CH₃ | 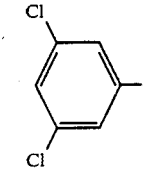 | 141–142 |
| (VI-66) | n-C₃H₇ | 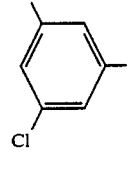 | 83–85 |
| (VI-67) | CH₃ | 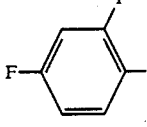 | 96–97 |
| (VI-68) | n-C₃H₇ | 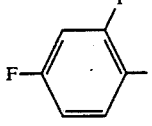 | 87–88 |
| (VI-69) | 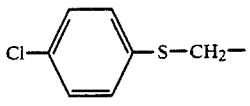 | 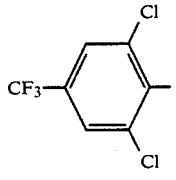 | 105–107 |

TABLE 11-continued
| Example No. | R¹ | Ar¹ | Melting point (°C.) |
|---|---|---|---|
| (VI-70) | 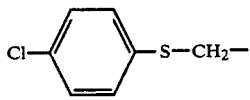 | 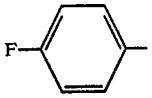 | 108–111 |
| (VI-71) | (CH₃)₃C—CH₂ | 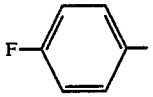 | 146–147 |
| (VI-72) | 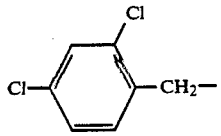 | 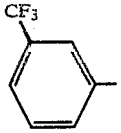 | 119 |
| (VI-73) | 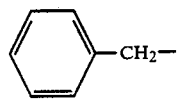 | 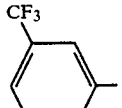 | 134 |
| (VI-74) | 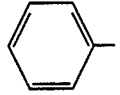 | 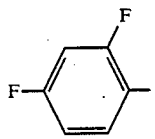 | 169–170 |
| (VI-75) | 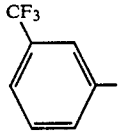 | 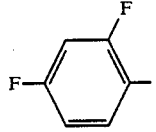 | 111 |
| (VI-76) | 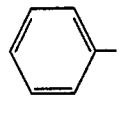 | 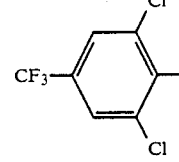 | 151–152 |
| (VI-77) | 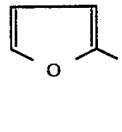 | 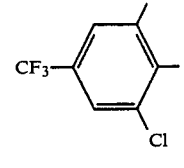 | 210–211 |
| (VI-78) | 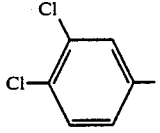 | 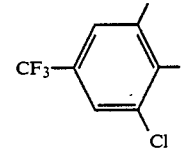 | 165–166 |
| (VI-79) | 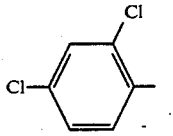 | 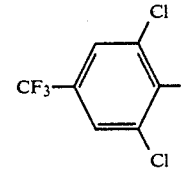 | 186–187 |

TABLE 11-continued

| Example No. | R¹ | Ar¹ | Melting point (°C.) |
|---|---|---|---|
| (VI-80) | 4-Cl-C₆H₄- | 2,4-Cl₂-5-CF₃-C₆H₂- | 184–185 |
| (VI-81) | 4-CH₃-C₆H₄- | 2,4-Cl₂-5-CF₃-C₆H₂- | 177–178 |
| (VI-82) | 3-Cl-C₆H₄- | 2,4-Cl₂-5-CF₃-C₆H₂- | 160–161 |
| (VI-83) | 2-Cl-C₆H₄- | 2,4-Cl₂-5-CF₃-C₆H₂- | 178–179 |
| (VI-84) | C₆H₅-CH₂- | 2,4-Cl₂-5-CF₃-C₆H₂- | 185 |
| (VI-85) | C₆H₅-CH₂- | 4-O₂N-C₆H₄- | 121 |
| (VI-86) | 3-Cl-C₆H₄-CH₂- | 2,4-Cl₂-5-CF₃-C₆H₂- | 149–150 |
| (VI-87) | 4-Cl-C₆H₄-CH₂- | 2,4-Cl₂-5-CF₃-C₆H₂- | 177 |
| (VI-88) | C₆H₅- | 3,5-Cl₂-C₆H₃- | 155–157 |

TABLE 11-continued

| Example No. | R¹ | Ar¹ | Melting point (°C.) |
|---|---|---|---|
| (VI-89) | C₆H₅-CH₂- | 3-CF₃-C₆H₄- | 107 |
| (VI-90) | C₆H₅- | 3-CF₃-C₆H₄- | 112-113 |
| (VI-91) | 3-Cl-C₆H₄- | 4-CF₃-C₆H₄- | 127-128 |
| (VI-92) | C₆H₅- | 4-Cl-C₆H₄- | 156-157 |
| (VI-93) | 4-CH₃-C₆H₄- | 4-Cl-C₆H₄- | 159-160 |
| (VI-94) | 3-Cl-C₆H₄- | 4-Cl-C₆H₄- | 122-123 |
| (VI-95) | 2-Cl-C₆H₄- | 4-Cl-C₆H₄- | 137-138 |
| (VI-96) | 3,4-Cl₂-C₆H₃- | 4-Cl-C₆H₄- | 181-182 |
| (VI-97) | 2,4-Cl₂-C₆H₃- | 4-Cl-C₆H₄- | 175-176 |
| (VI-98) | C₆H₅- | 4-F-C₆H₄- | 156-157 |
| (VI-99) | C₆H₅-CH₂- | 4-F-C₆H₄- | 148-149 |

TABLE 11-continued
| Example No. | R¹ | Ar¹ | Melting point (°C.) |
|---|---|---|---|
| (VI-100) | 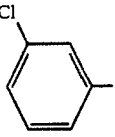 3-Cl-C₆H₄- | 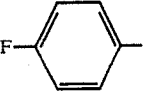 4-F-C₆H₄- | 112 |
| (VI-101) | 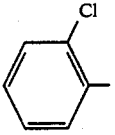 2-Cl-C₆H₄- | 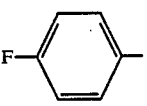 4-F-C₆H₄- | 135–137 |
| (VI-102) | 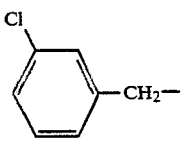 3-Cl-C₆H₄-CH₂- | 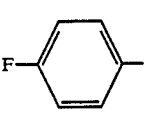 4-F-C₆H₄- | 101 |
| (VI-103) | 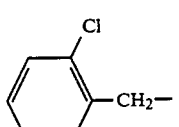 2-Cl-C₆H₄-CH₂- | 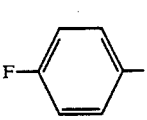 4-F-C₆H₄- | 101 |
| (VI-104) | 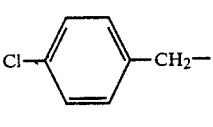 4-Cl-C₆H₄-CH₂- | 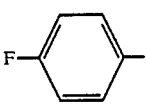 4-F-C₆H₄- | 105 |
| (VI-105) | 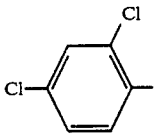 2,4-Cl₂-C₆H₃- | 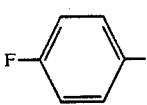 4-F-C₆H₄- | 159 |
| (VI-106) | 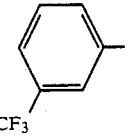 3-CF₃-C₆H₄- | 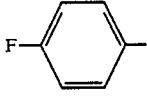 4-F-C₆H₄- | 83 |
| (VI-107) | 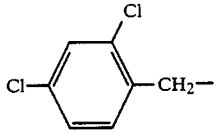 2,4-Cl₂-C₆H₃-CH₂- | 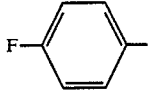 4-F-C₆H₄- | 138 |
| (VI-108) | 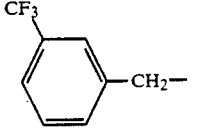 3-CF₃-C₆H₄-CH₂- | 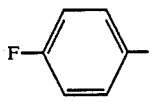 4-F-C₆H₄- | 93–94 |
| (VI-109) | 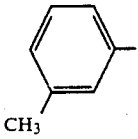 3-CH₃-C₆H₄- | 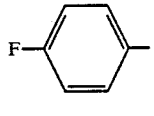 4-F-C₆H₄- | 127 |
| (VI-110) | 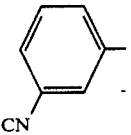 3-CN-C₆H₄- | 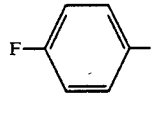 4-F-C₆H₄- | 127 |

TABLE 11-continued
| Example No. | R¹ | Ar¹ | Melting point (°C.) |
|---|---|---|---|
| (VI-111) | 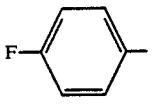 3-CH₃O-C₆H₄- | 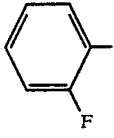 4-F-C₆H₄- | 163–166 |
| (VI-112) | 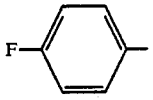 2-F-C₆H₄- | 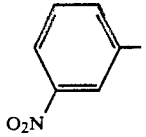 4-F-C₆H₄- | 111–112 |
| (VI-113) | 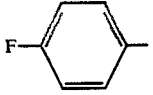 3-O₂N-C₆H₄- | 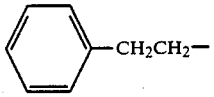 4-F-C₆H₄- | 144–145 |
| (VI-114) | 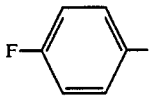 C₆H₅-CH₂CH₂- | 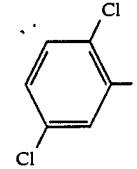 4-F-C₆H₄- | 130 |
| (VI-115) | 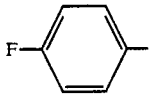 2,5-Cl₂-C₆H₃- | 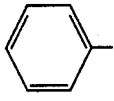 4-F-C₆H₄- | 147 |
| (VI-116) | 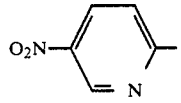 C₆H₅- | 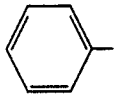 5-O₂N-pyridin-2-yl | 220–225 |
| (VI-117) | 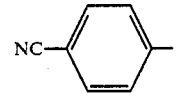 C₆H₅- | 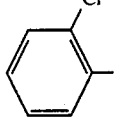 4-NC-C₆H₄- | 178 |
| (VI-118) | 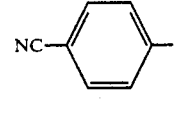 2-Cl-C₆H₄- | 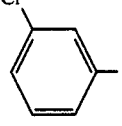 4-NC-C₆H₄- | 178 |
| (VI-119) | 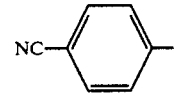 3-Cl-C₆H₄- | 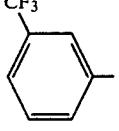 4-NC-C₆H₄- | 205 |
| (VI-120) | 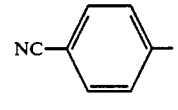 3-CF₃-C₆H₄- | 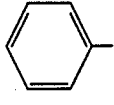 4-NC-C₆H₄- | 184 |
| (VI-121) | 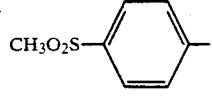 C₆H₅- | 4-CH₃O₂S-C₆H₄- | 188 |

TABLE 11-continued

| Example No. | R¹ | Ar¹ | Melting point (°C.) |
|---|---|---|---|
| (VI-122) | 2-Cl-C₆H₄- | 4-(CH₃O₂S)-C₆H₄- | 181 |
| (VI-123) | 3-Cl-C₆H₄- | 4-(CH₃O₂S)-C₆H₄- | 202 |
| (VI-124) | 2-Cl-C₆H₄- | 6-F-3-(O₂N)-pyridin-2-yl (5-nitro-2-fluoropyridyl) | 165 |
| (VI-125) | 3-Cl-C₆H₄- | 6-F-3-(O₂N)-pyridin-2-yl | 189 |
| (VI-126) | C₆H₅- | 3-Cl-4-(CF₃O₂S)-C₆H₃- | 155–157 |
| (VI-127) | 3-(CF₃)-C₆H₄-CH₂- | 2,4-F₂-C₆H₃- | 135 |
| (VI-128) | C₆H₅-CH₂- | 2,4-F₂-C₆H₃- | 115 |
| (VI-129) | C₆H₅-CH₂- | 3-(CF₃)-C₆H₄- | 107 |
| (VI-130) | C₆H₅-CH₂- | 3-Cl-4-(CF₃O₂S)-C₆H₃- | 74 |
| (VI-131) | C₆H₅- | 4-(CF₃O₂S)-C₆H₄- | 132 |
| (VI-132) | C₆H₅- | 4-(O₂N)-C₆H₄- | 204–205 |

TABLE 11-continued

| Example No. | R¹ | Ar¹ | Melting point (°C.) |
|---|---|---|---|
| (VI-133) | 3-Cl-C₆H₄- | 4-O₂N-C₆H₄- | 203-204 |
| (VI-134) | 3-CH₃-C₆H₄- | 4-O₂N-C₆H₄- | 196-197 |
| (VI-135) | 4-Cl-C₆H₄- | 4-O₂N-C₆H₄- | 183-184 |
| (VI-136) | C₆H₅-C(O)-NH- | 3,5-Cl₂-4-CF₃-C₆H₂- | 288 |
| (VI-137) | 3-CH₃-C₆H₄- | C₆H₅- | 114 |
| (VI-138) | 3-NC-C₆H₄- | C₆H₅- | 173-174 |
| (VI-139) | 3-CH₃O-C₆H₄- | C₆H₅- | 113 |
| (VI-140) | 3-NO₂-C₆H₄- | C₆H₅- | 164 |
| (VI-141) | 3-Cl-C₆H₄- | C₆H₅- | 94-96 |
| (VI-142) | 2-Cl-C₆H₄- | C₆H₅- | 133-134 |
| (VI-143) | C₆H₅-CH₂CH₂- | C₆H₅- | 125 |

TABLE 11-continued

| Example No. | R¹ | Ar¹ | Melting point (°C.) |
|---|---|---|---|
| (VI-144) | 2,4-dichlorophenyl | phenyl | 179 |
| (VI-145) | 3-(trifluoromethyl)benzyl (–CH₂–) | phenyl | 135 |
| (VI-146) | CH₃ | 3-fluoro-5-(trifluoromethyl)-2-chlorophenyl (F, F₃C, Cl substituted) | |
| (VI-147) | 2-chlorophenyl | 3,4-difluorophenyl | 80 |
| (VI-148) | 3-chlorophenyl | 3,4-difluorophenyl | 132 |
| (VI-149) | 3-methylphenyl | 3,4-difluorophenyl | 78 |
| (VI-150) | 3-cyanophenyl | 3,4-difluorophenyl | 128 |
| (VI-151) | 2-fluorophenyl | 3,4-difluorophenyl | 133 |
| (VI-152) | 3-methoxyphenyl | 3,4-difluorophenyl | 112 |
| (VI-153) | 3,5-dichlorophenyl | 4-fluorophenyl | 141–142 |

TABLE 11-continued

| Example No. | R¹ | Ar¹ | Melting point (°C.) |
|---|---|---|---|
| (VI-154) | 3-(F₃C)C₆H₄– | 4-(NO₂)C₆H₄– | 233 |
| (VI-155) | 3-(F₃C)C₆H₄– | 4-Cl-C₆H₄– | 116 |
| (VI-156) | 2-F-C₆H₄– | 4-(NC)C₆H₄– | 196 |
| (VI-157) | C₆H₅– | 2,4-Cl₂C₆H₃– | 162 |
| (VI-158) | 2-furyl– | 4-F-C₆H₄– | 124 |
| (VI-159) | 2-furyl-CH₂– | 4-F-C₆H₄– | 116 |
| (VI-160) | 2,4-Cl₂C₆H₃– | C₆H₅– | 143–144 |
| (VI-161) | 2-furyl– | C₆H₅– | 165 |
| (VI-162) | 2-furyl-CH₂– | C₆H₅– | 93–94 |

EXAMPLE VI-62

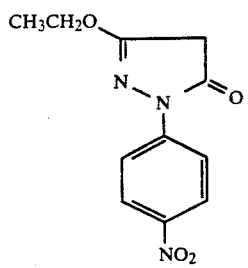

Process 4

9.3 g (0.06 mol) of 4-nitrophenylhydrazine and 11.4 g (0.06 mol) of ethyl-β,β-diethoxyacrylate are heated under reflux for 30 minutes in 50 ml of absolute ethanol. After addition of 1.4 g (0.06 mol) of sodium in 40 ml of absolute ethanol the reaction mixture is heated to reflux for a further 20 minutes, cooled and acidified with dilute acetic acid. The solid was then filtered off with suction, washed with water and dried (cf. U.S. Pat. No. 2,439,098).

11.0 g (73.6% of theory) of 3-ethoxy-1-(4-nitrophenyl)-pyrazolin-5-one of melting point 143° C. are obtained.

EXAMPLE 6

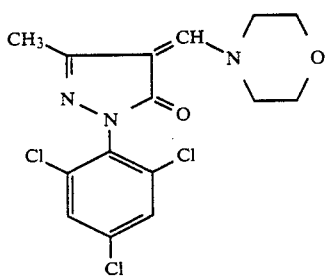
(I-1)

2.4 g (0.0079 mol) of 1-(2,4,6-trichlorophenyl)-4-formyl-3-methyl-pyrazolin-5-one are dissolved in 100 ml of dioxane and 0.7 g (0.0079 mol) of morpholine is added. The mixture is heated at 100° C. for one hour, then the solvent is stripped off and the residue is stirred with petroleum ether. The product is filtered off with suction and dried.

2.71 g (91.8% of theory) of 1-(2,4,6-trichlorophenyl)-3-methyl-4-morpholinyl-methylidene-pyrazolin-5-one of melting point 211°-212° C. are obtained.

The following compounds of the formula (I) are obtained analogously to the preparation example 6=compound (I-1):

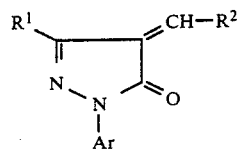
(I)

TABLE 12

| Example No. | $R^1$ | $R^2$ | Ar | Melting point (°C.) |
|---|---|---|---|---|
| (I-2) | $CH_3$ | 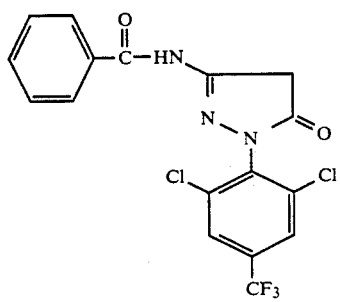 | | 199 |

EXAMPLE VI-136

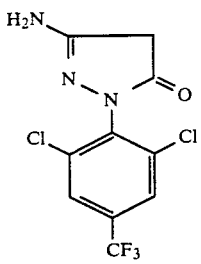

10 g (0.032 mol) of 1-(2,6-dichloro-4-trifluoromethylphenyl)-3-amino-pyrazolin-5-one are taken up in 100 ml of dioxane, and the mixture is heated to reflux for 5 hours after addition of 4.5 g (0.032 mol) of benzoyl chloride. The reaction mixture is then evaporated and stirred with water. The solid is filtered off with suction, washed several times with water and dried in air.

5.2 g (=39.1% of theory) of 1-(2,6-dichloro-4-trifluoromethylphenyl)-3-benzoylamino-pyrazolin-5-one of melting point 288° C. are obtained.

EXAMPLE XVIII-1

2.7 g (0.067 mol) of sodium are dissolved in 50 ml of ethanol, and then 24 g (0.068 mol) of ethyl β-(2,6-dichloro-4-trifluoromethylphenylhydrazino)-β-iminopropionate are added. The reaction mixture is heated under reflux for one hour and then evaporated in vacuo. After taking up the residue in water, the solution is extracted twice with ether, and the aqueous phase is acidified with dilute hydrochloric acid. The precipitated solid is filtered off with suction and dried.

9.6 g (45.9% of theory) of 1-(2,6-dichloro-4-trifluoromethylphenyl)-3-amino-pyrazolin-5-one of melting point 206°-207° C. are obtained.

EXAMPLE XVII-1

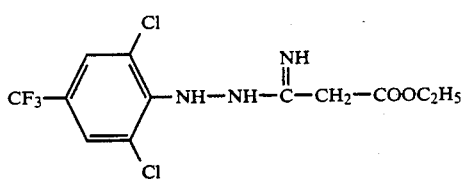

73.5 g (0.3 mol) of 2,6-dichloro-4-trifluoromethylphenylhydrazine and 47.7 g (0.3 mol) of ethyl β-imino-β-ethoxypropionate are heated under reflux for 1 hour in 300 ml of toluene. After cooling, petroleum ether is added to the reaction mixture, and the precipitated solid is filtered off with suction.

60.3 g (56.2% of theory) of ethyl β-(2,6-dichloro-4-trifluoromethylphenylhydrazino)-β-iminopropionate are obtained.

We claim:

1. Substituted pyrazolin-5-one derivatives of the formula

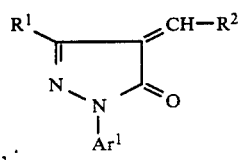

in which
$R^1$ is substituted or unsubstituted aryl,
$Ar^1$ is substituted aryl,
$R^2$ is $NHR^7$
wherein
$R^7$ is alkyl or alkenyl.

2. Substituted pyrazolin-5-one derivatives of the formula

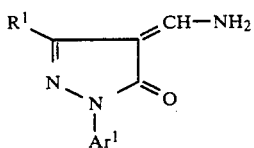

in which
$R^1$ is substituted or unsubstituted aryl, and
$Ar^1$ is substituted aryl.

3. Substituted pyrazolin-5-one derivatives of the formula

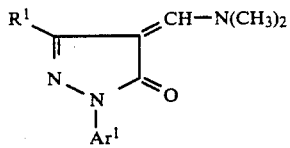

in which
$R^1$ is substituted or unsubstituted aryl, and
$Ar^1$ is substituted aryl,
excluding the compounds 1-(4-chlorophenyl)-3-(2-nitrophenyl)-4-N,N-dimethylamino-methylidenepyrazolin-5-one, 1-(3-trifluoromethylphenyl)-3-phenyl-4-N,N-dimethylaminomethylidene-pryazolin-5-one, and 1,3-bis-(3-trifluoromethylphenyl)-4-N,N-dimethylaminomethylene-pyrazolin-5-one.

4. Substituted pyrazolin-5-one derivatives of the formula

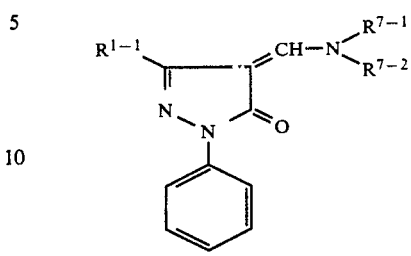

in which
$R^{1-1}$ is substituted aryl, and
$R^{7-1}$ and $R^{7-2}$ each are alkyl,
excluding the compounds 1-phenyl-3-(4-methoxyphenyl)-4-N,N-dimethylaminomethylidene-pyraxolin-5-one and 1-phenyl-3-(3-trifluoromethylphenyl)-4-N,N-dimethylaminomethylenepyrazolin-5-one.

5. Compounds of the formulae

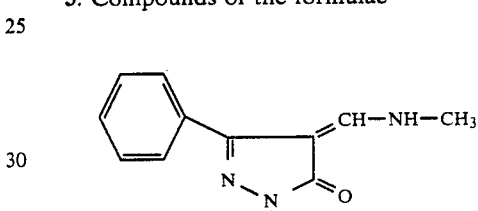

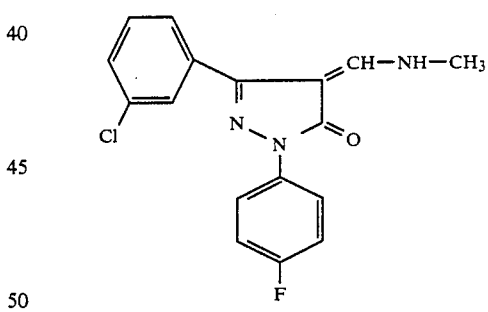

and

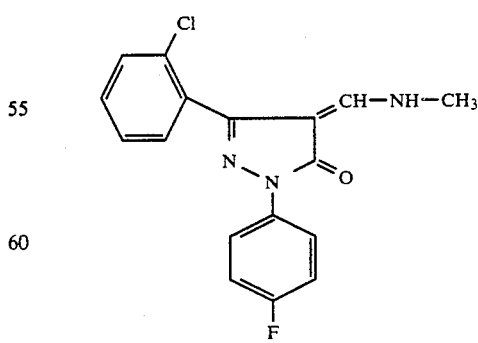

6. The compound 1-(4-fluorophenyl)-4-methylaminomethylidene-3-(2-methylphenyl)-pyrazoline-5-one of the formula

249
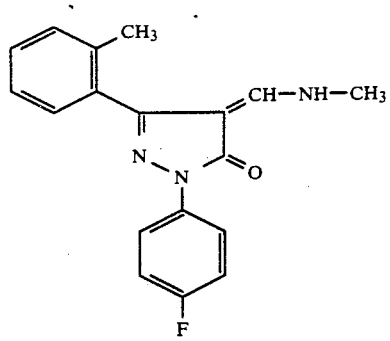
* * * * *
250
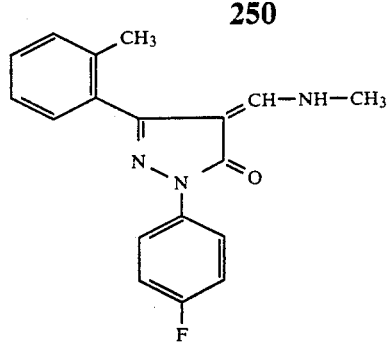
* * * * *